US007906625B2

(12) United States Patent
Shen et al.

(10) Patent No.: US 7,906,625 B2
(45) Date of Patent: Mar. 15, 2011

(54) HUMANIZED ANTI-AMYLOID ANTIBODY

(75) Inventors: Wenyan Shen, Palo Alto, CA (US); Anja L. Biere-Citron, Thousand Oaks, CA (US)

(73) Assignee: Amgen Inc., Thousand Oaks, CA (US)

( * ) Notice: Subject to any disclaimer, the term of this patent is extended or adjusted under 35 U.S.C. 154(b) by 481 days.

(21) Appl. No.: 11/576,220

(22) PCT Filed: Jan. 23, 2006

(86) PCT No.: PCT/US2006/002259
§ 371 (c)(1),
(2), (4) Date: Mar. 24, 2008

(87) PCT Pub. No.: WO2006/081171
PCT Pub. Date: Aug. 3, 2006

(65) Prior Publication Data
US 2008/0292639 A1 Nov. 27, 2008

Related U.S. Application Data

(60) Provisional application No. 60/646,658, filed on Jan. 24, 2005.

(51) Int. Cl.
| C12P 21/08 | (2006.01) |
| C07K 16/18 | (2006.01) |
| C12N 15/13 | (2006.01) |
| C12N 15/62 | (2006.01) |
| C12N 15/63 | (2006.01) |
| C12N 15/70 | (2006.01) |
| C12N 15/74 | (2006.01) |
| C12N 15/79 | (2006.01) |
| C07H 21/00 | (2006.01) |

(52) U.S. Cl. ........... 530/387.3; 530/387.9; 435/69.1; 435/320.1; 435/328; 435/252.3; 435/254.2; 536/23.53

(58) Field of Classification Search .................. None
See application file for complete search history.

(56) References Cited

U.S. PATENT DOCUMENTS

| 4,179,337 A | 12/1979 | Davis et al. |
| 4,301,144 A | 11/1981 | Iwashita et al. |
| RE30,985 E | 6/1982 | Cartaya |
| 4,495,285 A | 1/1985 | Shimizu et al. |
| 4,496,689 A | 1/1985 | Mitra |
| 4,560,655 A | 12/1985 | Baker |
| 4,609,564 A | 9/1986 | Pinkhasov |
| 4,640,835 A | 2/1987 | Shimizu et al. |
| 4,657,866 A | 4/1987 | Kumar |
| 4,666,829 A | 5/1987 | Glenner et al. |
| 4,670,417 A | 6/1987 | Iwasaki et al. |
| 4,766,106 A | 8/1988 | Katre et al. |
| 4,767,704 A | 8/1988 | Cleveland et al. |
| 4,791,192 A | 12/1988 | Nakagawa et al. |
| 4,816,567 A | 3/1989 | Cabilly et al. |
| 4,892,538 A | 1/1990 | Aebischer et al. |
| 4,927,762 A | 5/1990 | Darfler |
| 5,122,469 A | 6/1992 | Mather et al. |
| 5,200,339 A | 4/1993 | Abraham |
| 5,229,275 A | 7/1993 | Goroff |
| 5,283,187 A | 2/1994 | Aebischer et al. |
| 5,455,169 A | 10/1995 | Mullan |
| 5,530,101 A | 6/1996 | Queen et al. |
| 5,562,903 A * | 10/1996 | Co et al. ............... 424/133.1 |
| 5,565,332 A | 10/1996 | Hoogenboom et al. |
| 5,567,610 A | 10/1996 | Borrebaeck et al. |
| 5,573,905 A | 11/1996 | Lerner et al. |
| 5,585,089 A | 12/1996 | Queen et al. |
| 5,591,828 A | 1/1997 | Bosslet et al. |
| 5,693,762 A | 12/1997 | Queen et al. |
| 5,744,346 A | 4/1998 | Chrysler et al. |
| 5,766,886 A | 6/1998 | Studnicka et al. |
| 5,795,963 A | 8/1998 | Mullan |
| 5,877,293 A | 3/1999 | Adair et al. |
| 5,939,598 A | 8/1999 | Kucherlapati et al. |
| 5,942,400 A | 8/1999 | Anderson et al. |
| 6,054,287 A | 4/2000 | Gao et al. |
| 6,171,586 B1 | 1/2001 | Lam et al. |
| 6,221,645 B1 | 4/2001 | Chrysler et al. |
| 6,245,884 B1 | 6/2001 | Hook |
| 6,313,268 B1 | 11/2001 | Hook |
| 6,331,408 B1 | 12/2001 | Zaczek et al. |
| 6,489,123 B2 | 12/2002 | Osbourn et al. |
| 6,545,127 B1 | 4/2003 | Tang et al. |
| 6,583,268 B2 | 6/2003 | Lin |
| 6,737,038 B1 | 5/2004 | Zaczek et al. |
| 6,743,427 B1 | 6/2004 | Schenk |
| 6,787,637 B1 | 9/2004 | Schenk |

(Continued)

FOREIGN PATENT DOCUMENTS

EP  0315456  5/1989

(Continued)

OTHER PUBLICATIONS

Paul, Fundamental Immunology, (textbook), 1993, pp. 292-295.*
Rudikoff et al (Proc. Natl. Acad. Sci. USA 1982, 79 :1979-1983).*
Casset et al (Biochemical and Biophysical Research Communications, 2003, vol. 307, pp. 198-205.*
Vajdos et al. Journal of Molecular biology, 2002, vol. 320, pp. 415-428.*
Anderson, Human gene therapy, Nature, 392:25-30, 1998.
Aplin et al., Preparation, properties, and applications of carbohydrate conjugates of proteins and lipids, CRC Crit. Rev. Biochem., 10:259-306:1981.
Ballas et al., Liposomes bearing a quaternary ammonium detergent as an efficient vehicle for functional transfer of TMV-RNA into plant protoplasts.
Bard et al., Peripherally administered antibodies against amyloid beta-peptide enter the central nervous system and reduce pathology in a mouse model of Alzheimer disease, Nat. Med., 6:916-919, 2000.
Barnes et al., Methods for growth of cultured cells in serum-free medium, Anal. Biochem., 102:255-270, 1980.

(Continued)

Primary Examiner — Daniel E Kolker
(74) Attorney, Agent, or Firm — Nisan A. Steinberg

(57) ABSTRACT

Compositions for treating neurodegenerative or amyloidgenic disorders such as Alzheimer's disease (AD) are provided. More particularly, humanized anti-amyloid-beta antibodies, compositions containing such antibodies, corresponding nucleic acids, vectors and host cells, and methods of making such antibodies are provided.

22 Claims, 4 Drawing Sheets

U.S. PATENT DOCUMENTS

| | | | |
|---|---|---|---|
| 6,790,610 B2 | 9/2004 | Gurney et al. | |
| 6,797,487 B2 | 9/2004 | Gurney et al. | |
| 6,818,448 B2 | 11/2004 | Mullan | |
| 6,852,482 B1 | 2/2005 | Chrysler et al. | |
| 6,864,290 B2 | 3/2005 | Schostarez et al. | |
| 7,033,812 B2 | 4/2006 | Zhong et al. | |
| 7,041,870 B2 | 5/2006 | Tomizuka et al. | |
| 7,087,399 B1 | 8/2006 | Zhong et al. | |
| 7,119,166 B2 | 10/2006 | Lin | |
| 7,153,491 B2 | 12/2006 | Zaczek et al. | |
| 7,169,901 B2 | 1/2007 | Baca et al. | |
| 7,179,892 B2 | 2/2007 | Basi et al. | |
| 7,183,390 B2 | 2/2007 | Vasquez et al. | |
| 7,241,873 B2 * | 7/2007 | Uede et al. | 530/387.3 |
| 7,244,708 B2 | 7/2007 | Tang et al. | |
| 7,256,273 B2 | 8/2007 | Basi et al. | |
| 7,320,790 B2 | 1/2008 | Hinton et al. | |
| 7,335,632 B2 | 2/2008 | Ghosh et al. | |
| 7,351,803 B2 | 4/2008 | Johnson et al. | |
| 7,538,258 B2 | 5/2009 | Mullan | |
| 7,732,399 B2 | 6/2010 | Goldenberg et al. | |
| 2002/0055459 A1 | 5/2002 | Chopra et al. | |
| 2002/0086847 A1 | 7/2002 | Chain | |
| 2002/0115600 A1 | 8/2002 | Koelsch et al. | |
| 2002/0157122 A1 | 10/2002 | Wong et al. | |
| 2003/0044772 A1 | 3/2003 | Watkins et al. | |
| 2003/0073655 A1 | 4/2003 | Chain | |
| 2003/0082191 A1 | 5/2003 | Poduslo et al. | |
| 2003/0082735 A1 | 5/2003 | McGrew et al. | |
| 2003/0092125 A1 | 5/2003 | Davis et al. | |
| 2003/0113316 A1 | 6/2003 | Kaisheva et al. | |
| 2004/0043418 A1 | 3/2004 | Holtzman et al. | |
| 2004/0132680 A1 | 7/2004 | Wong et al. | |
| 2004/0167075 A1 | 8/2004 | Tang et al. | |
| 2004/0171815 A1 | 9/2004 | Schenk et al. | |
| 2004/0171816 A1 | 9/2004 | Schenk et al. | |
| 2004/0220079 A1 | 11/2004 | Koelsch et al. | |
| 2004/0248232 A1 | 12/2004 | Hook | |
| 2004/0248766 A1 | 12/2004 | LeBlanc | |
| 2005/0019255 A1 | 1/2005 | Zaczek et al. | |
| 2006/0034848 A1 | 2/2006 | Kinoshita et al. | |
| 2006/0182684 A1 | 8/2006 | Beliveau | |
| 2006/0189515 A1 | 8/2006 | Beliveau et al. | |
| 2006/0198851 A1 | 9/2006 | Basi et al. | |
| 2006/0228349 A1 | 10/2006 | Acton et al. | |
| 2007/0099185 A1 | 5/2007 | Hagen et al. | |
| 2008/0021196 A1 | 1/2008 | Tang et al. | |

FOREIGN PATENT DOCUMENTS

| | | |
|---|---|---|
| EP | 0613007 A2 | 8/1994 |
| EP | 1431310 | 6/2004 |
| EP | 1129355 B1 | 7/2005 |
| EP | 1327143 B1 | 2/2007 |
| EP | 1255769 B1 | 5/2007 |
| WO | WO-87/00195 | 1/1987 |
| WO | WO-87/05330 | 9/1987 |
| WO | WO-90/03430 | 4/1990 |
| WO | WO-90/14363 | 5/1990 |
| WO | WO-91/00741 | 1/1991 |
| WO | WO-91/17271 | 11/1991 |
| WO | WO-92/01047 | 1/1992 |
| WO | WO-92/11018 | 7/1992 |
| WO | WO-93/11161 | 6/1993 |
| WO | WO-93/25673 | 12/1993 |
| WO | WO-94/02602 | 2/1994 |
| WO | 9625435 A1 | 8/1996 |
| WO | WO-96/32478 | 10/1996 |
| WO | WO-96/33735 | 10/1996 |
| WO | WO-96/34096 | 10/1996 |
| WO | 9640885 A2 | 12/1996 |
| WO | 9640885 A3 | 12/1996 |
| WO | WO-97/34631 | 9/1997 |
| WO | WO-98/24893 | 6/1998 |
| WO | 9844955 A1 | 10/1998 |
| WO | 9927944 A1 | 6/1999 |
| WO | 9927944 C2 | 6/1999 |
| WO | 9960024 C2 | 11/1999 |
| WO | 0017369 A2 | 3/2000 |
| WO | 0023576 A2 | 4/2000 |
| WO | WO-00/24782 | 5/2000 |
| WO | 0047618 A3 | 8/2000 |
| WO | 0123533 A2 | 4/2001 |
| WO | 0225276 A1 | 3/2002 |
| WO | 0246237 A2 | 6/2002 |
| WO | 02/088307 * | 11/2002 |
| WO | WO-02/088307 | 11/2002 |
| WO | 03016467 A2 | 2/2003 |
| WO | WO-03/020212 | 3/2003 |
| WO | 03/027151 * | 4/2003 |
| WO | 03070760 A2 | 8/2003 |
| WO | WO-2004/032868 | 4/2004 |
| WO | 2004060403 A2 | 7/2004 |
| WO | WO-2004/065423 | 8/2004 |
| WO | WO-2004/080419 | 9/2004 |
| WO | 2004084830 A2 | 10/2004 |
| WO | 2004108895 A2 | 12/2004 |
| WO | 2004108895 A3 | 12/2004 |
| WO | WO-2004/110369 | 12/2004 |
| WO | 2006/055178 * | 5/2006 |
| WO | 2006055178 A2 | 5/2006 |
| WO | 2006066089 A1 | 6/2006 |
| WO | 2006066171 A1 | 6/2006 |
| WO | 2006081171 A1 | 8/2006 |
| WO | 2007009229 A1 | 1/2007 |
| WO | 2007113172 A2 | 10/2007 |
| WO | 2007113172 A3 | 10/2007 |
| WO | 2008046228 A1 | 4/2008 |

OTHER PUBLICATIONS

Begley, Delivery of therapeutic agents to the central nervous system: the problems and the possibilities, Pharmacol. Ther, 104:29-45, 2004.

Behr et al., Efficient gene transfer into mammalian primary endocrine cells with lipopolyamine-coated DNA, PNAS USA, 86:6982-6986, 1989.

Behr, DNA strongly binds to micelles and vesicles containing lipopolyamines or lipointercalants, Tetrahedron Lett., 27:5861-5864, 1986.

Behr, Gene transfer with synthetic cationic amphiphiles: prospects for gene therapy, Bioconj. Chem., 5:382-389, 1994.

Better et al., *Escherichia coli* secretion of an active chimeric antibody fragment, Science, 240:1041-1043, 1988.

Bhatnagar et al., Structure-activity relationships of novel hematoregulatory peptides, J. Med. Chem., 39:3814-3819, 1996.

Boulianne et al., Production of functional chimaeric mouse/human antibody, Nature, 312:643-646, 1984.

Burton et al., Human antibodies from combinatorial libraries, Adv. Immunol., 57:191-280, 1994.

Caron et al., Engineered humanized dimeric forms of IgG are more effective antibodies, J. Exp. Med., 176:1191-1195, 1992.

Carpenter et al., Interactions of stabilizing additives with proteins during freeze-thawing and freeze-drying, Dev. Biol. Standardization, 74:225-239, 1991.

Carter et al., High level *Escherichia coli* expression and production of a bivalent humanized antibody fragment, Biotechnology, 10:163-167, 1992.

Caton et al., Influenza virus hemagglutinin-specific antibodies isolated from a combinatorial expression library are closely related to the immune response of the donor, PNAS USA, 87:6450-6454, 1990.

Chen, Formulation concern of protein drugs, Drug Dev. Indust. Pharm., 18:1311-1354, 1992.

Cherny et al., Treatment with a copper-zinc chelator markedly and rapidly inhibits beta-amyloid accumulation in Alzheimer's disease transgenic mice, Neuron, 30:665-666, 2001.

Chothia et al., Canonical structures for the hypervariable regions of immunoglobulins, J. Mol. Biol., 196:901-917, 1987.

Chung et al., Uptake, degradation, and release of fibrillar and soluble forms of Alzheimer's amyloid beta-peptide by microglial cells, J. Biol. Chem., 274:32301-32308, 1999.

Clackson et al., In vitro selection from protein and peptide libraries, Trends Biotechnol., 12:173-184, 1994.

Clackson et al., Making antibody fragments using phage display libraries, Nature, 352:624-628, 1991.

Co et al., A humanized antibody specific for the platelet integrin gpIIb/IIIa, J. Immunol., 152:2968-2976, 1994.

Cunningham et al., High-resolution epitope mapping of hGH-receptor interactions by alanine-scanning mutagenesis, Science, 244:1081-1085, 1989.

Cuthbertson et al., Design of low molecular weight hematoregulatory agents from the structure-activity relationship of a dimeric pentapeptide, J. Med. Chem., 40:2876-2882, 1997.

Davies et al., Affinity improvement of single antibody VH domains: residues in all three hypervariable regions affect antigen binding, Immunotechnology, 2:169-179, 1996.

Demattos et al., Peripheral anti-A beta antibody alters CNS and plasma A beta clearance and decreases brain A beta burden in a mouse model of Alzheimer's disease, PNAS USA, 98:8850-8855, 2001.

Doody, Therapeutic standards in Alzheimer disease, Alzheimer Dis. Assoc. Disord., 13:S20-S26, 1999.

Edge et al., Deglycosylation of glycoproteins by trifluoromethanesulfonic acid, Anal. Biochem., 118:131-137, 1981.

Evan et al., Isolation of monoclonal antibodies specific for human c-myc proto-oncogene product, Mol. Cell. Biol., 5:3610-3616, 1985.

Fassbender et al., Simvastatin strongly reduces levels of Alzheimer's disease β-amyloid peptides Aβ42 and Aβ40 in vitro and in vivo, PNAS, 98:5856-5861, 2000.

Felgner et al., Lipofection: a highly efficient, lipid-mediated DNA-transfection procedure, PNAS USA, 84:7413-7417, 1987.

Fermér et al., Specificity rescue and affinity maturation of a low-affinity IgM antibody against pro-gastrin-releasing peptide using phage display and DNA shuffline, Tumor Biol., 25:7-13, 2004.

Field et al., Purification of a RAS-responsive adenylyl cyclase complex from *Saccharomyces cerevisiae* by use of an epitope addition method, Mol. Cell. Biol., 8:2159-2165, 1988.

Friedmann, Progress toward human gene therapy, Science, 244:1275-1281, 1989.

Gervais et al., A low molecular weight GAG mimetic compound reduces brain amyloid burden in hAPP transgenic mice, 7th International Geneva/Springfield Symposium on Advances in Alzheimer Therapy, 2002.

Golde et al., Cholesterol modulation as an emerging strategy for the treatment of Alzheimer's disease, Drug Discov. Today, 6:1049-1055, 2001.

Graham et al., Characteristics of a human cell line transformed by DNA from human adenovirus type 5, J. Gen. Virol., 36:59-74, 1977.

Guss et al., EMBO J., 5:1567-1575, 1986.

Ham et al., Media and growth requirements, Methods Enzymol., 58:44-93, 1979.

Hardy et al., Amyloid deposition as the central event in the aetiology of Alzheimer's disease, Trends Pharmacol. Sci., 23:383-388, 1991.

Hollinger et al., "Diabodies": small bivalent and bispecific antibody fragments, PNAS USA, 90:6444-6448, 1993.

Holt et al., Domain antibodies: proteins for therapy, Trends Biotechnol., 21:484-490, 2003.

Hoogenboom et al., By-passing immunization: human antibodies from synthetic repertoires of germline VH gene segments rearranged in vitro, J. Mol. Biol., 227:381-388, 1991.

International Preliminary Report on Patentability, PCT/US2006/002259, International Bureau of WIPO, mailed Jul. 24, 2007.

International Search Report, PCT/US2006/002259, European Patent Office, mailed Apr. 7, 2006.

Ito et al., Synthetic cationic amphiphiles for liposome-mediated DNA transfection, Biochem. Int., 22:235-241, 1990.

Jermutus et al., Tailoring in vitro evolution for protein affinity or stability, PNAS USA, 98:75-80, 2001.

Jespers et al., Guiding the selection of human antibodies from phage display repertoires to a single epitope of an antigen, Biotechnology, 12:899-903, 1994.

Jick et al., Statins and the risk of dementia, Lancet, 356:1627-1631, 2000.

Joachim et al., The seminal role of β-amyloid in the pathogenesis of Alzheimer disease, Alzheimer Dis. Assoc. Disord., 6:7-34, 1992.

Jones et al., Replacing the complementarity-determining regions in a human antibody with those from a mouse, Nature, 321:522-525, 1986.

Kettleborough et al., Humanization of a mouse monoclonal antibody by CDR-grafting: the importance of framework residues on loop conformation, Protein Eng., 4:773-783, 1991.

Kilpatrick et al., Rapid development of affinity matured monoclonal antibodies using RIMMS, Hybridoma, 16:381-389, 1997.

Kirschner et al., Synthetic peptide homologous to beta protein from Alzheimer disease forms amyloid-like fibrils in vitro, PNAS USA, 84:6953-6957, 1987.

Köhler et al., Continuous cultures of fused cells secreting antibody of predefined specificity, Nature, 256:495-497, 1975.

Kozbor, A human hybrid myeloma for production of human monoclonal antibodies, J. Immunol., 133:3001-3005, 1984.

Letsinger, Cholesteryl-conjugated oligonucleotides: synthesis, properties, and activity as inhibitors of replication of human immunodeficiency virus in cell culture, PNAS USA, 86:6553-6556, 1989.

Leventis et al., Interactions of mammalian cells with lipid dispersions containing novel metabolizable cationic amphiphiles, Biochem. Biophys. Acta, 1023:124-132, 1990.

Lindmark et al., Binding of immunoglobulins to protein A and immunoglobulin levels in mammalian sera, J. Immunol. Methods, 62:1-13, 1983.

Lowman, Bacteriophage display and discovery of peptide leads for drug development, Ann. Rev. Biophys. Biomol. Struct., 26:401-424, 1997.

Malone et al., Cationic liposome-mediated RNA transfection, PNAS USA, 86:6077-6081, 1989.

Marks et al., By-passing immunization: human antibodies from V-gene libraries displayed on phage, J. Mol. Biol., 222:581-597, 1991.

Mather et al., Culture of testicular cells in hormone-supplemented serum-free medium, Ann. N.Y. Acad. Sci., 383:44-68, 1982.

Mather, Establishment and characterization of two distinct mouse testicular epithelial cell lines, Biol. Reprod, 23:243-251, 1980.

McGeer et al., Inflammation, autotoxicity and Alzheimer disease, Neurobiol. Aging, 22:799-809, 2001.

Miller, Human gene therapy comes of age, Nature, 357:455-460, 1992.

Misra et al., Drug delivery to the central nervous system: a review, J. Pharm. Pharmaceut. Sci., 6:252-273, 2003.

Morrison et al., Chimeric human antibody molecules: mouse antigen-binding domains with human constant region domains, PNAS USA, 81:6851-6855, 1984.

Morrison et al., Genetically engineered antibody molecules, Adv. Immunol., 44:65-92, 1988.

Ohmori et al., The enhancing effect of anionic alpha-helical peptide on cationic peptide-mediating transfection systems, Biochem. Biophys. Res. Commun., 235:726-729, 1997.

Paborsky et al., Mammalian cell transient expression of tissue factor for the production of antigen, Protein Eng., 3:547-553, 1990.

Padlan, A possible procedure for reducing the immunogenicity of antibody variable domains while preserving their ligand-binding properties, Molec. Immunol., 28:489-498, 1991.

Padlan, Anatomy of the antibody molecule, Molec. Immunol., 31:169-217, 1994.

Pan et al., Efficient transfer of receptor-associated protein (RAP) across the blood-brain barrier, J. Cell Sci., 117:5071-5078, 2004.

Pan et al., Why study transport of peptides and proteins at the neurovascular interface?, Brain Res. Rev., 46:32-43, 2004.

Parasce et al., Slow degradation of aggregates of the Alzheimer's disease amyloid beta—protein by microglial cells, J. Biol. Chem., 272:29390-29397, 1997.

Park et al., Metabolic impairment induces oxidative stress, compromises inflammatory responses, and inactivates a key mitochondrial enzyme in microglia, J. Neurochem., 72:1948-1958, 1999.

Pinnaduwage et al., Use of a quaternary ammonium detergent in liposome mediated DNA transfection of mouse L-cells, Biochim. Biophys. Acta, 985:33-37, 1989.

Poduslo et al., Amyloid β peptide as a vaccine for Alzheimer's disease involves receptor-mediated transport at the blood-brain barrier, Clin. Neurosci., 12:3197-3200, 2001.
Poduslo et al., Design and chemical synthesis of a magnetic resonance contrast agent with enhanced in vitro binding, high blood-brain barrier permeability, and in vivo targeting to Alzheimer's disease amyloid plaques, Biochem., 43:6064-6075, 2004.
Pollard et al., Polyethylenimine but not cationic lipids promotes transgene delivery to the nucleus in mammalian cells, J. Biol. Chem., 273:7507-7511, 1998.
Riechmann et al., Reshaping human antibodies for therapy, Nature, 332:323-327, 1988.
Rose et al., A new cationic liposome reagent mediating nearly quantitative transfection of animal cells, Biotechniques, 10:520-525, 1991.
Sanger et al., DNA sequencing with chain-terminating inhibitors, PNAS USA, 74:5463-5467, 1977.
Sarmay et al., Mapping and comparison of the interaction sites on the Fc region of IgG responsible for triggering antibody dependent cellular cytotoxicity (ADCC) through different types of human Fc gamma receptor, Molec. Immunol., 29:633-639, 1992.
Schenk et al., Current progress in beta-amyloid immunotherapy, Curr. Opin. Immunol., 16:599-606, 2004.
Schenk et al., Immunization with amyloid-β attenuates Alzheimer-disease-like pathology in the PDAPP mouse, Nature, 400:173-177, 1999.
Selkoe, Translating cell biology into therapeutic advances in Alzheimer's disease, Nature, 399:A23-A31, 1999.
Shields et al., High resolution mapping of the binding site on human IgG1 for Fc gamma RI, Fc gamma RII, Fc gamma RIII, and FcRn and design of IgG1 variants with improved binding to the Fc gamma R, J. Biol. Chem., 276:6591-6604, 2001.
Shopes, A genetically engineered human IgG mutant with enhanced cytolytic activity, J. Immunol., 148:2918-2922, 1992.
Sinha et al., Purification and cloning of amyloid precursor protein beta-secretase from human brain, Nature, 402:537-540, 1999.
Skerra et al., Assembly of a functional immunoglobulin Fv fragment in *Escherichia coli*, Science, 240:1038-1041, 1988.
Sojar et al., A chemical method for the deglycosylation of proteins, Arch. Biochem. Biophys., 259:52-57, 1987.
Soto et al., β-Sheet breaker peptides for the treatment of amyloidosis in Alzheimer disease, 7th International Geneva/Springfield Symposium on Advances in Alzheimer Therapy, 2002.
Steinberg, Testing potential Alzheimer vaccines, The Scientist, 16:22-23, 2002.
Stevenson et al., A chimeric antibody with dual Fc regions (bisFabFc) prepared by manipulations at the IgG hinge, Anti-cancer Drug Design, 3:219-230, 1989.
Studnicka et al., Human-engineered monoclonal antibodies retain full specific binding activity by preserving non-CDR complementarity-modulating residues, Protein Eng., 7:805-814, 1994.
Thotakura et al., Enzymatic deglycosylation of glycoproteins, Methods Enzymol., 138:350-359, 1987.
Urlaub et al., Isolation of Chinese hamster cell mutants deficient in dihydrofolate reductase activity, PNAS USA, 77:4216-4220, 1980.
Verhoeyer et al., Reshaping human antibodies: grafting an antilysozyme activity, Science, 239:1534-1536, 1988.
Verma, Gene therapy, Sci. Am., 263:68-84, 1990.
Vinters, Cerebral amyloid angiopathy: a critical review, Stroke, 18:311-324, 1987.
Watkins, Screening of phage-expressed antibody libraries by capture lift, Methods Molec. Biol., 178:187-193, 2002.
Williams et al., The lyophilization of pharmaceuticals: a literature review, J. Parenter. Sci. Tech., 38:48-59, 1984.
Winter et al., Making antibodies by phage display technology, Annu. Rev. Immunol., 12:433-455, 1994.
Wolff et al., Monoclonal antibody homodimers: enhanced antitumor activity in nude mice, Cancer Res., 53:2560-2565, 1993.
Wolozin et al., Decreased prevalence of Alzheimer disease associated with 3-hydroxy-3-methyglutaryl coenzyme A reductase inhibitors, Arch. Neurol., 57:1439-1443, 2000.
Written Opinion of the International Searching Authority, PCT/US2006/002259, European Patent Office, mailed Apr. 7, 2006.
Yan et al., Immunocytochemical localization of TrkB in the central nervous system of the adult rat., J. Comp. Neurol., 378:135-157, 1997.
Younkin, The role of A beta 42 in Alzheimer's disease, J. Physiol., 92:289-292, 1998.
Zapata et al., Engineering linear F(ab')2 fragments for efficient production in *Escherichia coli* and enhanced antiproliferative activity, Protein Eng., 8:1057-1062, 1995.
Zhou et al., Lipophilic polylysines mediate efficient DNA transfection in mammalian cells, Biochim. Biophys. Acta, 1065:8-14, 1991.
U.S. Appl. No. 60/474,654, filed May 30, 2003, Basi, Guriq.
U.S. Appl. No. 60/621,776, filed Oct. 25, 2004, Lambert et al.
U.S. Appl. No. 60/636,776, filed Dec. 15, 2004, Basi et al.
U.S. Appl. No. 60/646,658, filed Jan. 24, 2005, Shen et al.
U.S. Appl. No. 60/652,538, filed Feb. 14, 2005, Shughrue et al.
Banks, William A., "Are the Extracelluar Pathways a Conduit for the Delivery of Therapeutics to the Brain?", Current Pharmaceutical Design, 10: 1365-1370 (2004).
Golde, Todd E., Alzheimer disease therapy: Can the amyloid cascade be halted?, The Journal of Clinical Investigation, 111 (1): 11-18 (2003).
Kowall et al., "An in vivo model for the neurodegenerative effects of Beta amyloid and protection by substance P", Proc. Natl. Acad. Sci. USA, 88: 7247-7251 (1991).
Lichtlen et al., "Antibody-based approaches in Alzheimer's research: safety, pharmacokinetics, metabolism, and analytical tools", Journal of Neurochemistry, 104: 859-874 (2008).
Sisodia et al., "A role for the Beta-amyloid precursor protein in memory?", Proc Natl. Acad. Sci. USA, 95: 12074-12076 (1998).

* cited by examiner

|  | FR1 | CDR1 | FR2 | CDR2 | FR3 |
|---|---|---|---|---|---|
| MURINE 2.1 | QVTLKESGPGILKPSQTLSLTCSFSGFSLR | TSGMGVG | WIRQPSGKGLEWLA | HIWWDDDKSYNPSLKS | QLTISKDTSRNQVFLKITSVDTADTATYYCARR |
| 2.1 HC X | .....ALV..T...T....R | ....... | ....P..A..... | ................ | Q......K..V.TM.NM.PV........R |
| 2.1 HC Y | ..R..ALV..T...T....R | ....... | ....P..A..... | ................ | Q......K..V.TM.NM.PV........R |
| 2.1 HC Z | .....ALV..T...T....R | ....... | ....P..G..... | ................ | Q......K..VLTM.NM.PV........R |
| VH2-70 | QVTLRESGPALVKPTQTLTLTCTFSGFSLS | | WIRQPPGKALEWLA | | RLTISKDTSKNQVVLTMTNMDPVDTATYYCARI |

|  | CDR3 | FR4 |
|---|---|---|
| MURINE 2.1 | NYYYDDYFAY | WGQGTTLTVSS |
| 2.1 HC X | .........  | .....LV.... |
| 2.1 HC Y | .........  | .....LV.... |
| 2.1 HC Z | .........  | .....TL.... |
| JH1 |  | WGQGTLVTVSS |

Fig. 1A

|  | FR1 | CDR1 | FR2 | CDR2 | FR3 | CDR3 |
|---|---|---|---|---|---|---|
| MURINE 2.1 | DVLMTQTPLSLPVSLGDQASISC | RSSQSIVHSNGNTYLE | WYLQKPGQSPKLLIY | KVSNRFS | GVPDRFSGSGSGTDFTLKISRVEAEDLGVYYC | FQGSHVPLT |
| 2.1 LC A | .VL...S......TL.QP..... | ................ | .YL.R......KL... | ....... | ................................ | ......... |
| 2.1 LC B | .VV...S......TL.QP..... | ................ | .FV.R......RV... | ....... | ..............................V. | ......... |
| 2.1 LC C | .VV...S......TL.QP..... | ................ | .YL.R......QL... | ....... | ..............................V. | ......... |
| 2.1 LC D | .VV...S......TL.QP..... | ................ | .YL.R......QL... | ....... | ..............................V. | ......... |
| 2.1 LC E | .VV...S......TL.QP..... | ................ | .YL.R......RL... | ....... | ..............................V. | ......... |
| 2.1 LC F | .IV...S......TP.EP..... | ................ | .YL.R......QL... | ....... | ..............................V. | ......... |
| 2.1 LC G | .IV...S......TP.EP..... | ................ | .YL.K......RL... | ....... | ..............................V. | ......... |
| 2.1 LC I | .IV...S......TP.EP..... | ................ | .YL.K......QL... | ....... | ..............................V. | ......... |
| 2.1 LC J | .VV...S......TL.QP..... | ................ | .FQ.R......RR... | ....... | ..............................V. | ......... |
| A19 | DIVMTQSPLSLPVTPGEPASISC | ................ | WYLQKPGQSPQLLIY | | GVPDRFSGSGSGTDFTLKISRVEAEDVGVYYC | |

|  | FR4 |
|---|---|
| MURINE 2.1 | FGAGTKLELK |
| 2.1 LC A | ..A.....I. |
| 2.1 LC B | ..G...L.I. |
| 2.1 LC C | ..Q...L.I. |
| 2.1 LC D | ..G...V.I. |
| 2.1 LC E | ..G...V.I. |
| 2.1 LC F | ..G...V.I. |
| 2.1 LC G | ..G...V.I. |
| 2.1 LC I | ..G...V.I. |
| 2.1 LC J | ..Q.....I. |
| JK4 | FGGGTKVEIK |

Fig. 1B

Study 6: Aß IHC of Tg 2576 Mice
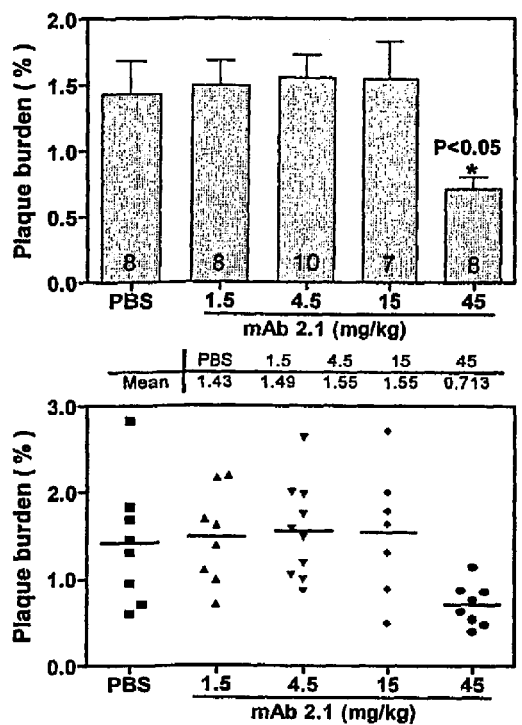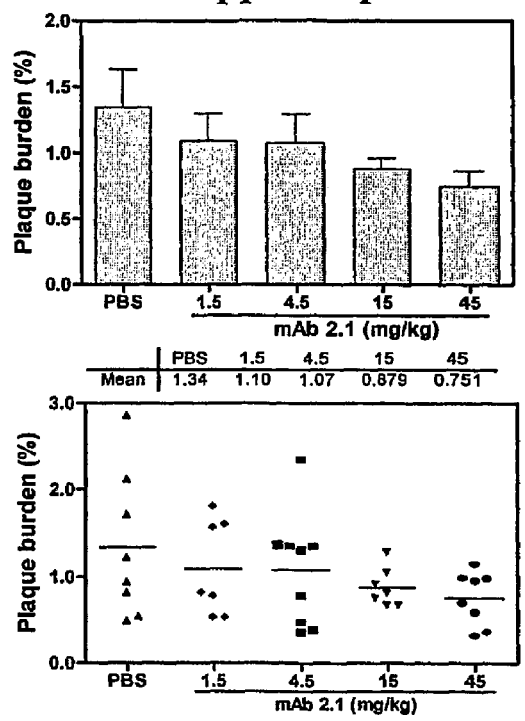
Fig. 2

HUMANIZED ANTI-AMYLOID ANTIBODY

The instant application contains an ASCII "txt" compliant sequence listing submitted via EFS-WEB on Sep. 15, 2010, which serves as both the computer readable form (CRF) and the paper copy required by 37 C.F.R. Section 1.821(c) and 1.821(e), and is hereby incorporated by reference in its entirety. The name of the "txt" file created on Sep. 2, 2010, is: A-967-US-PCT-dtd090210-52Seqs_ST25.txt, and is 83 kb in size.

TECHNICAL FIELD

This invention relates to compositions for treating neurodegenerative or amyloidogenic disorders such as Alzheimer's disease (AD), and more particularly, to compositions containing humanized anti-amyloid-beta antibodies.

BACKGROUND OF THE INVENTION

Alzheimer's disease (AD) affects more than 12 million patients worldwide, accounting for most dementia diagnosed after the age of 60. The disease is clinically characterized by a global decline of cognitive function that progresses slowly and leaves end-stage patients bedridden, incontinent and dependent on custodial care; death occurs, on average, nine years after diagnosis (Davis et al., in Pharmacological Management of Neurological and Psychiatric Disorders, pp. 267-316, 1998). In addition to its direct effects on patients, advanced AD puts a tremendous burden on family caregivers and causes high nursing home costs for society. Age is the major risk factor for AD, and a health care crisis is likely in countries with aging populations if treatments that protect against the disease or delay or stop its progression cannot be introduced within the next decade. The current standard of care for mild to moderate AD includes treatment with acetylcholine-esterase inhibitors to improve cognitive function (Doody, R., Alzheimer Dis. Assoc. Disord., 13:S20-S26, 1999). These drugs are safe, but of limited benefit to most patients. Other drugs are used to manage mood disorder, agitation and psychosis, but no treatment with a strong disease modifying effect is currently available.

Much of AD research has been focused on the amyloid cascade which predicts that Aβ, a proteolytic derivative of the large transmembrane protein APP, has an early and critical role in all cases of AD. Aβ forms aggregates that are thought to initiate a pathogenic cascade ultimately leading to neuronal loss and dementia (Hardy et al., Trends Pharmacol., 23:383-288, 1991). The amyloid cascade hypothesis was originally formulated based on pathological evidence. Two pathological hallmarks of AD are extracellular amyloid plaques, predominantly of Aβ42, and intraneuronal tangles of an aggregated form of the neuronal protein tau. Amyloid plaques are relatively specific for AD, whereas tangles are also found in other disorders (Joachim et al., Alzheimer Dis. Assoc. Disord., 6:7-34, 1992). Genetic analysis of the rare, familial autosomal-dominant AD with early onset has led to the identification of disease-causing mutations in three genes: amyloid precursor protein (APP), presenilin1 (PS1) and presenilin2 (PS2). The only common effect of all these mutations is an increased production of Aβ42, which is therefore assumed to cause disease pathogenesis (Younkin, S., J. Physiol., 92:289-292, 1998; Selkoe, D., Nature, 399:A23-A31, 1999). In contrast, the cause for the more common, sporadic, late-onset AD remains unknown. Based on the similarities in pathology (in particular, the massive Aβ42 accumulation) and clinical presentation of familial and sporadic AD, it is widely accepted that Aβ42 is critical in both.

The amyloid cascade is initiated when Aβ42 is proteolytically generated from APP by the sequential action of two proteases, β-secretase and γ-secretase. Because Aβ42 generation is the first step in the cascade, shutting down or reducing its production is desirable. Beginning in 1992, some companies initiated cell-based screens for inhibitors that are reported to have provided potent γ-, but not β-secretase inhibitors. In 2001, Bristol-Myers-Squibb announced that the first of these γ-secretase inhibitor compounds had moved into phase 2 clinical trials (P. Molinoff et al., Symposium on Molecular Mechanisms and Therapeutic Strategies for Neurodegenerative Diseases, Shanghai, 2001). The results of trials have not yet been released. The status of the cell-based γ-secretase inhibitor programs at most other companies has not been disclosed. β-secretase has been identified and its structure has been solved (Citron, M., Nature, 5:1055-1057, 2002). Peptidic β-secretase inhibitors have been featured in several publications (Sinha et al., Nature, 402:537-540, 1999).

There are numerous targets for therapeutic intervention of the amyloid cascade downstream of Aβ generation. On theoretical grounds, anti-aggregation approaches are very attractive-whereas Aβ generation is a physiological event, aggregation of monomeric Aβ into oligomers and fibrils with β-sheet structure is considered pathogenic. Small-molecule inhibitors of the interaction between Aβ and glycosaminoglycans, which is proposed to be involved in the formation of amyloid deposits in Alzheimer's disease, have been reported, and in vivo efficacy of these compounds has been demonstrated in amyloid mice. (F. Gervais et at., 7th International Geneva/Springfield Symposium on Advances in Alzheimer Therapy, 2002). Short peptidic Aβ derivatives, have also been reported to show in vivo efficacy upon intraperitoneal injection in the amyloid mouse (C. Soto et al., 7th International Geneva/Springfield Symposium on Advances in Alzheimer Therapy, 2002). Chelating zinc (reported to be critical for Aβ aggregation) with the antibiotic clioquinol has been reported to lower amyloid burden in vivo (Cherny et al., Neuron, 30:665-66, 2001; Bush et al., PNAS, 98:8850-8855, 2001).

Another approach to AD treatment involves immunotherapy. Amyloid mice vaccinated with fibrillar Aβ42 were reported to have reduced plaque pathology (Schenk et al., Nature, 400:173-177, 1999). The vaccination effect could be mimicked by peripheral administration of anti-Aβ antibodies that bind plaques. It was proposed that small quantities of peripherally administered anti-Aβ antibodies cross into the brain, where they label amyloid plaques and activate surrounding microglia to phagocytose and thus clear Aβ deposits. This mechanism was modeled in an ex vivo assay, in which cultured microglia clear Aβ deposits from sections of AD brains upon addition of anti-Aβ antibodies; this assay predicted in vivo efficacy in the mouse model (Bard et al., Nat. Med., 6:916-919, 2000). An alternative mechanism of action suggests that certain Aβ antibodies act primarily as a peripheral sink, essentially pulling soluble Aβ peptide from the brain into the periphery, where it is cleared (DeMattos et al., PNAS, 98:8850-8855, 2001). Regardless of the exact mechanism, it seems that antibodies to Aβ are efficacious at reducing plaque burden in transgenic mouse models. Based on these findings, Elan Corporation, in collaboration with Wyeth, moved into clinical trials with an Aβ vaccination approach. The trials were stopped in phase 2A when six percent of patients developed meningo-encephalitis (Steinberg, D., The Scientist, 16:22-23, 2002).

Of interest are U.S. Pat. No. 6,787,637 and U.S. Application Publication Nos. 2004/0171815 and 2004/0171816, which disclose the use of anti-amyloid antibodies and humanized anti-amyloid antibodies, in the treatment of Alzheimer's disease. The anti-amyloid antibodies disclosed in these publications were introduced into mice to evaluate their ability to reduce Aβ levels and were also tested for their ability to induce phagocytosis.

Retrospective epidemiological studies suggest that non-steroidal anti-inflammatory drugs (NSAIDs) (drugs such as aspirin, which, among other actions, inhibit the cyclo-oxygenase cox-2) provide some degree of protection from AD. It is proposed that at least part of the AD phenotype is due to chronic brain inflammation (McGeer et al., *Neurobiol Aging*, 22:799-809, 2001). A small trial of indomethacin hinted at an improvement, but large placebo-controlled trials of specific COX2 inhibitors in AD have not been successful, implying that inhibition of this target does not change the disease course (Citron, M., Nat. Rev. Neurosci., 5:677-685, 2004). Epidemiological studies also suggest that treatment with statins, inhibitors of the cholesterol-synthesizing enzyme HMG-CoA-reductase, also protects from Alzheimer's disease (Wolozin et al., *Arch. Neurol.*, 57:1439-1443, 2000; Jick et al., *Lancet*, 356:1627-1631, 2000). The mechanism may be through direct effects on Aβ42 production (Fassbender et al., *PNAS*, 98:5856-5861, 2000), although microvascular and endothelial effects of the statins and other indirect mechanisms cannot be excluded (Golde et al., *Drug Discov. Today*, 6:1049-1055, 2001).

There continues to exist the need for new therapies and reagents for the treatment of Alzheimer's disease, in particular, therapies and reagents capable of effecting a therapeutic benefit without significant adverse effects.

SUMMARY OF THE INVENTION

The materials and methods of the present invention fulfill the aforementioned and other related needs in the art.

The invention provides specific binding agents, such as human or humanized (non-murine) monoclonal antibodies that bind amyloid-beta. In one embodiment, such agents comprise an amino acid sequence that is at least 80%, 90% or 100% identical to the amino acid sequence set forth in SEQ ID NO: 11. Such agents may further comprise the amino acid sequence set forth in SEQ ID NO: 10. Any of the preceding specific binding agents may further comprise the amino acid sequence set forth in SEQ ID NO: 9.

In a related embodiment, the aforementioned specific binding agent comprises any one, two or all three of the amino acid sequences set forth in SEQ ID NOs 12, 13 or 14.

In another related embodiment, any of the aforementioned agents comprise an amino acid sequence that is at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or more identical to the amino acid sequence set forth in SEQ ID NO: 6. In another embodiment of the invention, any of the aforementioned agents comprise an amino acid sequence that is at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or more identical to the amino acid sequence set forth in SEQ ID NO: 8. In such embodiments, the sequence variation relative to SEQ ID NOs: 6 or 8, respectively, may represent, for example, a conservative substitution of the corresponding amino acid in SEQ ID NO: 6 or 8 or a choice of an alternative human amino acid at that position.

In exemplary embodiments, the antibody or specific binding agent that binds amyloid-beta comprises the amino acid sequence set forth in SEQ ID NO: 6, and the amino acid sequence set forth in SEQ ID NO: 8.

In other exemplary embodiments, the antibody or specific binding agent that binds amyloid-beta comprises an amino sequence that is 85% or more identical to the amino acid sequence set forth in SEQ ID NO: 8. In other exemplary embodiments, the antibody or specific binding agent that binds amyloid-beta comprises an amino sequence that is 95% or more identical to the amino acid sequence set forth in SEQ ID NO: 6.

Any of the aforementioned antibodies may be, e.g., an IgG antibody (for example of the IgG1 or IgG3 subtype, or any other IgG subtype). Preferably the aforementioned antibodies exhibit an avidity characterized by a $k_d$ of lower than $10^{-2}$, or lower than $10^{-3}$, or $10^{-4}$, $10^{-5}$, $10^{-6}$, $10^{-7}$, $10^{-8}$, $10^{-9}$, as determined by surface plasmon resonance (BIAcore analysis).

In another embodiment, human or humanized (non-murine) monoclonal antibody that bind amyloid-beta is provided that comprises the amino acids sequences set forth in SEQ ID NOs 12, 13 and 14.

The invention also provides nucleic acids encoding any of the preceding antibodies or specific binding agents. In a related embodiment of the invention, a vector comprising any of the aforementioned nucleic acid sequences is provided. In still another embodiment, a host cell is provided comprising any of the aforementioned nucleic acids or vectors.

Numerous methods are contemplated in the present invention. For example, a method of producing an aforementioned antibody or specific binding agent is provided comprising culturing the aforementioned host cell such that the nucleic acid is expressed to produce the antibody or agent. Such methods may also comprise the step of recovering the antibody or agent from the host cell culture. In a related embodiment, an isolated antibody or agent produced by the aforementioned method is provided.

The invention further provides methods of using any of the preceding antibodies or specific binding agents, for example, to treat or prevent a neurodegenerative or CNS disorder associated with amyloid-beta by administering an effective amount thereof, or to treat or prevent an amyloidgenic disease by administering an effective amount thereof.

BRIEF DESCRIPTION OF THE DRAWINGS

FIG. 1A depicts alignments of the amino acid sequences of the variable regions of heavy chain of murine 2.1 (SEQ ID NO: 37) and various humanized versions thereof, as compared to a highly homologous human heavy chain sequence ("VH2-70/JH1", SEQ ID NO: 41). Humanized versions: 2.1 HC X (SEQ ID NO: 38); 2.1 HC Y (SEQ ID NO: 39); and 2.1 HC Z (SEQ ID NO: 40).

FIG. 1B depicts alignments of the amino acid sequences of the variable regions of the light chain of murine 2.1 (SEQ ID NO: 42) and various humanized versions thereof, as compared to a highly homologous human light chain sequence (VKII A19/JK4 ["A19/JK4"], SEQ ID NO: 52). Humanized versions: 2.1 LC A (SEQ ID NO: 43); 2.1 LC B (SEQ ID NO: 44); 2.1 LC C (SEQ ID NO: 45); 2.1 LC D (SEQ ID NO: 46); 2.1 LC E (SEQ ID NO: 47); 2.1 LC F (SEQ ID NO: 48); 2.1 LC G (SEQ ID NO: 49); 2.1 LC I (SEQ ID NO: 50); and 2.1 LC J (SEQ ID NO: 51).

FIG. 2 illustrates quantitative morphological analysis of the plaque burden in cingulate cortex after treatment (1× per week) with mAb 2.1 IgG.

DETAILED DESCRIPTION

Figure 3:
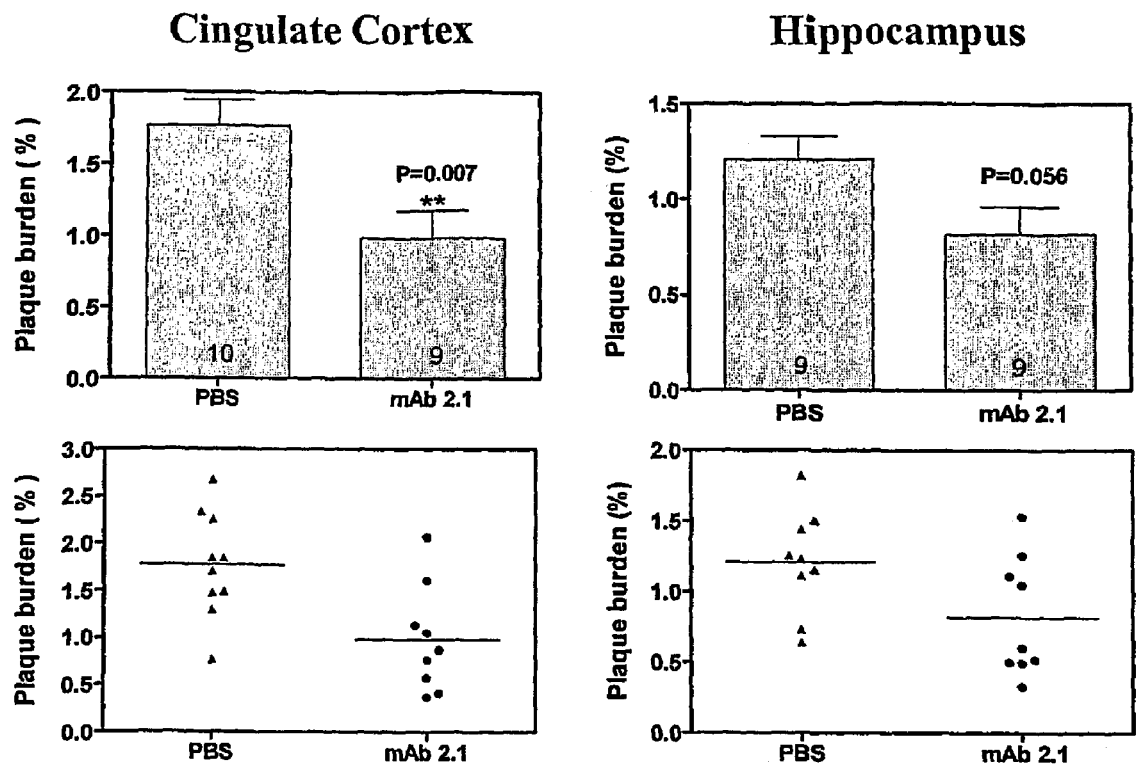
FIG. 3 illustrates quantitative morphological analysis of the plaque burden in cingulate cortex after treatment (3× per week) with mAb 2.1 IgG.

Deposits of aggregated amyloid β-peptide (Aβ) in parenchymal amyloid plaques are a defining criterion of Alzheimer's disease (AD) pathology, and Aβ aggregates (soluble or insoluble, oligomeric or fibrillar) are thought to trigger a pathogenic cascade resulting in the pathologic and clinical manifestations of AD. The primary component of amyloid plaques is a fibrillar aggregate comprising a 40 or 42 amino acid version of Aβ. Amyloid fibrils prepared in vitro from synthetic Aβ are morphologically indistinguishable from amyloid fibrils extracted from AD brain tissue (Kirschner et al., 1987). A number of antibody candidates prepared against the 40 or 42 amino acid version of Aβ were evaluated for their ability to bind to in vitro prepared Aβ40 and Aβ42 fibrils.

A murine anti-amyloid-beta (anti-Aβ) antibody designated antibody 2.1 was discovered to have markedly better effects than other antibodies on reducing the amyloid plaques in APP transgenic Tg2576 mice overexpressing human Aβ, a standard model of Alzheimer's disease. Chimeric and humanized versions of this antibody, modified to be less immunogenic in humans, were tested and shown to retain similar binding affinity for amyloid-β in in vitro assays. These chimeric and humanized versions that retained binding affinity were able to recognize native amyloid plaques in sections of murine and human brain, and also retained a similar ability to promote phagocytosis of amyloid deposits ex vivo.

The nucleotide and amino acid sequences of the light chain of murine antibody 2.1 are set forth in SEQ ID NOS: 1 and 2. The nucleotide and amino acid sequences of the heavy chain of murine antibody 2.1 are set forth in SEQ ID NOS: 3 and 4.

In one embodiment, the humanized antibody comprises a light chain that retains the original murine CDRs of murine antibody 2.1, positions 24-34, 50-56 and 89-97 of SEQ ID NO: 2, and has the human framework of VKII A19/JK4 (2.1 LC I).

Other human, human germline, or human consensus frameworks are suitable, such as VKII A1, VKII A2, VKII A3, VKII A17, VKII A18, VKII A23, VKII O1, VKII O11, or VKIV B3. Human, human germline, or human consensus joining region frameworks which are preferred include JK2 and JK4 whereas JK1, JK3 or JK5 may be suitable. Any other human, human germline, or human consensus frameworks such as those in the VKI or VKIII families may also be suitable. Analysis of the individual frameworks in the VKII family indicates that all members have at least 5 differences from the murine sequence in framework 1. The VKII family members with the least mismatches in framework 1 do not necessarily have the least mismatches in frameworks 2 or 3. As such the frameworks which combine to provide the least number of differences may be used as the template for humanization.

In other embodiments the humanized antibody comprises a light chain that retains the original murine CDRs of murine antibody 2.1, and has the human framework of VKII A19/JK2 except that murine amino acids are retained as follows: Leu at position 3, Lys at position 45, and Ala at position 100 (with all positions noted according to Kabat numbering). None of these residues are critical for binding to the antigen as shown by substitution of these residues with human residues (Val at position 3, Gln or Arg at position 45, and Gly or Gln at position 100). Those framework residues in the humanized antibody 2.1 LC A that are different from the VKII A19 framework, which has the least mismatches in frameworks 2 and 3, are present in other VKII human frameworks.

Residues at positions 2, 15, 17, 36, 37, 39, 45, 46, 100, and 104 were mutated in 2.1 LC B, 2.1 LC C, 2.1 LC D, 2.1 LC E, 2.1 LC F, 2.1 LC G, 2.1 LC I and 2.1 LC J to assess their contribution to the affinity of the antibody to antigen.

Amino acids at positions 36, 37 and 46 may be important to maintaining high binding activity; substitutions at any or all these positions may affect activity. In certain positions such as 2, 3, 15, 17, 39, 45, 100, 104, residues can be substituted with other human framework residues (such as with VK2 or other kappa families) or with 2.1 murine framework residues and still maintain their binding activity.

Thus, a wide variety of substitutions were made throughout the light chain and shown not to significantly affect binding affinity, with the exception of the mutations in the "humanized" light chain. Variants with further substitutions (e.g. conservative substitutions of the murine amino acids) may also retain the high binding affinity. As discussed in detail below, substitutions, deletions or insertions in positions within the CDRs and framework may be made without affecting affinity.

In some embodiments the humanized antibody comprises a heavy chain that retains the original murine CDRs of murine antibody 2.1, and has the human variable framework of VH 2-70 except that murine amino acids are retained at positions 5, 30 and 66. The Arg residue at position 94 is present in human framework VH2-05 (2.1HC X).

In other embodiments the humanized antibody comprises a heavy chain that retains the original murine CDRs of murine antibody 2.1, and has the human variable framework of VH 2-70 except that murine amino acids are retained at positions 30, 44, 66, 108 and 109 ("2.1 HC Y").

In other embodiments the humanized antibody comprises a heavy chain that retains the original murine CDRs of murine antibody 2.1, and has the human variable framework of VH 2-70 except that murine amino acids are retained at positions 5, 30, 44, 66, 108 and 109 ("2.1HC Z").

The presence of murine amino acids at positions 44 (G), 108 (T) and 109 (L) in the heavy chain ("2.1 HC Z") appeared to significantly reduce binding affinity relative to the presence of human amino acids at these positions. Variants with alternative substitutions (e.g. conservative substitutions of the human amino acids) may retain the desired binding affinity. As discussed in detail below, substitutions, deletions or insertions in other positions within the CDRs and framework may be made without affecting affinity. For example, substitutions to human framework residues at positions 30, 66, and 94 in the framework could be made without affecting affinity.

Nucleic acids encoding these modified light chain variable regions were constructed and co-expressed with nucleic acids encoding a CDR-grafted or a humanized heavy chain and vice versa, and optionally may be linked to constant regions. Any humanized or chimeric heavy chain and light chains may be combined as long as suitable binding affinity is maintained. The desired genes were introduced into mammalian cells and the resultant recombinant immunoglobulin products were expressed, purified and characterized.

The term "amyloidogenic disease" includes any disease associated with (or caused by) the formation or deposition of insoluble amyloid fibrils. Exemplary amyloidogenic disease include, but are not limited to Alzheimer's disease (AD), mild cognitive impairment, Parkinson's Disease with dementia, Down's Syndrome, Diffuse Lewy Body (DLB) disease, Cerebral Amyloid Angiopathy (CAA), vascular dementia and mixed dementia (vascular dementia and AD). Different amyloidogenic diseases are defined or characterized by the nature of the polypeptide component of the fibrils deposited. For example, in subjects or patients having Alzheimer's disease, β-amyloid protein (e.g., wild-type, variant, or truncated β-amyloid protein) is the characterizing polypeptide component of the amyloid deposit.

"Treatment" is an intervention performed with the intention of preventing the development or altering the pathology of a disorder. Accordingly, "treatment" refers to both therapeutic treatment and prophylactic or preventative measures. Those in need of treatment include those already with the disorder as well as those in which the disorder is to be prevented.

"Mammal" for purposes of treatment refers to any animal classified as a mammal, including humans, domestic and farm animals, and zoo, sports, or pet animals, such as dogs; horses, cats, cows, etc. Preferably, the mammal is human.

As used herein, the phrase "therapeutically effective amount" is meant to refer to an amount of therapeutic or prophylactic Aβ antibody that provides a reduction in the number, size or complexity of amyloid plaques or their precursors (oligomeric or protofibrils) in brain, or that provides a reduction in the severity or progression of symptoms associated with disease (i.e. that provides "therapeutic efficacy").

The phrase "amyloid-reducing activity" is meant to refer to the ability to inhibit, fully or partially, amyloid fibril formation, aggregation, or plaque formation or to remove or reduce existing amyloid fibrils, aggregates, or plaques.

The present invention provides a variety of specific binding agents, including but not limited to human or humanized Aβ-specific antibodies, that are derived from murine antibody 2.1 and retain desirable characteristics such as Kd (dissociation rate constant) for Aβ aggregates in the range of 1 $10^{-2}$ or lower, or ranging down to $10^{-9}$ or lower, (e.g., $10^{-2}$, $10^{-3}$, $10^{-4}$, $10^{-5}$, $10^{-6}$, $10^{-8}$, $10^{-9}$ or lower) and/or amyloid-reducing activity and/or therapeutic efficacy for neurodegenerative or amyloidogenic disorders such as Alzheimer's disease. The invention also provides nucleic acids encoding such specific binding agent polypeptides, vectors and recombinant host cells comprising such nucleic acids, methods of producing such specific binding agents, pharmaceutical formulations including such specific binding agents, methods of preparing the pharmaceutical formulations, and methods of treating patients with the pharmaceutical formulations and compounds.

The specific binding agents, including humanized antibodies, disclosed herein show binding to Aβ aggregates that is characterized by a dissociation rate constant ($K_d$) of $10^{-2}$ or lower. Such dissociation rate constants may be readily determined using kinetic analysis techniques such as surface plasmon resonance (BIAcore), using general procedures outlined by the manufacturer as described in Example 3 or other methods known in the art. The kinetic data obtained by BIAcore may be analyzed by methods described by the manufacturer.

The term "antibody" is used in the broadest sense and includes fully assembled antibodies, monoclonal antibodies (including human, humanized or chimeric antibodies), polyclonal antibodies, multispecific antibodies (e.g., bispecific antibodies), and antibody fragments that can bind antigen (e.g., Fab', F'(ab)$_2$, Fv, single chain antibodies, diabodies), comprising complementarity determining regions (CDRs) of the foregoing as long as they exhibit the desired biological activity. The term "antibody" explicitly excludes murine antibody (i.e. antibody produced by a murine hybridoma or having the same sequence as an antibody produced by a murine hybridoma) from the scope of the term.

The term "specific binding agent" includes antibodies as defined above and recombinant peptides or other compounds that contain sequences derived from CDRs having the desired antigen-binding properties. Specifically included in the term are peptides containing amino acid sequences that are at least 80%, 90% or 100% identical to one or more CDRs of murine antibody 2.1, preferably including heavy chain CDR3. Also included in the term are "peptibodies" which are molecules comprising an antibody Fc domain as the "vehicle" attached to at least one antigen-binding peptide. The production of peptibodies is generally described in PCT publication WO 00/24782, published May 4, 2000. Any of these peptides may be linked in tandem (i.e., sequentially), with or without linkers. Peptides containing a cysteinyl residue may be cross-linked with another Cys-containing peptide, either or both of which may be linked to a vehicle. Any peptide having more than one Cys residue may form an intrapeptide disulfide bond, as well. Any of these peptides may be derivatized, for example the carboxyl terminus may be capped with an amino group, cysteines may be cappe, or amino acid residues may substituted by moieties other than amino acid residues (see, e.g., Bhatnagar et al., J. Med. Chem. 39: 3814-9 (1996), and Cuthbertson et al., J. Med. Chem. 40: 2876-82 (1997), which are incorporated by reference herein in their entirety). The peptide sequences may be optimized, analogous to affinity maturation for antibodies, or otherwise altered by alanine scanning or random or directed mutagenesis followed by screening to identify the best binders. Lowman, Ann. Rev. Biophys. Biomol. Struct. 26: 401-24 (1997). Various molecules can be inserted into the specific binding agent structure, e.g., within the peptide portion itself or between the peptide and vehicle portions of the specific binding agents, while retaining the desired activity of specific binding agent. One can readily insert, for example, molecules such as an Fc domain or fragment thereof, polyethylene glycol or other related molecules such as dextran, a fatty acid, a lipid, a cholesterol group, a small carbohydrate, a peptide, a cyotoxic agent, a chemotherapeutic agent, a detectable moiety as described herein (including fluorescent agents, radiolabels such as radioisotopes), an oligosaccharide, oligonucleotide, a polynucleotide, interference (or other) RNA, enzymes, hormones, or the like. Other molecules suitable for insertion in this fashion will be appreciated by those skilled in the art, and are encompassed within the scope of the invention. This includes insertion of, for example, a desired molecule in between two consecutive amino acids, optionally joined by a suitable linker.

An "isolated" antibody is one that has been identified and separated from a component of its natural environment. Contaminant components of its natural environment are materials that would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody, and most preferably more than 99% by weight, (2) to a degree sufficient to obtain at least 15 residues of N-terminal or internal amino acid sequence, or (3) to homogeneity by SDS-PAGE under reducing or nonreducing conditions using Coomassie blue or, preferably, silver stain. Isolated naturally occurring antibody includes the antibody in situ within recombinant cells since at least one component of the antibody's natural environment will not be present. Ordinarily, however, isolated antibody will be prepared by at least one purification step.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against an individual antigenic site or epitope, in contrast to polyclonal antibody preparations that typically include different antibodies directed against different epitopes.

The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., Nature, 256:495 [19751, or may be made by recombinant DNA methods (see, e.g., U.S. Pat. No. 4,816,567). The "monoclonal antibodies" may also be isolated from phage antibody libraries using the techniques described in Clackson et al., Nature, 352:624-628[1991] and Marks et al., J. Mol. Biol., 222:581-597 (1991), for example.

Depending on the amino acid sequence of the constant domain of their heavy chains, human immunoglobulins can be assigned to different classes. There are five major classes, IgA, IgD, IgE, IgG and IgM, and several of these may be further divided into subclasses or isotypes, e.g. IgG1, IgG2, IgG3, IgG4, IgA1 and IgA2. The heavy-chain constant domains that correspond to the different classes of immunoglobulins are called alpha, delta, epsilon, gamma and mu respectively. The subunit structures and three-dimensional configurations of different classes of immunoglobulins are well known. Different isotypes have different effector functions; for example, IgG1 and IgG3 isotypes have ADCC activity.

The invention contemplates that monoclonal antibodies of any class or subclass may be prepared, including IgA, IgD, IgE, IgG and IgM, although IgG is preferred.

Naturally occurring antibodies contain four chains: two identical heavy chains of about 440 amino acids and two identical light chains of about 220 amino acids. Each chain comprises a variable region which differs among different antibodies, and a constant region which is the same among different antibodies. The constant region in the heavy chain is much longer than the variable region and accounts for about three quarters of the heavy chain. Within the variable region of each heavy or light chain, there are three hypervariable subregions, of a size on the order of 10 amino acids, which determine the antibody's specificity for antigen. The variable domain residues between the hypervariable regions are called the framework residues and generally are somewhat homologous among different antibodies.

The term "hypervariable" region refers to the amino acid residues of an antibody which are responsible for antigen-binding. The hypervariable region comprises amino acid residues from a complementarity determining region or CDR [i.e., residues 24-34 (L1), 50-56 (L2) and 89-97 (L3) in the light chain variable domain and 31-35 (H1), 50-65 (H2) and 95-102 (H3) in the heavy chain variable domain as described by Kabat et al., Sequences of Proteins of Immunological Interest, 5$^{th}$ Ed. Public Health Service, National Institutes of Health, Bethesda, Md. (1991)]. Even a single CDR may recognize and bind antigen, although with a lower affinity than the entire antigen binding site containing all of the CDRs.

An alternative definition of residues from a hypervariable, "loop" is described by Chothia et al., *J. Mol. Biol.* 196: 901-917 (1987) as residues 26-32 (L1), 50-52 (L2) and 91-96 (L3) in the light chain variable domain and 26-32 (H11), 53-55 (H2) and 96-101 (H3) in the heavy chain variable domain.

"Framework" or FR residues are those variable region residues other than the hypervariable region residues.

"Antibody fragments" comprise a portion of an intact full length antibody, preferably the antigen binding or variable region of the intact antibody. Examples of antibody fragments include Fab, Fab', F(ab')2, and Fv fragments; diabodies; linear antibodies (Zapata et al., Protein Eng., 8(10):1057-1062 (1995)); single-chain antibody molecules; and multispecific antibodies formed from antibody fragments.

Papain digestion of antibodies produces two identical antigen-binding fragments, called "Fab" fragments, each with a single antigen-binding site, and a residual "Fc" fragment which contains the constant region. The Fab fragment contains all of the variable domain, as well as the constant domain of the light chain and the first constant domain (CH1) of the heavy chain. The Fc fragment displays carbohydrates and is responsible for many antibody effector functions (such as binding complement and cell receptors), that distinguish one class of antibody from another.

Pepsin treatment yields an F(ab')2 fragment that has two "Single-chain Fv" or "sFv" antibody fragments comprising the VH and VL domains of antibody, wherein these domains are present in a single polypeptide chain. Fab fragments differ from Fab' fragments by the inclusion of a few additional residues at the carboxy terminus of the heavy chain CH1 domain including one or more cysteines from the antibody hinge region. Preferably, the Fv polypeptide further comprises a polypeptide linker between the VH and VL-domains that enables the Fv to form the desired structure for antigen binding. For a review of sFv see Pluckthun in The Pharmacology of Monoclonal Antibodies, vol. 1 13, Rosenburg and Moore eds., Springer-Verlag, New York, pp. 269-315 (1994).

"Fv" is the minimum antibody fragment that contains a complete antigen recognition and binding site. This region consists of a dimer of one heavy- and one light-chain variable domain in tight, non-covalent association. It is in this configuration that the three CDRs of each variable domain interact to define an antigen binding site on the surface of the VH VL dimer. Collectively, the six CDRs confer antigen-binding specificity to the antibody. However, a single variable domain (or half of an Fv comprising only three CDRs specific for an antigen) has the ability to recognize and bind antigen, although at a lower affinity than the entire binding site.

The term "diabodies" refers to small antibody fragments with two antigen-binding sites, which fragments comprise a heavy-chain variable domain (VH) connected to a light-chain variable domain (VL) in the same polypeptide chain (VH VL). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and 30 Hollinger et al., Proc. Natl. Acad. Sci. USA, 90:6444-6448 (1993).

Various techniques have been developed for the production of antibody fragments. Traditionally, these fragments were derived via proteolytic digestion of intact antibodies, but can also be produced directly by recombinant host cells. See, for example, Better et al., Science 240: 1041-1043 (1988); Skerra et al. Science 240: 1038-1041 (1988); Carter et al., Bio/Technology 10:163-167 (1992).

As provided herein, the compositions for and methods of treating neurodegenerative disorders may utilize one or more anti-Aβ antibodies used singularly or in combination with other therapeutics to achieve the desired effects. Antibodies derived from antibody 2.1 according to the present invention are preferably produced by recombinant DNA methodology using one of the antibody expression systems well known in the art (see, e.g., Harlow and Lane, Antibodies: A Laboratory Manual, Cold Spring Harbor Laboratory (1988)). Such antibodies are also preferably chimeric fusion proteins having immunoglobulin derived variable sequences and human constant regions, or more preferably are more human-like monoclonal antibodies (such as human or humanized antibodies) that comprise human antibody residues but preferably retain at least the CDRs of murine antibody 2.1. In addition to intact, full-length molecules, the term "antibody" also refers to fragments thereof or multimers or aggregates of intact molecules and/or fragments that bind to Aβ.

The phrase "humanized antibody" refers to an antibody derived from a non-human antibody, typically a mouse monoclonal antibody. Alternatively, a humanized antibody may be derived from a chimeric antibody that retains or substantially retains the antigen binding properties of the parental, non-human, antibody but which exhibits diminished immunogenicity as compared to the parental antibody when administered to humans. The phrase "chimeric antibody," as used herein, refers to an antibody containing sequence derived from two different antibodies (see, e.g., U.S. Pat. No. 4,816,567) which typically originate from different species. Most typically, chimeric antibodies comprise human and murine antibody fragments, generally human constant and mouse variable regions.

Preparation of Antibodies

Polyclonal Antibodies

Polyclonal antibodies are preferably raised in animals by multiple subcutaneous (sc) or intraperitoneal (ip) injections of the relevant antigen and an adjuvant. Alternatively, antigen may be injected directly into the animal's lymph node (see Kilpatrick et al., Hybridoma, 16:381-389, 1997). An improved antibody response may be obtained by conjugating the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride or other agents known in the art.

Animals are immunized against the antigen, immunogenic conjugates, or derivatives by combining, e.g., 100 μg of the protein or conjugate (for mice) with 3 volumes of Freund's complete adjuvant and injecting the solution intradermally at multiple sites. One month later, the animals are boosted with ⅕ to ⅒ the original amount of peptide or conjugate in Freund's complete adjuvant by subcutaneous injection at multiple sites. At 7-14 days post-booster injection, the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

Monoclonal Antibodies

Monoclonal antibodies may be made using the hybridoma method first described by Kohler et al., Nature, 256:495 (1975), or may be made by recombinant DNA methods.

In the hybridoma method, a mouse or other appropriate host animal, such as rats, hamster or macaque monkey, is immunized as herein described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, Monoclonal Antibodies: Principles and Practice, pp. 59-103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium. Human myeloma and mouse-human heteromyeloma cell lines also have been described for the production of human monoclonal antibodies (Kozbor, J. Immunol., 133:3001 (1984); Brodeur et al., Monoclonal Antibody Production Techniques and Applications, pp. 51-63 (Marcel Dekker, Inc., New York, 1987)). Exemplary murine myeloma lines include those derived from MOP-21 and M.C.-11 mouse tumors available from the Salk Institute Cell Distribution Center, San Diego, Calif. USA, and SP-2 or X63-Ag8-653 cells available from the American Type Culture Collection, Rockville, Md. USA.

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA). The binding affinity of the monoclonal antibody can, for example, be determined by BIAcore or Scatchard analysis (Munson et al., Anal. Biochem., 107:220 (1980)).

After hybridoma cells are identified that produce antibodies of the desired specificity, affinity, and/or activity, the clones may be subcloned by limiting dilution procedures and grown by standard methods (Goding, Monoclonal Antibodies: Principles and Practice, pp. 59-103 (Academic Press, 1986)). Suitable culture media for this purpose include, for example, D-MEM or RPMI-1640 medium. In addition, the hybridoma cells may be grown in vivo as ascites tumors in an animal. The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

Recombinant Production of Antibodies

The amino acid sequence of an immunoglobulin of interest may be determined by direct protein sequencing, and suitable encoding nucleotide sequences can be designed according to a universal codon table.

Alternatively, DNA encoding the monoclonal antibodies may be isolated and sequenced from the hybridoma cells using conventional procedures (e.g., by using oligonucleotide probes that are capable of binding specifically to genes encoding the heavy and light chains of the monoclonal antibodies). Sequence determination will generally require isolation of at least a portion of the gene or cDNA of interest. Usually this requires cloning the DNA or, preferably, mRNA (i.e., cDNA) encoding the monoclonal antibodies. Cloning is carried out using standard techniques (see, e.g., Sambrook et al. (1989) Molecular Cloning: A Laboratory Guide, Vols 1-3, Cold Spring Harbor Press, which is incorporated herein by reference). For example, a cDNA library may be constructed by reverse transcription of polyA+ mRNA, preferably membrane-associated mRNA, and the library screened using probes specific for human immunoglobulin polypeptide gene sequences. In a preferred embodiment, however, the polymerase chain reaction (PCR) is used to amplify cDNAs (or portions of full-length cDNAs) encoding an immunoglobulin gene segment of interest (e.g., a light chain variable segment). The amplified sequences can be readily cloned into any suitable vector, e.g., expression vectors, minigene vectors, or phage display vectors. It will be appreciated that the particular method of cloning used is not critical, so long as it is possible to determine the sequence of some portion of the immunoglobulin polypeptide of interest.

As used herein, an "isolated" nucleic acid molecule or "isolated" nucleic acid sequence is a nucleic acid molecule that is either (1) identified and separated from at least one contaminant nucleic acid molecule with which it is ordinarily associated in the natural source of the nucleic acid or (2) cloned, amplified, tagged, or otherwise distinguished from background nucleic acids such that the sequence of the nucleic acid of interest can be determined. An isolated nucleic acid molecule is other than in the form or setting in which it is found in nature. However, an isolated nucleic acid molecule includes a nucleic acid molecule contained in cells that ordinarily express the antibody where, for example, the nucleic acid molecule is in a chromosomal location different from that of natural cells.

One source for RNA used for cloning and sequencing is a hybridoma produced by obtaining a B cell from the transgenic mouse and fusing the B cell to an immortal cell. An advantage of using hybridomas is that they can be easily screened, and a hybridoma that produces a human monoclonal antibody of interest selected. Alternatively, RNA can be isolated from B cells (or whole spleen) of the immunized animal. When sources other than hybridomas are used, it may be desirable to screen for sequences encoding immunoglobulins or immunoglobulin polypeptides with specific binding characteristics. One method for such screening is the use of phage display technology. Phage display is described in e.g., Dower et al., WO 91/17271, McCafferty et al., WO 92/01047, and Caton and Koprowski, Proc. Natl. Acad. Sci. USA, 87:6450-6454 (1990), each of which is incorporated herein by reference. In one embodiment using phage display technology, cDNA from an immunized transgenic mouse (e.g., total spleen cDNA) is isolated, the polymerase chain reaction is used to amplify a cDNA sequences that encode a portion of an immunoglobulin polypeptide, e.g., CDR regions, and the amplified sequences are inserted into a phage vector. cDNAs encoding peptides of interest, e.g., variable region peptides with desired binding characteristics, are identified by standard techniques such as panning.

The sequence of the amplified or cloned nucleic acid is then determined. Typically the sequence encoding an entire variable region of the immunoglobulin polypeptide is determined, however, it will sometimes be adequate to sequence only a portion of a variable region, for example, the CDR-encoding portion. Typically the portion sequenced will be at least 30 bases in length, more often bases coding for at least about one-third or at least about one-half of the length of the variable region will be sequenced.

Sequencing can be carried out on clones isolated from a cDNA library, or, when PCR is used, after subcloning the amplified sequence or by direct PCR sequencing of the amplified segment. Sequencing is carried out using standard techniques (see, e.g., Sambrook et al. (1989) Molecular Cloning: A Laboratory Guide, Vols 1-3, Cold Spring Harbor Press, and Sanger, F. et al. (1977) Proc. Natl. Acad. Sci. USA 74: 5463-5467, which is incorporated herein by reference). By comparing the sequence of the cloned nucleic acid with published sequences of human immunoglobulin genes and cDNAs, one of skill will readily be able to determine, depending on the region sequenced, (i) the germline segment usage of the hybridoma immunoglobulin polypeptide (including the isotype of the heavy chain) and (ii) the sequence of the heavy and light chain variable regions, including sequences resulting from N-region addition and the process of somatic mutation. One source of immunoglobulin gene sequence information is the National Center for Biotechnology Information, National Library of Medicine, National Institutes of Health, Bethesda, Md.

Once isolated, the DNA may be operably linked to expression control sequences or placed into expression vectors, which are then transfected into host cells such as $E.\ coli$ cells, simian COS cells, Chinese hamster ovary (CHO) cells, or myeloma cells that do not otherwise produce immunoglobulin protein, to direct the synthesis of monoclonal antibodies in the recombinant host cells. Recombinant production of antibodies is well known in the art.

Expression control sequences refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is operably linked when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, operably linked means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

Cell, cell line, and cell culture are often used interchangeably and all such designations herein include progeny. Transformants and transformed cells include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included.

The invention also provides isolated nucleic acids encoding specific binding agents or antibodies of the invention, optionally operably linked to control sequences recognized by a host cell, vectors and host cells comprising the nucleic acids, and recombinant techniques for the production of the specific binding agents or antibodies, which may comprise culturing the host cell so that the nucleic acid is expressed and, optionally, recovering the specific binding agent or antibody from the host cell culture or culture medium.

Many vectors are known in the art. Vector components may include one or more of the following: a signal sequence (that may, for example, direct secretion of the specific binding agent or antibody), an origin of replication, one or more selective marker genes (that may, for example, confer antibiotic or other drug resistance, complement auxotrophic deficiencies, or supply critical nutrients not available in the media), an enhancer element, a promoter, and a transcription termination sequence, all of which are well known in the art.

Suitable host cells include prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescens*, and *Shigella*, as well as *Bacilli* such as *B. subtilis* and *B. licheniformis, Pseudomonas*, and *Streptomyces*. In addition to prokaryotes, eukaryotic microbes such as filamentous fungi or yeast are suitable cloning or expression hosts for specific binding agent-encoding vectors. *Saccharomyces cerevisiae*, or common baker's yeast, is the most commonly used among lower eukaryotic host microorganisms. However, a number of other genera, species, and strains are commonly available and useful herein, such as *Pichia*, e.g. *P. pastoris, Schizosaccharomyces pombe; Kluyveromyces, Yarrowia; Candida; Trichoderma reesia; Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger*.

Suitable host cells for the expression of glycosylated specific binding agent or antibody are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection of such cells are publicly available, e.g., the L-1 variant of *Autographa californica* NPV and the Bm-5 strain of *Bombyx mori* NPV.

However, interest has been greatest in vertebrate cells, and propagation of vertebrate cells in culture (tissue culture) has become routine procedure. Examples of useful mammalian host cell lines are Chinese hamster ovary cells, including CHOK1 cells (ATCC CCL61), DXB-11, DG-44, and Chinese hamster ovary cells/−DHFR (CHO, Urlaub et al., Proc. Natl. Acad. Sci. USA 77: 4216 (1980)); monkey kidney CV1 line transformed by SV40 (COS-7, ATCC CRL 1651); human embryonic kidney line (293 or 293 cells subcloned for growth in suspension culture, [Graham et al., *J. Gen Virol*. 36: 59 (1977)]; baby hamster kidney cells (BHK, ATCC CCL 10); mouse sertoli cells (TM4, Mather, Biol. Reprod. 23: 243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human hepatoma cells (Hep G2, HB 8065); mouse mammary tumor (MMT 060562, ATCC CCL51); TR1 cells (Mather et al., Annals N.Y. Acad. Sci. 383: 44-68 (1982)); MRC 5 cells or FS4 cells.

Host cells are transformed or transfected with the above-described nucleic acids or vectors for specific binding agent or antibody production and cultured in conventional nutrient media modified as appropriate for inducing promoters, selecting transformants, or amplifying the genes encoding the desired sequences. In addition, novel vectors and transfected cell lines with multiple copies of transcription units separated by a selective marker are particularly useful and preferred for the expression of specific binding agents or antibodies.

The host cells used to produce the specific binding agent or antibody of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., Meth. Enz. 58: 44 (1979), Barnes et al., Anal. Biochem. 102: 255 (1980), U.S. Pat. No. 4,767,704; 4,657,866; 4,927,762; 4,560,655; or 5,122,469; WO90103430; WO 87/00195; or U.S. Pat. Re. No. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as Gentamycin™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan. The expression vectors, pDC323 and pDC324 as described in U.S. Patent Application No. 20030082735, containing the appropriate respective light chain and heavy chain pair were transfected into the CS9 host cell line.

Upon culturing the host cells, the specific binding agent or antibody can be produced intracellularly, in the periplasmic space, or directly secreted into the medium. If the specific binding agent or antibody is produced intracellularly, as a first step, the particulate debris, either host cells or lysed fragments, is removed, for example, by centrifugation or ultrafiltration.

The specific binding agent or antibody composition can be purified using, for example, hydroxylapatite chromatography, cation or anion exchange chromatography, or preferably affinity chromatography, using the antigen of interest or protein A or protein G as an affinity ligand. Protein A can be used to purify specific binding agents or antibodies that are based on human $\gamma 1$, $\gamma 2$, or $\gamma 4$ heavy chains (Lindmark et al., *J. Immunol. Meth.* 62: 1-13 (1983)). Protein G is recommended for all mouse isotypes and for human $\gamma 3$ (Guss et al., EMBO J. 5: 15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the specific binding agent or antibody comprises a $C_H 3$ domain, the Bakerbond ABX™ resin (J. T. Baker, Phillipsburg, N.J.) is useful for purification. Other techniques for protein purification such as ethanol precipitation, Reverse Phase HPLC, chromatofocusing, SDS-PAGE, and ammonium sulfate precipitation are also possible depending on the specific binding agent or antibody to be recovered.

Chimeric and Humanized Antibodies

Because chimeric or humanized antibodies are less immunogenic in humans than the parental mouse monoclonal antibodies, they can be used for the treatment of humans with far less risk of anaphylaxis. Thus, these antibodies are preferred in therapeutic applications that involve in vivo administration to a human.

Chimeric monoclonal antibodies, in which the variable Ig domains of a rodent monoclonal antibody are fused to human constant Ig domains, can be generated using standard procedures known in the art (See Morrison, S. L., et al. (1984) Chimeric Human Antibody Molecules; Mouse Antigen Binding Domains with Human Constant Region Domains, Proc. Natl. Acad. Sci. USA 81, 6841-6855; and, Boulianne, G. L., et al, Nature 312, 643-646. (1984)). Although some chimeric monoclonal antibodies have proved less immunogenic in humans, the rodent variable Ig domains can still lead to a significant human anti-rodent response.

Humanized antibodies may be achieved by a variety of methods including, for example: (1) grafting the non-human complementarity determining regions (CDRs) onto a human framework and constant region (a process referred to in the art as humanizing through "CDR grafting"), or, alternatively, (2) transplanting the entire non-human variable domains, but "cloaking" them with a human-like surface by replacement of surface residues (a process referred to in the art as "veneering"). These methods are disclosed in, e.g., Jones et al., Nature 321:522 525 (1986); Morrison et al., Proc. Natl. Acad. Sci., U.S.A., 81:6851 6855 (1984); Morrison and Oi, Adv. Immunol., 44:65 92 (1988); Verhoeyer et al., Science 239: 1534 1536 (1988); Padlan, Molec. Immun. 28:489 498 (1991); Padlan, Molec. Immunol. 31(3):169 217 (1994); and Kettleborough, C. A. et al., Protein Eng. 4(7):773 83 (1991) each of which is incorporated herein by reference.

In particular, a rodent antibody on repeated in vivo administration in man either alone or as a conjugate will bring about an immune response in the recipient against the rodent antibody; the so-called HAMA response (Human Anti Mouse Antibody). The HAMA response may limit the effectiveness of the pharmaceutical if repeated dosing is required. The immunogenicity of the antibody may be reduced by chemical modification of the antibody with a hydrophilic polymer such as polyethylene glycol or by using the methods of genetic engineering to make the antibody binding structure more human like.

CDR grafting involves introducing one or more of the six CDRs from the mouse heavy and light chain variable Ig domains into the appropriate framework regions of a human variable Ig domain. This technique (Riechmann, L., et al., Nature 332, 323 (1988)), utilizes the conserved framework regions (FR1-FR4) as a scaffold to support the CDR loops which are the primary contacts with antigen. A significant disadvantage of CDR grafting, however, is that it can result in a humanized antibody that has a substantially lower binding affinity than the original mouse antibody, because amino acids of the framework regions can contribute to antigen binding, and because amino acids of the CDR loops can influence the association of the two variable Ig domains. To maintain the affinity of the humanized monoclonal antibody, the CDR grafting technique can be improved by choosing human framework regions that most closely resemble the framework regions of the original mouse antibody, and by site-directed mutagenesis of single amino acids within the framework or CDRs aided by computer modeling of the antigen binding site (e.g., Co, M. S., et al. (1994), J. Immunol. 152, 2968-2976).

One method of humanizing antibodies comprises aligning the non-human heavy and light chain sequences to human heavy and light chain sequences, selecting and replacing the non-human framework with a human framework based on such alignment, molecular modeling to predict the conformation of the humanized sequence and comparing to the conformation of the parent antibody. This process is followed by repeated back mutation of residues in the CDR region which disturb the structure of the CDRs until the predicted conformation of the humanized sequence model closely approximates the conformation of the non-human CDRs of the parent non-human antibody. Such humanized antibodies may be further derivatized to facilitate uptake and clearance, e.g., via Ashwell receptors (See, e.g., U.S. Pat. Nos. 5,530,101 and 5,585,089).

A number of humanizations of mouse monoclonal antibodies by rational design have been reported (See, for example, 20020091240 published Jul. 11, 2002, WO 92/11018 and U.S. Pat. No., 5,693,762, U.S. Pat. No. 5,766,866.

Human engineering of antibodies has also been described in, e.g., Studnicka et al. U.S. Pat. No. 5,766,886; Studnicka et al. Protein Engineering 7: 805-814 (1994).

Production of Antibody Variants

Amino acid sequence variants of the desired specific binding agent or antibody may be prepared by introducing appropriate nucleotide changes into the encoding DNA, or by peptide synthesis. Such variants include, for example, deletions and/or insertions and/or substitutions of residues within the amino acid sequences of the specific binding agents or antibodies. Any combination of deletion, insertion, and substitution is made to arrive at the final construct, provided that the final construct possesses the desired characteristics. The amino acid changes also may alter post-translational processes of the specific binding agent or humanized or variant antibody, such as changing the number or position of glycosylation sites.

Nucleic acid molecules encoding amino acid sequence variants of the specific binding agent or antibody are prepared by a variety of methods known in the art. Such methods include oligonucleotide-mediated (or site-directed) mutagenesis, PCR mutagenesis, and cassette mutagenesis of an earlier prepared variant or a non-variant version of the specific binding agent or antibody.

A useful method for identification of certain residues or regions of the specific binding agent or antibody that are preferred locations for mutagenesis is called "alanine scanning mutagenesis," as described by Cunningham and Wells Science, 244:1081-1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed variants are screened for the desired activity.

Ordinarily, amino acid sequence variants of the specific binding agent or antibody will have an amino acid sequence having at least 60% amino acid sequence identity with the original specific binding agent or antibody (murine or humanized) amino acid sequences of either the heavy or the light chain, or at least 65%, or at least 70%, or at least 75% or at least 80% identity, more preferably at least 85% identity, even more preferably at least 90% identity, and most preferably at least 95% identity, including for example, 80%, 81%, 82%, 83%, 84%, 85%, 86%, 87%, 88%, 89%, 90%, 91%, 92%, 93%, 94%, 95%, 96%, 97%, 98%, 99%, and 100%. Identity or homology with respect to this sequence is defined herein as the percentage of amino acid residues in the candidate sequence that are identical with the original sequence, after aligning the sequences and introducing gaps, if necessary, to achieve the maximum percent sequence identity, and not considering any conservative substitutions (as defined in Table I below) as part of the sequence identity. None of N-terminal, C-terminal, or internal extensions, deletions, or insertions into the specific binding agent or antibody sequence shall be construed as affecting sequence identity or homology. Thus, sequence identity can be determined by standard methods that are commonly used to compare the similarity in position of the amino acids of two polypeptides. Using a computer program such as BLAST or FASTA two polypeptides are aligned for optimal matching of their respective amino acids (either along the full length of one or both sequences, or along a pre-determined portion of one or both sequences). The programs provide a default opening penalty and a default gap penalty, and a scoring matrix such as PAM 250 [a standard scoring matrix; see Dayhoff et al., in *Atlas of protein Sequence and Structure*, vol. 5, supp. 3 (1978)] can be used in conjunction with the computer program. For example, the percent identity can then be calculated as: the total number of identical matches multiplied by 100 and then divided by the sum of the length of the longer sequence within the matched span and the number of gaps introduced into the longer sequences in order to align the two sequences.

Insertions

Amino acid sequence insertions include amino- and/or carboxyl-terminal fusions ranging in length from one residue to polypeptides containing a hundred or more residues, as well as intra-sequence insertions of single or multiple amino acid residues. Examples of terminal insertions include a specific binding agent or antibody with an N-terminal methionyl residue or the specific binding agent or antibody (including antibody fragment) fused to an epitope tag or a salvage receptor epitope. Other insertional variants of the specific binding agent or antibody molecule include the fusion to a polypeptide which increases the serum half-life of the specific binding agent or antibody, e.g. at the N-terminus or C-terminus.

Examples of epitope tags include the flu HA tag polypeptide and its antibody 12CA5 [Field et al., *Mol. Cell. Biol.* 8: 2159-2165 (1988)]; the c-myc tag and the 8F9, 3C7, 6E10, G4, B7 and 9E10 antibodies thereto [Evan et al., *Mol. Cell. Biol.* 5(12): 3610-3616 (1985)]; and the Herpes Simplex virus glycoprotein D (gD) tag and its antibody [Paborsky et al., *Protein Engineering* 3(6): 547-553 (1990)]. Other exemplary tags are a poly-histidine sequence, generally around six histidine residues, that permits isolation of a compound so labeled using nickel chelation. Other labels and tags, such as the FLAG® tag (Eastman Kodak, Rochester, N.Y.) are well known and routinely used in the art.

The term "salvage receptor binding epitope" refers to an epitope of the Fc region of an IgG molecule (e.g., IgG$_1$, IgG$_2$, IgG$_3$, or IgG$_4$) that is responsible for increasing the in vivo serum half-life of the IgG molecule.

Substitutions

Another type of variant is an amino acid substitution variant. These variants have at least one amino acid residue in the specific binding agent or antibody molecule removed and a different residue inserted in its place. Substitutional mutagenesis within any of the hypervariable or CDR regions or framework regions is contemplated. Conservative substitutions are shown in Table 1. The most conservative substitution is found under the heading of "preferred substitutions". If such substitutions result in no change in biological activity, then more substantial changes, denominated "exemplary substitutions" in Table 1, or as further described below in reference to amino acid classes, may be introduced and the products screened.

TABLE 1

| Original | Exemplary | Preferred Residue Substitutions |
|---|---|---|
| Ala (A) | val; leu; ile | val |
| Arg (R) | lys; gln; asn | lys |
| Asn (N) | gln; his; asp, lys; gln | arg |
| Asp (D) | glu; asn | glu |
| Cys (C) | ser; ala | ser |
| Gln (Q) | asn; glu | asn |
| Glu (E) | asp; gln | asp |
| Gly (G) | ala | |
| His (H) | asn; gln; lys; arg | |
| Ile (I) | leu; val; met; ala; phe; | leu norleucine |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | |
| Pro (P) | ala | |
| Ser (S) | thr | |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

Substantial modifications in the biological properties of the specific binding agent or antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

Conservative substitutions involve replacing an amino acid with another member of its class. Non-conservative substitutions involve replacing a member of one of these classes with a member of another class.

Any cysteine residue not involved in maintaining the proper conformation of the specific binding agent or humanized or variant antibody also may be substituted, generally with serine, to improve the oxidative stability of the molecule and prevent aberrant crosslinking. Conversely, cysteine bond(s) may be added to the specific binding agent or antibody to improve its stability (particularly where the antibody is an antibody fragment such as an Fv fragment).

Affinity Maturation

Affinity maturation involves preparing and screening specific binding agent or antibody variants that have mutations (deletions, insertions or substitutions) within the CDRs of a parent specific binding agent or antibody and selecting variants that have improved biological properties such as binding affinity relative to the parent specific binding agent or antibody. A convenient way for generating such substitutional variants is affinity maturation using phage display. Briefly, several hypervariable region sites (e.g. 6-7 sites) are mutated to generate all possible amino substitutions at each site. The specific binding agent or antibody variants thus generated may be displayed in a monovalent fashion from filamentous phage particles as fusions to the gene III product of M13 packaged within each particle. The phage-displayed variants are then screened for their biological activity (e.g. binding affinity).

Alanine scanning mutagenesis can be performed to identify hypervariable region residues that contribute significantly to antigen binding. Alternatively, or in addition, it may be beneficial to analyze a crystal structure of the antigen-antibody complex to identify contact points between the specific binding agent or antibody and the antigen. Such contact residues and neighboring residues are candidates for substitution according to the techniques elaborated herein. Once such variants are generated, the panel of variants is subjected to screening as described herein and specific binding agents or antibodies with superior properties in one or more relevant assays may be selected for further development.

Techniques utilizing gene shuffling and directed evolution may also be used to prepare and screen specific binding agent or antibody variants for desired activity. For example, Jermutus et al., Proc Natl Acad Sci USA. 2001 Jan. 2; 98(1):75-80 reports that tailored in vitro selection strategies based on ribosome display were combined with in vitro diversification by DNA shuffling to evolve either the off-rate or thermodynamic stability of single-chain Fv antibody fragments (scFvs); Fermer et al., Tumour Biol. 2004 Jan.-Apr.; 25(1-2): 7-13 reports that use of phage display in combination with DNA shuffling raised affinity by almost three orders of magnitude.

Altered Glycosylation

Specific binding agent or antibody variants can also be produced that have a modified glycosylation pattern relative to the parent specific binding agent or antibody, for example, deleting one or more carbohydrate moieties found in the specific binding agent or antibody, and/or adding one or more glycosylation sites that are not present in the specific binding agent or antibody.

Glycosylation of polypeptides including antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. The presence of either of these tripeptide sequences in a polypeptide creates a potential glycosylation site. Thus, N-linked glycosylation sites may be added to a specific binding agent or antibody by altering the amino acid sequence such that it contains one or more of these tripeptide sequences. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used. O-linked glycosylation sites may be added to a specific binding agent or antibody by inserting or substituting one or more serine or threonine residues to the sequence of the original specific binding agent or antibody.

Other Modifications

Cysteine residue(s) may be removed or introduced in the Fc region, thereby eliminating or increasing interchain disulfide bond formation in this region. The homodimeric specific binding agent or antibody thus generated may have improved internalization capability and/or increased complement-mediated cell killing and antibody-dependent cellular cytotoxicity (ADCC). See Caron et al., J. Exp Med. 176: 1191-1195 (1992) and Shopes, B. J. Immunol. 148: 2918-2922 (1992). Homodimeric specific binding agents or antibodies may also be prepared using heterobifunctional cross-linkers as described in Wolff et al., Cancer Research 53: 2560-2565 (1993). Alternatively, a specific binding agent or antibody can be engineered which has dual Fc regions and may thereby have enhanced complement lysis and ADCC capabilities. See Stevenson et al., *Anti-Cancer Drug Design* 3: 219-230 (1989).

It has been shown that sequences within the CDR can cause an antibody to bind to MHC Class II and trigger an unwanted helper T-cell response. A conservative substitution can allow the specific binding agent or antibody to retain binding activity yet reduce its ability to trigger an unwanted T-cell response.

It is also contemplated that one or more of the N-terminal 20 amino acids of the heavy or light chain are removed.

Modifications to increase serum half-life also may desirable, for example, by incorporation of or addition of a salvage receptor binding epitope (e.g., by mutation of the appropriate region or by incorporating the epitope into a peptide tag that is then fused to the specific binding agent or antibody at either end or in the middle, e.g., by DNA or peptide synthesis) (see, e.g., WO96/32478) or adding molecules such as PEG or other water soluble polymers, including polysaccharide polymers.

The salvage receptor binding epitope preferably constitutes a region wherein any one or more amino acid residues from one or two loops of a Fc domain are transferred to an analogous position of the specific binding agent or antibody or fragment. Even more preferably, three or more residues from one or two loops of the Fe domain are transferred. Still more preferred, the epitope is taken from the CH2 domain of the Fc region (e.g., of an IgG) and transferred to the CH1, CH3, or VH region, or more than one such region, of the specific binding agent or antibody. Alternatively, the epitope is taken from the CH2 domain of the Fc region and transferred to the C.sub.L region or V.sub.L region, or both, of the specific binding agent or antibody fragment. See also International applications WO 97/34631 and WO 96/32478 which describe Fc variants and their interaction with the salvage receptor.

Other sites of the constant region have been identified that are responsible for complement dependent cytotoxicity (CDC), such as the C1q binding site and/or the antibody-dependent cellular cytotoxicity (ADCC) [see, e.g., Molec. Immunol. 29 (5): 633-9 (1992); Shields et al., J. Biol. Chem., 276(9):6591-6604 (2001), incorporated by reference herein in its entirety]. Mutation of residues within Fc receptor binding sites can result in altered (i.e. increased or decreased) effector function, such as altered ADCC or CDC activity, or altered half-life. As described above, potential mutations include insertion, deletion or substitution of one or more residues, including substitution with alanine, a conservative substitution, a non-conservative substitution, or replacement with a corresponding amino acid residue at the same position from a different subclass (e.g. replacing an IgG1 residue with a corresponding IgG2 residue at that position).

Human Antibodies

Production by Transgenic Animals

Human antibodies to Aβ can also be produced using transgenic animals that have no endogenous immunoglobulin production and are engineered to contain human immunoglobulin loci. For example, WO 98/24893 discloses transgenic animals having a human Ig locus wherein the animals do not produce functional endogenous immunoglobulins due to the inactivation of endogenous heavy and light chain loci. WO 91/741 also discloses transgenic non-primate mammalian hosts capable of mounting an immune response to an immunogen, wherein the antibodies have primate constant and/or variable regions, and wherein the endogenous immunoglobulin encoding loci are substituted or inactivated. WO 96/30498 discloses the use of the Cre/Lox system to modify the immunoglobulin locus in a mammal, such as to replace all or a portion of the constant or variable region to form a modified antibody molecule. WO 94/02602 discloses non-human mammalian hosts having inactivated endogenous Ig loci and functional human Ig loci. U.S. Pat. No. 5,939,598 discloses methods of making transgenic mice in which the mice lack endogenous heavy chains, and express an exogenous immunoglobulin locus comprising one or more xenogeneic constant regions.

Using a transgenic animal described above, an immune response can be produced to a selected antigenic molecule, and antibody producing cells can be removed from the animal and used to produce hybridomas that secrete human monoclonal antibodies. Immunization protocols, adjuvants, and the like are known in the art, and are used in immunization of, for example, a transgenic mouse as described in WO 96/33735. The monoclonal antibodies can be tested for the ability to inhibit or neutralize the biological activity or physiological effect of the corresponding protein. WO 96/33735 discloses that monoclonal antibodies against IL-8, derived from immune cells of transgenic mice immunized with IL-8, blocked IL-8 induced functions of neutrophils. Human monoclonal antibodies with specificity for the antigen used to immunize transgenic animals are also disclosed in WO 96/34096 and U.S. patent application no. 20030194404; and U.S. patent application no. 20030031667).

See also Jakobovits et al., Proc. Natl. Acad. Sci. USA, 90:2551 (1993); Jakobovits et al., Nature, 362:255-258 (1993); Bruggermann et al., Year in Immuno., 7:33 (1993); and U.S. Pat. No. 5,591,669, U.S. Pat. No. 5,589,369, U.S. Pat. No. 5,545,807; and U.S. Patent Application No. 20020199213. U.S. Patent Application No. and 20030092125 describes methods for biasing the immune response of an animal to the desired epitope. Human antibodies may also be generated by in vitro activated B cells (see U.S. Pat. Nos. 5,567,610 and 5,229,275).

Production by Phage Display Techniques

The development of technologies for making repertoires of recombinant human antibody genes, and the display of the encoded antibody fragments on the surface of filamentous bacteriophage, has provided another means for making human antibodies directly. The antibodies produced by phage technology are produced as antigen binding fragments-usually Fv or Fab fragments-in bacteria and thus lack effector functions. Effector functions can be introduced by one of two strategies: The fragments can be engineered either into complete antibodies for expression in mammalian cells, or into bispecific antibody fragments with a second binding site capable of triggering an effector function.

Typically, the Fd fragment ($V_H$-$C_H1$) and light chain ($V_L$-$C_L$) of antibodies are separately cloned by PCR and recombined randomly in combinatorial phage display libraries, which can then be selected for binding to a particular antigen. The antibody fragments are expressed on the phage surface, and selection of Fv or Fab (and therefore the phage containing the DNA encoding the antibody fragment) by antigen binding is accomplished through several rounds of antigen binding and re-amplification, a procedure termed panning. Antibody fragments specific for the antigen are enriched and finally isolated.

In 1994, an approach for the humanization of antibodies, called "guided selection", was described. Guided selection utilizes the power of the phage display technique for the humanization of mouse monoclonal antibody (See Jespers, L. S., et al., Bio/Technology 12, 899-903 (1994)). For this, the Fd fragment of the mouse monoclonal antibody can be displayed in combination with a human light chain library, and the resulting hybrid Fab library may then be selected with antigen. The mouse Fd fragment thereby provides a template to guide the selection. Subsequently, the selected human light chains are combined with a human Fd fragment library. Selection of the resulting library yields entirely human Fab.

A variety of procedures have been described for deriving human antibodies from phage-display libraries (See, for example, Hoogenboom et al., J. Mol. Biol., 227:381 (1991); Marks et al., J. Mol. Biol, 222:581-597 (1991); U.S. Pat. Nos. 5,565,332 and 5,573,905; Clackson, T., and Wells, J. A., TIBTECH 12, 173-184 (1994)). In particular, in vitro selection and evolution of antibodies derived from phage display libraries has become a powerful tool (See Burton, D. R., and Barbas III, C. F., Adv. Immunol. 57, 191-280 (1994); and, Winter, G., et al., Annu. Rev. Immunol. 12, 433-455 (1994); U.S. patent application no. 20020004215 and WO92/01047; U.S. patent application no. 20030190317 published Oct. 9, 2003 and U.S. Pat. No. 6,054,287; U.S. Pat. No. 5,877,293.

Watkins, "Screening of Phage-Expressed Antibody Libraries by Capture Lift," Methods in Molecular Biology, Antibody Phage Display: Methods and Protocols 178: 187-193, and U.S. patent application no. 200120030044772 published Mar. 6, 2003 describes methods for screening phage-expressed antibody libraries or other binding molecules by capture lift, a method involving immobilization of the candidate binding molecules on a solid support.

Other Covalent Modifications

Covalent modifications of the specific binding agent or antibody are also included within the scope of this invention. They may be made by chemical synthesis or by enzymatic or chemical cleavage of the specific binding agent or antibody, if applicable. Other types of covalent modifications can be introduced into the specific binding agent or antibody by reacting targeted amino acid residues with an organic derivatizing agent that is capable of reacting with selected side chains or the N- or C-terminal residues.

Cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, .alpha.-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5-7.0 because this agent is relatively specific for the histidyl side chain. Para-bromophenacyl bromide also is useful; the reaction is preferably performed in 0.1 M sodium cacodylate at pH 6.0.

Lysinyl and amino-terminal residues are reacted with succinic or other carboxylic acid anhydrides. Derivatization with these agents has the effect of reversing the charge of the lysinyl residues. Other suitable reagents for derivatizing .alpha.-amino-containing residues include imidoesters such as methyl picolinimidate, pyridoxal phosphate, pyridoxal, chloroborohydride, trinitrobenzenesulfonic acid, O-methylisourea, 2,4-pentanedione, and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylmidizole and tetranitromethane are used to form O-acetyl tyrosyl species and 3-nitro derivatives, respectively. Tyrosyl residues are iodinated using $^{125}I$ or $^{131}I$ to prepare labeled proteins for use in radioimmunoassay.

Carboxyl side groups (aspartyl or glutamyl) are selectively modified by reaction with carbodiimides (R-N.dbd.C.dbd.N-R'), where R and R' are different alkyl groups, such as 1-cyclohexyl-3-(2-morpholinyl-4-ethyl) carbodiimide or 1-ethyl-3-(4-azonia-4,4-dimethylpentyl)carbodiimide. Furthermore, aspartyl and glutamyl residues are converted to asparaginyl and glutaminyl residues by reaction with ammonium ions.

Glutaminyl and asparaginyl residues are frequently deamidated to the corresponding glutamyl and aspartyl residues, respectively. These residues are deamidated under neutral or basic conditions. The deamidated form of these residues falls within the scope of this invention.

Other modifications include hydroxylation of proline and lysine, phosphorylation of hydroxyl groups of seryl or threonyl residues, methylation of the .alpha.-amino groups of lysine, arginine, and histidine side chains (T. E. Creighton, Proteins: Structure and Molecular Properties, W.H. Freeman & Co., San Francisco, pp. 79-86 (1983)), acetylation of the N-terminal amine, and amidation of any C-terminal carboxyl group.

Another type of covalent modification involves chemically or enzymatically coupling glycosides to the specific binding agent or antibody. These procedures are advantageous in that they do not require production of the specific binding agent or antibody in a host cell that has glycosylation capabilities for N- or O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO87/05330 published 11 Sep. 1987, and in Aplin and Wriston, CRC Crit. Rev. Biochem., pp. 259-306 (1981).

Removal of any carbohydrate moieties present on the specific binding agent or antibody may be accomplished chemically or enzymatically. Chemical deglycosylation requires exposure of the specific binding agent or antibody to the compound trifluoromethanesulfonic acid, or an equivalent compound. This treatment results in the cleavage of most or all sugars except the linking sugar (N-acetylglucosamine or N-acetylgalactosamine), while leaving the specific binding agent or antibody intact. Chemical deglycosylation is described by Hakimuddin, et al. Arch. Biochem. Biophys. 259: 52 (1987) and by Edge et al. Anal. Biochem., 118: 131 (1981). Enzymatic cleavage of carbohydrate moieties on a specific binding agent or antibody can be achieved by the use of a variety of endo- and exo-glycosidases as described by Thotakura et al. Meth. Enzymol. 138: 350 (1987).

Another type of covalent modification of the specific binding agent or antibody comprises linking the specific binding agent or antibody to one of a variety of nonproteinaceous polymers, e.g., polyethylene glycol, polypropylene glycol, polyoxyethylated polyols, polyoxyethylated sorbitol, polyoxyethylated glucose, polyoxyethylated glycerol, polyoxyalkylenes, or polysaccharide polymers such as dextran. Such methods are known in the art, see, e.g. U.S. Pat. Nos. 4,640,835; 4,496,689; 4,301,144; 4,670,417; 4,791,192, 4,179,337, 4,766,106, 4,179,337, 4,495,285, 4,609,546 or EP 315 456.

Gene Therapy

Delivery of a therapeutic specific binding agent polypeptide or antibody to appropriate cells can be effected via gene therapy ex vivo, in situ, or in vivo by use of any suitable approach known in the art. For example, for in vivo therapy, a nucleic acid encoding the desired specific binding agent or antibody, either alone or in conjunction with a vector, liposome, or precipitate may be injected directly into the subject, and in some embodiments, may be injected at the site where the expression of the specific binding agent or antibody compound is desired. For ex vivo treatment, the subject's cells are removed, the nucleic acid is introduced into these cells, and the modified cells are returned to the subject either directly or, for example, encapsulated within porous membranes which are implanted into the patient. See, e.g. U.S. Pat. Nos. 4,892,538 and 5,283,187.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, chemical treatments, DEAE-dextran, and calcium phosphate precipitation. Other in vivo nucleic acid transfer techniques include transfection with viral vectors (such as adenovirus, Herpes simplex I virus, adeno-associated virus or retrovirus) and lipid-based systems. The nucleic acid and transfection agent are optionally associated with a microparticle. Exemplary transfection agents include calcium phosphate or calcium chloride coprecipitation, DEAE-dextran-mediated transfection, quaternary ammonium amphiphile DOTMA ((dioleoyloxypropyl)trimethylammonium bromide, commercialized as Lipofectin by GIBCO-BRL)) (Felgner et al, (1987) Proc. Natl. Acad. Sci. USA 84, 7413-7417; Malone et al. (1989) Proc. Natl. Acad. Sci. USA 86 6077-6081); lipophilic glutamate diesters with pendent trimethylammonium heads (Ito et al. (1990) Biochem. Biophys. Acta 1023, 124-132); the metabolizable parent lipids such as the cationic lipid dioctadecylamido glycylspermine (DOGS, Transfectam, Promega) and dipalmitoylphosphatidyl ethanolamylspermine (DPPES) (J. P. Behr (1986) Tetrahedron Lett. 27, 5861-5864; J. P. Behr et al. (1989) Proc. Natl. Acad. Sci. USA 86, 6982-6986); metabolizable quaternary ammonium salts (DOTB, N-(1-[2,3-dioleoyloxy]propyl)-N,N,N-trimethylammonium methylsulfate (DOTAP) (Boehringer Mannheim), polyethyleneimine (PEI), dioleoyl esters, ChoTB, ChoSC, DOSC) (Leventis et al. (1990) Biochim. Inter. 22, 235-241); 3beta[N-(N',N'-dimethylaminoethane)-carbamoyl]cholesterol (DC-Chol), dioleoylphosphatidyl ethanolamine (DOPE)/3beta[N-(N',N'-dimethylaminoethane)-carbamoyl]cholesterolDC-Chol in one to one mixtures (Gao et al., (1991) Biochim. Biophys. Acta 1065, 8-14), spermine, spermidine, lipopolyamines (Behr et al., Bioconjugate Chem, 1994, 5: 382-389), lipophilic polylysines (LPLL) (Zhou et al., (1991) Biochim. Biophys. Acta 939, 8-18), [[(1,1,3,3-tetramethylbutyl)cre-soxy]ethoxy]ethyl]dimethylbenzylammonium hydroxide (DEBDA hydroxide) with excess phosphatidylcholine/cholesterol (Ballas et al., (1988) Biochim. Biophys. Acta 939, 8-18), cetyltrimethylammonium bromide (CTAB)/DOPE mixtures (Pinnaduwage et al, (1989) Biochim. Biophys. Acta 985, 33-37), lipophilic diester of glutamic acid (TMAG) with DOPE, CTAB, DEBDA, didodecylammonium bromide (DDAB), and stearylamine in admixture with phosphatidylethanolamine (Rose et al., (1991) Biotechnique 10, 520-525), DDAB/DOPE (TransfectACE, GIBCO BRL), and oligogalactose bearing lipids. Exemplary transfection enhancer agents that increase the efficiency of transfer include, for example, DEAE-dextran, polybrene, lysosome-disruptive peptide (Ohmori N I et al, Biochem Biophys Res Commun Jun. 27, 1997; 235(3):726-9), chondroitan-based proteoglycans, sulfated proteoglycans, polyethylenimine, polylysine (Pollard H et al. J Biol Chem, 1998 273 (13):7507-11), integrin-binding peptide CYGGRGDTP, linear dextran nonasaccharide, glycerol, cholesteryl groups tethered at the 3'-terminal internucleoside link of an oligonucleotide (Letsinger, R. L. 1989 Proc Natl Acad Sci USA 86: (17):6553-6), lysophosphatide, lysophosphatidylcholine, lysophosphatidylethanolamine, and 1-oleoyl lysophosphatidylcholine.

In some situations it may be desirable to deliver the nucleic acid with an agent that directs the nucleic acid-containing vector to target cells. Such "targeting" molecules include antibodies specific for a cell-surface membrane protein on the target cell, or a ligand for a receptor on the target cell. Where liposomes are employed, proteins which bind to a cell-surface membrane protein associated with endocytosis may be used for targeting and/or to facilitate uptake. Examples of such proteins include capsid proteins and fragments thereof tropic for a particular cell type, antibodies for proteins which undergo internalization in cycling, and proteins that target intracellular localization and enhance intracellular half-life. In other embodiments, receptor-mediated endocytosis can be used. Such methods are described, for example, in Wu et al., 1987 or Wagner et al., 1990. For review of the currently known gene marking and gene therapy protocols, see Anderson 1992. See also WO 93/25673 and the references cited therein. For additional reviews of gene therapy technology, see Friedmann, Science, 244: 1275-1281 (1989); Anderson, Nature, supplement to vol. 392, no 6679, pp. 25-30 (1998); Verma, Scientific American: 68-84 (1990); and Miller, Nature, 357: 455-460 (1992).

Administration and Preparation of Pharmaceutical Formulations

The anti-Aβ specific binding agents or antibodies used in the practice of a method of the invention may be formulated into pharmaceutical compositions comprising a carrier suitable for the desired delivery method. Suitable carriers include any material which, when combined with the anti-Aβ specific binding agent or antibody, retains the high-affinity binding of Aβ and is nonreactive with the subject's immune systems. Examples include, but are not limited to, any of a number of standard pharmaceutical carriers such as sterile phosphate buffered saline solutions, bacteriostatic water, and the like. A variety of aqueous carriers may be used, e.g., water, buffered water, 0.4% saline, 0.3% glycine and the like, and may include other proteins for enhanced stability, such as albumin, lipoprotein, globulin, etc., subjected to mild chemical modifications or the like.

Exemplary antibody concentrations in the formulation may range from about 0.1 mg/ml to about 180 mg/ml or from about 0.1 mg/mL to about 50 mg/mL, or from about 0.5 mg/mL to about 25 mg/mL, or alternatively from about 2 mg/mL to about 10 mg/mL. An aqueous formulation of the antibody may be prepared in a pH-buffered solution, for example, at pH ranging from about 4.5 to about 6.5, or from about 4.8 to about 5.5, or alternatively about 5.0. Examples of buffers that are suitable for a pH within this range include acetate (e.g. sodium acetate), succinate (such as sodium succinate), gluconate, histidine, citrate and other organic acid buffers. The buffer concentration can be from about 1 mM to about 200 mM, or from about 10 mM to about 60 mM, depending, for example, on the buffer and the desired isotonicity of the formulation.

A tonicity agent, which may also stabilize the antibody, may be included in the formulation. Exemplary tonicity agents include polyols, such as mannitol, sucrose or trehalose. Preferably the aqueous formulation is isotonic, although hypertonic or hypotonic solutions may be suitable. Exemplary concentrations of the polyol in the formulation may range from about 1% to about 15% w/v.

A surfactant may also be added to the antibody formulation to reduce aggregation of the formulated antibody and/or minimize the formation of particulates in the formulation and/or reduce adsorption. Exemplary surfactants include nonionic surfactants such as polysorbates (e.g. polysorbate 20, or polysorbate 80) or poloxamers (e.g. poloxamer 188). Exemplary concentrations of surfactant may range from about 0.001% to about 0.5%, or from about 0.005% to about 0.2%, or alternatively from about 0.004% to about 0.01% w/v.

In one embodiment, the formulation contains the above-identified agents (i.e. antibody, buffer, polyol and surfactant) and is essentially free of one or more preservatives, such as benzyl alcohol, phenol, m-cresol, chlorobutanol and benzethonium Cl. In another embodiment, a preservative may be included in the formulation, e.g., at concentrations ranging from about 0.1% to about 2%, or alternatively from about 0.5% to about 1%. One or more other pharmaceutically acceptable carriers, excipients or stabilizers such as those described in Remington's Pharmaceutical Sciences 16th edition, Osol, A. Ed. (1980) may be included in the formulation provided that they do not adversely affect the desired characteristics of the formulation. Acceptable carriers, excipients or stabilizers are nontoxic to recipients at the dosages and concentrations employed and include; additional buffering agents; co-solvents; antioxidants including ascorbic acid and methionine; chelating agents such as EDTA; metal complexes (e.g. Zn-protein complexes); biodegradable polymers such as polyesters; and/or salt-forming counterions such as sodium.

Therapeutic formulations of the antibody are prepared for storage by mixing the antibody having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine; histidine, arginine, or lysine; monosaccharides, disaccharides, and other carbohydrates including glucose, mannose, maltose, or dextrins; chelating agents such as EDTA; sugars such as sucrose, mannitol, trehalose or sorbitol; salt-forming counter-ions such as sodium; metal complexes (e.g., Zn-protein complexes); and/or nonionic surfactants such as TWEEN™, PLURONICS™ or polyethylene glycol (PEG).

In one embodiment, a suitable formulation of the claimed invention contains an isotonic buffer such as a phosphate, acetate, or TRIS buffer in combination with a tonicity agent such as a polyol, Sorbitol, sucrose or sodium chloride which tonicifies and stabilizes. One example of such a tonicity agent is 5% Sorbitol or sucrose. In addition, the formulation could optionally include a surfactant such as to prevent aggregation and for stabilization at 0.01 to 0.02% wt/vol. The pH of the formulation may range from 4.5-6.5 or 4.5 to 5.5. Other exemplary descriptions of pharmaceutical formulations for antibodies may be found in US 2003/0113316 and U.S. Pat. No. 6,171,586, each incorporated herein by reference in its entirety.

The formulation herein may also contain more than one active compound as necessary for the particular indication being treated, preferably those with complementary activities that do not adversely affect each other. For example, it may be desirable to further provide an immunosuppressive agent. Such molecules are suitably present in combination in amounts that are effective for the purpose intended.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Suspensions and crystal forms of antibodies are also contemplated. Methods to make suspensions and crystal forms are known to one of skill in the art.

The formulations to be used for in vivo administration must be sterile. The compositions of the invention may be sterilized by conventional, well known sterilization techniques. For example, sterilization is readily accomplished by filtration through sterile filtration membranes. The resulting solutions may be packaged for use or filtered under aseptic conditions and lyophilized, the lyophilized preparation being combined with a sterile solution prior to administration.

The process of freeze-drying is often employed to stabilize polypeptides for long-term storage, particularly when the polypeptide is relatively unstable in liquid compositions. A lyophilization cycle is usually composed of three steps: freezing, primary drying, and secondary drying; Williams and Polli, Journal of Parenteral Science and Technology, Volume 38, Number 2, pages 48-59 (1984). In the freezing step, the solution is cooled until it is adequately frozen. Bulk water in the solution forms ice at this stage. The ice sublimes in the primary drying stage, which is conducted by reducing chamber pressure below the vapor pressure of the ice, using a vacuum. Finally, sorbed or bound water is removed at the secondary drying stage under reduced chamber pressure and an elevated shelf temperature. The process produces a material known as a lyophilized cake. Thereafter the cake can be reconstituted prior to use.

The standard reconstitution practice for lyophilized material is to add back a volume of pure water (typically equivalent to the volume removed during lyophilization), although dilute solutions of antibacterial agents are sometimes used in the production of pharmaceuticals for parenteral administration; Chen, Drug Development and Industrial Pharmacy, Volume 18, Numbers 11 and 12, pages 1311-1354 (1992).

Excipients have been noted in some cases to act as stabilizers for freeze-dried products; Carpenter et al., Developments in Biological Standardization, Volume 74, pages 225-239 (1991). For example, known excipients include polyols (including mannitol, sorbitol and glycerol); sugars (including glucose and sucrose); and amino acids (including alanine, glycine and glutamic acid).

In addition, polyols and sugars are also often used to protect polypeptides from freezing and drying-induced damage and to enhance the stability during storage in the dried state. In general, sugars, in particular disaccharides, are effective in both the freeze-drying process and during storage. Other classes of molecules, including mono- and di-saccharides and polymers such as PVP, have also been reported as stabilizers of lyophilized products.

For injection, the pharmaceutical formulation and/or medicament may be a powder suitable for reconstitution with an appropriate solution as described above. Examples of these include, but are not limited to, freeze dried, rotary dried or spray dried powders, amorphous powders, granules, precipitates, or particulates. For injection, the formulations may optionally contain stabilizers, pH modifiers, surfactants, bioavailability modifiers and combinations of these.

Sustained-release preparations may be prepared. Suitable examples of sustained-release preparations include semipermeable matrices of solid hydrophobic polymers containing the antibody, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and y ethyl-L-glutamate, non-degradable ethylene-vinyl acetate, degradable lactic acid-glycolic acid copolymers such as the Lupron Depot™ (injectable microspheres composed of lactic acid-glycolic acid copolymer and leuprolide acetate), and poly-D-(-)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

The formulations of the invention may be designed to be short-acting, fast-releasing, long-acting, or sustained-releasing as described herein. Thus, the pharmaceutical formulations may also be formulated for controlled release or for slow release.

Specific dosages may be adjusted depending on conditions of disease, the age, body weight, general health conditions, sex, and diet of the subject, dose intervals, administration routes, excretion rate, and combinations of drugs. Any of the above dosage forms containing effective amounts are well within the bounds of routine experimentation and therefore, well within the scope of the instant invention.

The specific binding agent or antibody is administered by any suitable means, including parenteral, subcutaneous, intraperitoneal, intrapulmonary, and intranasal, and, if desired for local treatment, intralesional administration. Parenteral infusions include intravenous, intraarterial, intraperitoneal, intramuscular, intradermal or subcutaneous administration. In addition, the specific binding agent or antibody is suitably administered by pulse infusion, particularly with declining doses of the specific binding agent or antibody. Preferably the dosing is given by injections, most preferably intravenous or subcutaneous injections, depending in part on whether the administration is brief or chronic. Other administration methods are contemplated, including topical, particularly transdermal, transmucosal, rectal, oral or local administration e.g. through a catheter placed close to the desired site. Most preferably, the specific binding agent or antibody of the invention is administered intravenously in a physiological solution at a dose ranging between 0.01 mg/kg to 100 mg/kg at a frequency ranging from daily to weekly to monthly (e.g. every day, every other day, every third day, or 2, 3, 4, 5, or 6 times per week), preferably a dose ranging from 0.1 to 45 mg/kg, 0.1 to 15 mg/kg or 0.1 to 10 mg/kg at a frequency of 2 or 3 times per week, or up to 45 mg/kg once a month.

Administration to Brain

A variety of approaches are known in the art to effect administration of compounds to the brain. For example, a compound may be administered by direct intraventricular or intrathecal injection, preferably via slow infusion to minimize impact on brain parenchyma. The desired drug may also be delivered using a slow release implant in the brain, or (where the drug is a polypeptide) implanted recombinant cells that produce the drug. The blood brain barrier (BBB) may be permeabilized concomitant with drug administration, to permit movement of the drug across the BBB. Permeabilizing agents include osmotic agents, such as hypertonic mannitol, or another permeabilizing agent such as bradykinin, an alkylglycerol, ultrasound, electromagnetic radiation or parasympathetic innervation.

Alternatively, receptor-mediated transport may be utilized to administer drug to the brain. It is known in the art that peptides and proteins that directly cross the BBB may serve as carriers for selective therapeutic agents that allow the therapeutic agents to cross the BBB after delivery into the bloodstream (Pan et al., Brain Research Reviews, 46:32-43, 2004; Misra et al., J. Pharm. Pharmaceut. Sci., 6:252-273, 2003; Begley, Pharmacol Ther. 2004 October; 104(1):29-45; Poduslo, US App. Pub. No. 2003/0082191; Poduslo et al., Biochem., 43:6064-6075, 2004). For example, Poduslo, WO 03/020212 describes conjugation of antibodies to amyloid-beta protein fragments which are then taken up by low-density lipoprotein receptor related protein-1, a transporter at the BBB. Other examples of peptides which cross the BBB include transferrin which binds to the transferrin receptor, a transporter at the BBB; monoclonal antibodies to the transferrin receptor such as OX26; cell penetrating peptides such as TAT transduction domain, penetratin, or Syn B1; and RAP which binds to low-density lipoprotein receptor related protein-2, another transporter at the BBB (see Pan et al., J Cell Sci. 2004 Oct. 1; 117(Pt 21):5071-8).

Receptor-mediated drug delivery to the brain may employ chimeric peptide technology, wherein a non-transportable drug is conjugated to a BBB transport vector. The latter may be a modified protein or receptor-specific monoclonal antibody that undergoes receptor-mediated transcytosis through the BBB in-vivo. Conjugation of drug to transport vector is facilitated with chemical linkers, avidin-biotin technology, polyethylene glycol linkers, or liposomes. Multiple classes of therapeutics have been delivered to the brain with the chimeric peptide technology, including peptide-based pharmaceuticals, anti-sense therapeutics including peptide nucleic acids (PNAs), and small molecules incorporated within liposomes. Alternatively, the drug may be encapsulated in a liposome or nanoparticle which is then linked to the BBB transport vector.

Administration with Other Agents

The antibodies of the invention also may be concurrently administered with other anti-amyloidgenic therapeutic agents. Concurrent administration includes administration of the two different therapeutic agents at different times and at different routes, as long as there is some overlap in the time during which the agents are exerting their therapeutic effects.

Exemplary anti-amyloidgenic agents known in the art include other anti-amyloid-beta antibodies, anti-inflammatories known in the art (e.g., NSAIDs and Cox-2 inhibitors) that reduce the pathogenic effects of amyloid accumulation, cholesterol lowering drugs, β-secretase inhibitors, or anti-inflammatories that reduce the inflammatory response due to the administration of Aβ antibody or that allow monitoring of the side effects of the anti-Aβ antibody.

The invention is illustrated by the following examples, which are not intended to be limiting in any way.

EXAMPLES

Example 1

Production and Purification of Humanized Anti-Amyloid Antibody

The monoclonal anti-amyloid antibody 2.1 is a murine IgG1 produced from a hybridoma cell line.

Total RNA was isolated from the murine hybridoma 2.1 expressing an anti-human Amyloid binding monoclonal antibody and purified. A 5' RACE (rapid amplification of cDNA ends) oligo was added to the RNA. First strand cDNA was synthesized from this modified RNA using a random primer with an extension adapter. A set of 5' RACE PCRs (polymerase chain reactions) was performed to amplify the cDNAs that coded for the anti-human Amyloid antibody. For the complete light chain, a RACE PCR was preformed using a nested 5' RACE primer as the forward primer and a murine kappa constant region primer as the reverse primer. The RACE PCR for the variable region of the heavy chains used a nested 5' RACE primer as the forward primer and the reverse primer was a rat/mouse IgG1 specific constant region primer. RACE products were cloned and the sequences determined. Consensus sequences were used to design primers for murine/human chimeric antibody chain PCR amplifications.

The expression clones for the anti-Amyloid murine/human chimeric kappa light chain was prepared by PCR using a 5' PCR primer encoded the amino terminus of the signal sequence, an XbaI restriction enzyme site, and an optimized Kozak sequence. The 3' primer encoded the carboxyl terminus murine kappa variable region as well as a BsmBI restriction enzyme site. The resulting approximately 400 base pair fragment was then digested with XbaI and BsmBI and ligated into the XbaI and BsmBI cohesive ends of the linearized mammalian expression vector pDSRα20 (see International Application, Publication No. WO 90/14363, which is herein incorporated by reference for any purpose) containing the human kappa constant region.

Total RNA was extracted from hybridoma cells and the variable regions for both the heavy and light chains of the antibody were cloned from cDNA. The murine VH and VK genes were sequenced. Murine VH and VK were used to generate fully murine ("murine 2.1") and murine/human chimerical forms ("2.1 chimera") of the antibody. The desired anti-amyloid properties for the chimera were verified and the antibody was subjected to humanization.

The CDRs of murine 2.1 may be transferred to the framework of any suitable human sequence, human consensus sequence, or human germline sequence, including chimeric or consensus germline sequence. Acceptable homologous framework regions for heavy and light chains include VH2-70 and VKII A19. A variety of mutations or substitutions in the light chain framework have been made to create humanized variants (See FIG. 1B and Table 2 below).

TABLE 2

| Dimeric Antibody Name | Heavy Chain | Light Chain |
| --- | --- | --- |
| 2.1 murine | 2.1 murine HC (SEQ ID NO: 4) | 2.1 murine LC (SEQ ID NO: 2) |
| 2.1 A | 2.1 HC X (SEQ ID NOs: 7, 8) | 2.1 LC A (SEQ ID NOs: 5, 6) |
| 2.1 B | 2.1 HC Y (SEQ ID NOs: 29, 30) | 2.1 LC B (SEQ ID NOs: 15, 16) |
| 2.1 C | 2.1 HC Y | 2.1 LC C (SEQ ID NOs: 17, 18) |
| 2.1 D | 2.1 HC Y | 2.1 LC D (SEQ ID NOs: 19, 20) |
| 2.1 E | 2.1 HC Y | 2.1 LC E (SEQ ID NOs: 21, 22) |
| 2.1 F | 2.1 HC Y | 2.1 LC F (SEQ ID NOs: 23, 24) |
| 2.1 G (also described as 2.1 GK5R) | 2.1 HC Y | 2.1 LC G (SEQ ID NOs: 25, 26) |
| 2.1 G K5 | 2.1 HC X | 2.1 LC G |
| 2.1 I (also described as 2.1 I K5R) | 2.1 HC Y | 2.1 LC I (SEQ ID NOs: 27, 28) |
| 2.1 I K5 | 2.1 HC X | 2.1 LC I |
| 2.1 J | 2.1 HC X | 2.1 LC J (SEQ ID NOs: 33, 34) |
| 2.1 K | 2.1 HC Z (SEQ ID NOs: 31, 32) | 2.1 LC A |
| 2.1 L | 2.1 HC Y | 2.1 LC A |
| 2.1 N | 2.1 HC Z | 2.1 LC J |

Example 2

In Vitro Binding of Antibodies

This example evaluates the in vitro binding of ("2.1 A"), 2.1 chimera and a variety of humanized 2.1 antibodies to Aβ (monomer and fibrils) and to collagen fibrils. All candidates are run at multiple concentrations in order to obtain concentration response information (where response=binding). From the concentration response curve one can determine an EC50 (the concentration that provokes a response halfway between baseline and maximum response). The EC50 is reflective of binding affinity; however, under the conditions used here, it is not a direct measure of $K_D$. As a negative control, collagen fibrils were used to assess non-specific binding of antibodies.

The fibrils (Aβ or collagen) were diluted to 10 μg/ml in water and mixed thoroughly. The solution was aliquoted into the wells of a microtiter plate (Immulon-2; VWR; Cat # 62404-972) at 50 μl per well (resulting in 0.5 μg fibrils/well final). The plate was dried overnight by being placed uncovered in a 37° C. incubator.

The same techniques were used for the coating of the microtiter plate for monomer ELISA. The fibrils Aβ monomer were diluted to 2.5 μg/ml in Coating buffer and mixed thoroughly. The solution was aliquoted into the wells of a microtiter plate [Immulon-2; VWR; Cat.#62404-972] at 100 μl per well. The plate was sealed and incubated overnight at 4° C. The plate was washed 5-10× to remove Aβ coating solution prior to starting the assay.

The wells were blocked with 200 μl of blocking solution and incubated for ≧1 hour at room temperature (RT) with shaking. The blocking solution was flicked out and gently dried on a paper towel. 100 μl of primary antibody diluted in PBS containing 10% blocking solution was added to each well and the plate was incubated at RT for 1 hour with shaking. The plate was washed with 5-10× in TBS, pH 7.5+0.05% Tween 20. 100 μl of secondary antibodies (each diluted 1-2,000-fold in PBS) was added to each well and the plate was incubate at RT for 1 hour with shaking. The plate was washed with 5-10× in TBS, pH 7.5+0.05% Tween 20. 100 μl Streptavidin-Europium reagent (1-1,000-fold dilution) was added and the plated was incubated at RT for 45 minutes with shaking. The plate was washed 5-10× in TBS, pH 7.5+0.05% Tween 20. 120 μl Enhance Solution was added and the plate was incubated for 15-30 minutes with shaking. The plate was read on a Victor TRF plate reader (Europium program).

Monoclonal antibodies 2.1-chimera and 2.1 A both demonstrated strong binding to Aβ40 and Aβ42 fibrils. EC50s for these antibodies range from 60 to 80 μM on Aβ42 and Aβ40 fibrils (See Table 3 below).

TABLE 3

| ELISA Assay | 2.1-Chimera (EC50) | 2.1 A (EC50) |
| --- | --- | --- |
| Fibrillar Aβ40 | $6.0 \times 10^{-11}$ M | $6.5 \times 10^{-11}$ M |
| Fibrillar Aβ42 | $7.2 \times 10^{-11}$ M | $7.4 \times 10^{-11}$ M |
| Fibrillar collagen | No binding | No binding |
| Aβ40 monomer | $3.1 \times 10^{-11}$ M | $2.9 \times 10^{-11}$ M |
| Aβ42 monomer | $3.4 \times 10^{-11}$ M | $3.1 \times 10^{-11}$ M |

Neither antibody showed any binding in the collagen fibril counter-screen. Likewise, in the Aβ40 and Aβ42 monomer ELISAs, 2.1 A showed binding equivalent to that of the 2.1-Chimera control. EC50s for both antibodies range from 20 to 40 pM for both peptides. 2.1 J had reduced binding activity in comparison to 2.1 A and 2.1 chimera. 2.1 N has no significant binding.

The in vitro binding assay described above was repeated using various humanized versions of anti-Aβ antibodies (2.1 chimera, 2.1 B, 2.1 C, 2.1 D, 2.1 E, 2.1 F, 2.1 G, 2.1 E.K5, 2.1E.K5R, 2.1 G.K5, 2.1 G.K5R, 2.1 I.K5R and 2.1 L) using 2.1 chimera as a positive control. A visual qualitative assessment of ELISA results for these antibodies indicated that all of them bound to amyloid monomers and aggregates as well as 2.1 chimera (all scored 5/5), except for 2.1 B (K5R) (scored 4/5).

Example 3

Kinetic Analysis of mAb 2.1 Binding to Human Aβ-Peptides

Kinetic binding analysis was performed using BIAcore to study the interaction of mAb 2.1 and various humanized 2.1 antibodies to human Aβ40 and Aβ42 aggregates and monomers.

Preparation of BIAcore Chip Surfaces: Immobilization of Proteins to a BIAcore sensor chip (CM5) was performed according to manufacturer's instructions. Briefly, carboxyl groups on the sensor chip surfaces were activated by injecting 60 μL of a mixture containing 0.2 M N-ethyl-N'-(dimethylaminopropyl)carbodiimide (EDC) and 0.05 M N-hydroxysuccinimide (NHS). Specific surfaces were obtained by injecting rProtein G (Pierce), goat anti-mouse Fc (Jackson Immuno Research Lab) or Aβ aggregates diluted in 10 mM acetate, pH 4.0 at concentrations between 5 and 20 μg/mL. Excess reactive groups on the surfaces were deactivated by injecting 60 μL of 1 M ethanolamine. Final immobilized levels were about 10000 resonance units (RU) for the Protein G and anti-mouse Fc surfaces, and 400 RU for the Aβ aggregates surfaces. A blank, mock-coupled reference surface was also prepared on the sensor chips for background subtraction.

Kinetic analysis of antibodies binding to immobilized Aβ aggregates: Antibodies were diluted in PBS+0.005% P-20+ 0.1 mg/mL BSA from 100 nM to 0.2 nM. The samples at each concentration were injected over the immobilized Aβ aggregate surfaces, as well as over a blank surface for background subtraction. After a 15-minute dissociation, the surface was regenerated by injecting 8 mM glycine, pH 3.0, and 1 M NaCl for 30 seconds.

Kinetic analysis of Aβ monomers binding to protein G captured antibodies: The kinetic analysis of the interaction between Aβ monomers and antibodies was performed as follows: 2.1A and mAb 2.1 were diluted in PBS+0.005% P-20+0.1 mg/mL BSA and injected over the immobilized protein G or anti-mouse Fc surfaces. Aβ monomers were diluted in PBS+0.005% P-20+0.1 mg/mL BSA from 1000 nM to 2 nM, and each concentration was injected over the captured antibody surfaces. After 3 minutes dissociation, each surface was regenerated by injection of 10 mM glycine, pH 1.5.

Kinetic data analysis of the sensorgrams was performed using BIAevaluation, v. 3.2 (Biacore, Inc., Uppsala, Sweden) to extract $k_a$ and $k_d$. $K_D$ was estimated as $k_d/k_a$.

Both Aβ monomers and aggregates were tested for binding with 2.1 A and mAb 2.1 using BIAcore. The $K_D$ of 2.1 A and mAb 2.1 binding to Aβ monomers were about 20 to 70 nM as determined in the kinetic analysis. The binding between the Aβ aggregates and the antibodies were much stronger than the binding between the AD monomers and the antibodies. The difference in the binding activity was primarily caused by the difference in the dissociation rate constant ($k_d$), since the dissociation of the antibodies from Aβ aggregates was much slower than their dissociation from monomers. Tables 4 and 5 summarize the results of mAb 2.1 and 2.1 A binding with Aβ monomers and aggregates. The $K_d$ for 2.1 A was on same order as chimera 2.1.

TABLE 4

Binding of mAb 2.1 to Aβ monomers and aggregates

| Aβ samples | $K_D$ (M) | $k_a$ ($M^{-1} \cdot sec^{-1}$) | $k_d$ ($sec^{-1}$) |
|---|---|---|---|
| Aβ40 monomer | $4.2 \times 10^{-8}$ | $9.8 \times 10^4$ | $4.1 \times 10^{-3}$ |
| Aβ42 monomer | $1.7 \times 10^{-8}$ | $4.2 \times 10^4$ | $7.2 \times 10^{-4}$ |
| Aβ40 aggregate | — | — | $<5 \times 10^{-5}$ |
| Aβ42 aggregate | — | — | $<5 \times 10^{-5}$ |

TABLE 5

Binding of 2.1 A to Aβ monomers and aggregates

| Aβ samples | $K_D$ (M) | $k_a$ ($M^{-1} \cdot sec^{-1}$) | $k_d$ ($sec^{-1}$) |
|---|---|---|---|
| Aβ40 monomer | $6.8 \times 10^{-8}$ | $1.4 \times 10^5$ | $9.4 \times 10^{-3}$ |
| Aβ42 monomer | $5.0 \times 10^{-8}$ | $9.8 \times 10^4$ | $4.9 \times 10^{-3}$ |
| Aβ40 aggregate | — | — | $<5 \times 10^{-5}$ |
| Aβ42 aggregate | — | — | $<5 \times 10^{-5}$ |

Binding of 2.1 A and mAb 2.1 to AD aggregates are fairly strong with dissociation rate constant smaller than $5 \times 10^{-5}$ $sec^{-1}$, suggesting that ~50% binding will remain after 4 hours dissociation of the antibodies from Aβ aggregates. A slower dissociation rate is helpful to the antibodies' ability to bind to plaques in brain tissue and induce phagocytosis of amyloid.

Based on BIAcore analysis, 2.1 N had no significant binding activity and no off-rates were calculated.

The kinetic analysis assay as described above was repeated using various humanized versions of anti-Aβ antibodies (2.1 chimera, 2.1 B, 2.1 C, 2.1 D, 2.1 E, 2.1 F, 2.1 G, 2.1 E.K5, 2.1E.K5R, 2.1 G.K5, 2.1 G.K5R, 2.1 I.K5R and 2.1 L). Table 6 summarizes the results of anti-Aβ antibodies binding to Aβ fibrils.

TABLE 6

Binding of Humanized variants to Aβ 40 and Aβ 42 fibrils

| Antibody | Aβ 40 fibrils $k_d$(1/s) | Aβ 42 fibrils $k_d$(1/s) |
|---|---|---|
| 2.1 chimera | $1.2 \times 10^{-4}$ | $6.9 \times 10^{-5}$ |
| 2.1 B (K5R) | $2.4 \times 10^{-4}$ | $1.9 \times 10^{-4}$ |
| 2.1 C (K5R) | $1.5 \times 10^{-4}$ | $<5 \times 10^{-5}$ |
| 2.1 D (K5R) | $1.2 \times 10^{-4}$ | $5.5 \times 10^{-5}$ |
| 2.1 E (K5R) | $1.1 \times 10^{-4}$ | $<5 \times 10^{-5}$ |
| 2.1 F (K5R) | $1.5 \times 10^{-4}$ | $1.2 \times 10^{-4}$ |
| 2.1 G (K5R) | $1.1 \times 10^{-4}$ | $<5 \times 10^{-5}$ |
| (CHO) 2.1 Chimera (control) | $5.9 \times 10^{-5}$ | $6.3 \times 10^{-5}$ |
| 2.1 E (K5) | $<5 \times 10^{-5}$ | $<5 \times 10^{-5}$ |
| 2.1 E (K5R) | $<5 \times 10^{-5}$ | $<5 \times 10^{-5}$ |
| 2.1 G (K5) | $<5 \times 10^{-5}$ | $<5 \times 10^{-5}$ |
| 2.1 G (K5R) | $<5 \times 10^{-5}$ | $<5 \times 10^{-5}$ |
| 2.1 I (K5R) | $<5 \times 10^{-5}$ | $<5 \times 10^{-5}$ |
| 2.1 A | $<5 \times 10^{-5}$ | $<5 \times 10^{-5}$ |
| 2.1 L | $<5 \times 10^{-5}$ | $<5 \times 10^{-5}$ |

Example 4

Immunohistochemical Analysis of Antibodies on Tg2576 Mouse Brain and Human Brain Sections The ability of murine anti-Aβ mAb 2.1 and a variety of humanized 2.1 antibodies to bind to native amyloid plaques in situ was evaluated in unfixed fresh frozen tissue sections of human AD brain and of Tg2576 transgenic mouse brains.

Brain Dissection: Animals were sacrifices with inhalation of $CO_2$ and were perfused with saline. Brains were dissected out from the skull and bisected at the mid-line. Half of the brain was frozen on dry ice for future biochemical study and the other half was embedded in OCT embedding medium and frozen on dry ice for histology studies.

Histology: 14 mm-thick fresh frozen coronal serial sections of mouse brains or the cerebral cortex of a human AD brain were cut using a cryostat microtome. Sections were thaw-mounted onto Fisher "plus" microscope slides and briefly air-dried. Sections were stored at −20° C. until use. At the time of staining, sections were warmed to room temperature and the endogenous tissue peroxidase activity was destroyed by incubating with 3% $H_2O_2$ in PBS for 15 minutes. There were a total of four different combinations to evaluate one mouse and one human antibody on both mouse and human brain sections.

For evaluation of mouse antibody on mouse brain sections, Chemicon Mouse to Mouse Kit was used to avoid non-specific staining of mouse IgG left in the brain sections. Sections were incubated in the pre-antibody blocking solution (Cat# 2700) for 1 hour at room temperature to block all of the endogenous mouse IgG. The sections were stained with 1 μg/ml of mouse $1^{st}$ antibody in the same blocking solution on the shaker at 4° C. overnight. The sections were then blocked with post-antibody blocking solution (Cat# 2700) for 18 minutes and ready for the $2^{nd}$ antibody. Sections were then incubated with 2 µg/ml biotinylated anti-mouse IgG on the shaker at room temperature for 1 hour.

For evaluation of mouse antibody 2.1 on human brain, sections were incubated in a blocking solution (3% normal goat serum/5% normal horse serum/0.25% carrageenan lambda/0.1% triton/PBS) for 1 hour. Sections were incubated with 1 µg/ml of mouse $1^{st}$ antibody in the above blocking solution at 4° C. overnight. Sections were then incubated with 2 µg/ml biotinylated anti-mouse IgG on the shaker at room temperature for 1 hour.

For evaluation of humanized antibodies on mouse brains, sections were incubated in a blocking solution (3% normal goat serum/5% normal horse serum/0.25% carrageenan lambda/0.1% triton/PBS) for 1 hour. Sections were incubated with 1 µg/ml humanized IgG in the above blocking solution at 4° C. overnight. Sections were then incubated with 2 µg/ml biotinylated goat anti-human IgG on the shaker at room temperature for 1 hour.

For evaluation of humanized antibodies on human brains, sections were incubated in a blocking solution (3% normal goat serum/5% normal horse serum/0.25% carrageenan lambda/0.1% triton/PBS) for 1 hour. Sections were incubated with 1 µg/ml biotinylated humanized IgG in the above blocking solution at 4° C. overnight.

For all four staining protocols listed above, the antigen was detected by ABC/DAB protocol as described in Yan et al, *J. Comp. Neurol.*, 378:135-157 (1997). Sections were dehydrated and cover-slipped with mounting medium.

Unfixed sections of a 20 month-old Tg25476 mouse brain containing a substantial amount of amyloid plaques were used to test the ability of mAb 2.1 to recognize native amyloid plaques. A commercially available anti-Aβ antibody, mAb 4G8, was used as a positive control. The staining intensity, plaque density and the level of background of both mAb 2.1 and mAb 4G8 were similar. Irrelevant mouse monoclonal IgG showed no staining as expected.

Next, unfixed sections from a 91 year-old AD brain was used to evaluated if mAb 2.1 could recognize human amyloid plaques. The staining intensity, plaque density and the level of background of both mAb 2.1 and mAb 4G8 were similar. Irrelevant mouse monoclonal IgG showed no staining as expected.

To evaluate the clinical utility of mAb 2.1, mouse Fab/human Fc chimeric antibody (2.1 chimera) and a series of CDR grafted humanized mAb 2.1 antibodies were generated, and were used to stain the sections of a 20 month-old Tg2576 mouse brain. The amyloid plaque staining intensity, plaque density and the level of background of the 2.1 chimera, 2.1 J, 2.1 K and 2.1 A were similar to both mAb 2.1 and mAb 4G8. 2.1 N had no activity.

To evaluate the humanized antibodies on human brain sections, they were biotinylated, thus bypassing the need for a secondary antibody. One of the human versions of mAb 2.1, 2.1 A was tested on the adjacent sections of the same AD brain used above. The staining intensity, plaque density and the level of background were similar to both mAb 2.1 and mAb 4G8. These results indicate that murine anti-Aβ antibody mAb 2.1 and 2.1 A bind amyloid plaques in unfixed fresh frozen brain sections of a Tg2576 APP transgenic mouse and human AD patient.

Immunohistochemistry analysis as described above was repeated using various humanized versions of anti-Aβ antibodies (2.1 chimera, 2.1 B, 2.1 C, 2.1 D, 2.1 E, 2.1 F, 2.1 G, 2.1 E.K5, 2.1E.K5R, 2.1 G.K5, 2.1 G.K5R, 2.1 I.K5R and 2.1 L) on unfixed sections of a 19 month-old Tg25476 mouse brain containing a substantial amount of amyloid plaques. The staining intensity, plaque density and low level of background observed was similar for all antibodies tested (relative scores of 5 for all antibodies except for 2.1 L which had a relative score of 4, and except for 2.1G.K5R and 2.1 I.K5R, which each had a relative score of 4+). Irrelevant mouse monoclonal IgG showed no staining as expected.

Example 5

Functional Activity of Antibodies in Ex Vivo Phagocytosis Assay

In this ex vivo phagocytosis assay, candidate antibodies were characterized for their ability to induce phagocytosis of amyloid deposits in brain section of Tg2576 mice or a human AD patient.

Primary microglial cell culture. Primary microglial cells from the forebrains of neonate CD1 mice (1-3 day old) were prepared by a modification of published procedures (Dotmerits, 1998; Park et al., *J. Neurochem.*, 72:1948-1958 (1999)). In brief, the meninges were removed from the forebrain, and forebrains were mechanically dissociated in 5 ml of papain in Earle's Balanced Salt Solution containing L-Cysteine and EDTA (Worthington Biochem Corp., Lakewood, N.J.) with 100 µl of DNase I (Sigma, St. Louis, Mo.) at 37° C. for 30 min. The cell suspension was centrifuged at 2200 g for 5 min. The pellet was resuspended in 5-10 ml growth medium of high glucose DMEM (Gibco BRL, Grand Island, N.Y.); 10% FBS (Gibco BRL); 25 µg/ml nmGM-CSF (R&D, Minneapolis, Minn.) and 100 µl DNase I, and further dissociated by several triturations using a pipette. The dissociated cells were filtered with a 70 µm cell strainer (Falcon, Franklin Lakes, N.J.), and centrifuged at 200 g for 5 minutes. The pellet was resuspended in the growth medium and the cells were plated at a density of 3 brains ($1.8 \times 10^7$ cells) per T-75 plastic culture flask. After 10-14 days, the flasks were rotated on an orbital shaker (LAB-line, Melrose Park, Ill.) at 200 rpm for 4-6 hrs at 37° C. The cell suspension was centrifuged at 200 g and resuspended in the assay medium consisting if Hybridoma-serum free medium (Gibco BRL, Grand Island, N.Y.) with 1% FBS, glutamine, penicillin/streptomycin, and 5 ng/ml nmGM-CSF.

Cell line culture. IC-21 and other cells were obtained from ATCC and culture in RPMI (Gibco BRL) supplemented with 2 mM L-glutamine, 1.5 g/L sodium bicarbonate, 4.5 g/L glucose, 10 mM HEPES (Gibco BRL), 1.0 mM sodium pyruvate (Gibco BRL) and 10% fetal bovine serum. Confluent cultures of IC-21 cells were detached from the T-75 plastic culture flask with 1% trypsin (Gibco BRL). The cell suspension was centrifuged at 1000 prm and resuspended in the assay medium consisting of hybridoma-serum free medium with 1% FBS, glutamine, penicillin/streptomycin and 5 ng/ml nmGM-CSF.

Phagocytosis assay. For initial screening, all antibodies were tested at a concentration of 10 µg/ml. For selected antibodies, a full range of dose-response curves was generated. Briefly, a 10 µm cryostat section of 19-24 month-old Tg2576 mouse or human AD brains were thawed and mounted onto poly-lysine coated glass coverslips and placed in wells of 24-well tissue culture plates. The coverslips were washed twice with the assay medium. Control or anti-Aβ antibodies were added at 2× final concentration in the 0.15 ml assay medium for 1 hour at incubator (37° C., 5% $CO_2$). 0.15 ml of microglial cells (primary microglia or IC-21 cells) were then seeded at a density of $1.6 \times 10^6$ cells/ml assay medium. The cultures were incubated in a humidified incubator (37° C., 5%

$CO_2$) for 24 hours or more. At the end of the incubation, the same volume of 8% paraformaldehyde/0.2 M phosphate buffer, pH 7.2, was added to fix the section for 1 hour. Sections were then incubated with blocking solution consisting of 3% normal goat serum (Vector, Burlingame, Calif.) and 0.3% Triton-X100 at room temperature for 1 hour and stained with biotinylated 6E10 (Senetek, St. Louis, Mo.) and rat anti-CD45 (or rat anti-CD11b and rat anti-F4/80, Serotec, Raleigh, N.C.) followed by a streptavidin-FITC (Vector Labs, Burlingame, Calif.) and goat anti-rat IgG-Cy3 or rat anti-rat IgG-texas red (Jackson ImmunoResearch, West Grove, PS). The sections were observed, and photographed with a confocal microscope (Nikon) using SimplePCI software (Compix Inc., PA). Amyloid plaques (diameter of 10-100 μm), microglia (diameter of 10-20 μm) and internalized amyloid (green inside red ring representing microglia surface stain) can easily be distinguished by using confocal microscopy with optical planes of 0.5 μm thickness.

Analysis. For quantification of phagocytosis, one brain section per concentration point was used, covering antibody concentrations in the range of 0.001-30 μg/ml. 50-100 cortical plaques were examined at 40× magnification, and both, partially and completely internalized plaques were counted as positive events. The percentage of plaques being phagocytosed was calculated and plotted over the antibody concentration. Determination of $EC_{50}$, defined as the concentration of test antibody at which 50% of plaques count as positive events as described above, together with a maximum percentage reached at 10 μg/ml, allowed ranking of antibodies with regard to phagocytic potency. Data were plotted and $EC_{50}$ values were determined by using the Prism software v4.01 (GraphPad, San Diego, Calif.).

Amyloid plaques remained intact and no phagocytosis was observed in the presence of 10 μg/ml mouse IgG. In contrast, after incubation of adjacent sections in the presence of 10 μg/ml mAb 2.1 and 10G4, extracellular amyloid deposits were almost completely resolved and instead were localized within the microglial cells. The phagocytic activities of IC-21 cell line, primary mouse microglia and one human microglial cell lines were similar.

To confirm that this was internalization, confocal microscopy was used to scan serially focal planes of 0.5 μm thickness from top to bottom of plaques at 40× objective. The Z-series of optical planes showed that in the presence of 10 μg mAb 2.1, microglia engulfed all amyloid; however, in the presence of mouse IgG control antibody, exogenous microglial cells remained in a confocal plane above the tissue section and contained no amyloid deposits, whereas amyloid remained in the plaques with the tissue plane. These results demonstrate that mAb 2.1 and mAb 10G4 had the ability to trigger phagocytosis of amyloid and lead to amyloid clearance.

In order to quantify antibody induced phagocytosis of amyloid, an ex vivo phagocytosis experiment was performed on four different mouse antibodies mAb 2.1, mAb 10G4, mAb 6E10 and mAb 4G8 in full concentration titration (0.001, 0.01, 0.1, 0.25, 1, 5, and 10 μg/ml). Phagocytic events were defined as partially and completely internalized amyloid plaques as described above. The percentage of plaques being phagocytosed was calculated and plotted over the antibody concentration. In the presence of control mouse IgG, no phagocytosis was seen. $EC_{50}$ values ranked antibodies with regard to phagocytic potency as follows: 2.1>4G8>10G4>6E10, with $EC_{50}$ values of 0.4, 0.8, 1.6 and 5.0 μg/ml, respectively.

The ability of mAb 2.1 to induce amyloid phagocytosis over time was assessed by comparing the internalized peptide fluorescent intensity in the microglia and plaque number in the sections. Adjacent sections of 24-month old Tg2576 mouse were incubated with 10 μg/ml mAb 2.1 in the presence of primary microglia for various times. After 6-hour incubation of mAb 2.1, at a time that no phagocytosis had yet occurred, amyloid plaques remained intact. At 24 hours, amyloid localized within microglial cells, but plaque number in the section was not changed by that time, compared with control antibody. The internalized amyloid and plaque number in the section dramatically declined at day 3 and day 6. By day 9, the internalized amyloid fluorescence in the microglia had completely faded, and the plaques in the section were absent (See Table 7 below). The same results were obtained from incubation with 10G4. There was no degradation of amyloid deposits in the sections with control mouse IgG. Thus in contrast to what has been reported for amyloid with other microglial scavenging pathways (Parasce et al., *J. Biol. Chem.*, 272:29390-29397 (1997); Chung et al., *J. Biol. Chem.*, 274:32301-32308 (1999)), antibody-mediated phagocytosis of amyloid led to its degradation.

TABLE 7

| Degradation of internalized amyloid deposits | | |
| --- | --- | --- |
| Time (day) | plaques/section | % |
| irre. Antibody | 100 | 100 |
| 0.4 | 100 | 100 |
| 1 | 100 | 100 |
| 3 | 65 | 65 |
| 6 | 14 | 14 |
| 9 | 0 | 0 |

The ex vivo phagocytosis study described above was also performed with humanized antibody candidates on brain sections of 24-month old Tg2576 mouse with 2.1 chimera, 2.1 J, 2.1 K, 2.1 A, and 2.1 N in full concentration titration (0.01, 0.1, 1, 3, 10 and 30 μg/ml). 2.1 chimera and all humanized 2.1 antibodies tested, except 2.1 N, induced phagocytosis.

The ex vivo phagocytosis study described above was repeated using various humanized versions of anti-Aβ antibodies (2.1 chimera, 2.1 E, 2.1 G, 2.1 E K5, 2.1E K5R, 2.1 G K5, 2.1, G K5R, 2.1 I K5R and 2.1 L) on fresh unfixed brain sections of a 22 month-old Tg2576 mouse containing a substantial amount of amyloid plaques. Table 8 summarizes the results of both assays.

TABLE 8

| Antibody | $EC_{50}$ (μg/ml) |
| --- | --- |
| 2.1 chimera | 0.8 |
| 2.1 L | 0.82 |
| 2.1 K | 0.84 |
| 2.1 J | 1.22 |
| 2.1 Chimera (293) | 1.08 |
| 2.1 Chimera (CHO) | 0.70 |
| 2.1 L | 0.73 |
| 2.1 A | 0.83 |
| 2.1 I K5R | 0.69 |
| 2.1 E K5 | 3.94 |
| 2.1 E K5R | 2.23 |
| 2.1 G K5 | 1.78 |
| 2.1 G K5R | 0.94 |

Another ex vivo phagocytosis assay was performed to determine if humanized 2.1 antibodies could induce phagocytosis on IC-21 cells on the brain sections of a 91-year old AD patient. At 10 μg/ml, 2.1 chimera, 2.1 A, and 2.1 K, all resulted in complete phagocytosis, showing all amyloid deposits localized within microglial cells. 2.1 chimera, 2.1 A and 2.1 K triggered the phagocytosis in a concentration dependent fashion, with $EC_{50}$ values of 0.72, 0.72 and 0.76 µg/ml, respectively. These results demonstrated that the phagocytic activity on the human AD brain and on the Tg2576 mouse brain was similar.

The mechanism of the antibody-dependent phagocytosis is thought to be mediated by the Fc receptor. However, it is reported that antibody-induced phagocytosis can also be obtained in vivo by mechanisms that are independent of Fc mediation. An additional possibility for plaque clearance involves activation of complement systems that could enhance clearance or degradation. The ex vivo phagocytosis assay described above was used to examine these mechanisms. Fab fragments of mAb 2.1 and mAb 10G4 were prepared and used for ex vivo phagocytosis assay. Although the antibody Fab fragments of mAb 2.1 and mAb 10G4 retained their full ability to react with plaques, phagocytic ability at 10 µg/ml declined from 98% of original mAb 2.1 and mAb 10G4 to 18% and 24%, respectively.

The function of Fc receptor with primary microglia from FcR knockout (FcRγ$^{-/-}$) mice were also studied. In the presence of wild type microglia, 10 µg/ml of in Ab 2.1 triggered complete phagocytosis on the brain sections of 19-month-old Tg2576 mouse. However, in the presence of FcRγ$^{-/-}$ microglia, no phagocytosis was seen in the sections incubated with 10 µg/ml mAb 2.1. Quantitative assessment of the phagocytosis of amyloid showed that deficit in FcR completely abolished phagocytic ability of microglia. Taken together with data from Fab of mAb 2.1, these results demonstrated that phagocytosis in the ex vivo assay was mediated by the Fc receptor.

Functional activity of 2.1A, and mAb 10G4 was characterized by the ex vivo phagocytosis assay described above. Results indicated that phagocytosis in ex vivo was antibody-dependent, and FcR mediated. The phagocytosed amyloid was subsequently degraded. mAb 2.1 and mAb 10G4 had strong phagocytic potency with $EC_{50}$s of 0.4 and 1.6 µg/ml; respectively. 2.1A had powerful phagocytic ability with $EC_{50}$ of 0.75 µg/ml (average on Tg2576 and human AD brain).

Example 6

Anti-Amyloid (mAb 2.1 and mAb 10G4) Treatment of APP Transgenic Tg2576 Mice

The ability of peripherally administered anti-Aβ antibodies 2.1 and 10G4 to reduce amyloid plaque burden was evaluated in APP transgenic Tg2576 mice overexpressing Aβ.

Treatment: At 7.5 to 8 months of age, mice were treated weekly through IP route with PBS as vehicle, murine monoclonal anti-Aβ 2.1 IgG, or murine monoclonal anti-Aβ 10G4 IgG. The dose used was 15 mg IgG per kg of body weight for both antibodies at the volume of 5 mL/kg. The duration of treatment was 24 weeks.

TABLE 9

| Group No. | Test article | Male (n) | Female (n) | Route | Dose (mg/kg) | Volume (mL/kg) | Dosing Schedule |
|---|---|---|---|---|---|---|---|
| 1 | PBS | 5 | 6 | IP | 0 | 5 | Weekly |
| 2 | mAb 2.1 | 6 | 6 | IP | 15 | 5 | Weekly |
| 3 | mAb 10G4 | 5 | 5 | IP | 15 | 5 | Weekly |

The number of animals listed in the preceding table is the number of animals used in the beginning of the study. In the PBS control group, 1 male and 1 female mouse died during the study. In the 2.1 treatment group, 2 males and 2 females died, and in the 10G4 treatment group 1 male mouse died during the study. The death rate was consistent with the normal rate for this line of transgenic animals and was unrelated to the experimental treatment.

PK Sampling: Blood samples (50-100 µL) for PK analysis were collected from 5 mice from the mAb 2.1 group into serum separator tubes (Microtainer Brand) through the tail vein at pre-dose, 24 hrs after the 1$^{st}$ dose, and 7 days post-dose for weeks 2, 4, 6, 10, 14, 18, and 22. PK samples were also collected from 5 mice in the mAb 10G4 group at pre-dose, 24 hrs after the 1$^{st}$ dose, and 7 days post-dose for weeks 2 and 22. (With the exception of the 24 hr post-dose timepoint, all PK samples were taken just prior to the next dose.) At the end of 24 weeks (7 days after the final dose), animals were euthanized by $CO_2$ inhalation followed immediately by the collection from both dose groups of approximately 1 mL of blood through cardiopuncture into a serum separator tube (Microtainer Brand) for PK analysis. (No PK samples were taken from the PBS group.) Serum samples were prepared and stored at −80° C. until analysis for levels of test article by time-resolved fluorescence immunoassay.

Brain Dissection: Following the blood collection, the brain was dissected out from the skull and bisected at the mid-line. Half of the brain was frozen on dry ice for future biochemical study and the other half was embedded in OCT embedding medium and frozen on dry ice for histology studies.

Histology: 14 mm-thick fresh frozen coronal serial sections were cut in a cryostat microtome. Sections were thaw-mounted onto Fisher "plus" microscope slides and air-dried. Sections were stored at −20° C. until use. At the time of staining, sections were warmed to room temperature and fixed in 4% paraformaldehyde/0.1 M phosphate buffer, pH 7.2, for 1 hr. The endogenous tissue peroxidase activity was destroyed by incubating with 3% $H_2O_2$ in PBS for 20 min. Sections were then incubated with 88% formic acid for 20 min to expose Aβ epitope and then with blocking solution (3% normal goat serum/5% normal horse serum/0.25% carrageenan lambda/0.1% triton/PBS) for 1 hr. Sections were incubated with 0.5 µg/mL biotinylated anti-human Aβ monoclonal antibody 4G8 (Senetek, St. Louis, Mo.) or a control biotinylated mouse myeloma IgG (Sigma, St. Louis, Mo.) in the above blocking solution at 4° C. overnight. The antigen was detected by ABC/DAB protocol as described in Yan et al., *J. Comp. Neurol.*, 378:135-157 (1997). Sections were dehydrated and cover-slipped with mounting medium. Some sections were used for thioflavine-S staining according to standard histology protocol to detect fibril form of amyloid plaques in the brain parenchyma and amyloid plaque associated with cerebral blood vessels (cerebral amyloid angiopathy, CAA).

In vivo phagocytosis: The brain sections were fixed with 4% paraformaldehyde for 1 hr followed by incubation with blocking solution (same as above) for 1 hr. The sections were then incubated overnight with 10 µg/mL of biotinylated-6E10 (Senetek, St. Louis; MO) and rabbit anti-CSF-1R antiserum (Upstate, Lake Placid, N.Y.) diluted 1:250. The sections were stained with streptavidin-FITC (diluted 1:200) and goat anti-rabbit IgG-Texas Red (Vector Lab, Burlingame, Calif.) (diluted 1:200). The sections were then analyzed using a confocal microscope.

Morphological data analysis: Stained sections were examined under a light microscope. Digital images were taken under the microscope equipped with a digital camera. For amyloid plaque burden, the images were analyzed with Meta-Morph software (Universal Imaging Corp., West Chester, Pa.). Seven sections (1 out of every 5 serial sections) of each animal containing cingulate cortex (between Bregma 1.54 mm to −0.1 mm) (Franklin et al., The Mouse Brain in Stereotaxic Coordinates, 1997) and 8 sections of each animal containing hippocampus (between Bregma −1.7 mm to −2.8 mm) were used for the analysis. The area of interest was manually outlined under 4× magnification. The software was programmed to measure the number of plaques, the average size of plaques and the integrated plaque staining gray scale. The percentage of area covered by plaques named as plaque burden was calculated by the following formula:

$$\frac{\text{\# of plaques} \times \text{Avg. size of plaques}}{\text{Area of interest}} \times 100\%$$

For the characterization of cerebral amyloid angiopathy (CAA), 5 brain sections between Bregma 1.34 mm to −2.8 mm from each animal were used. Blood vessels within the cerebral cortex of the whole hemisphere with clear Aβ immunostaining were counted as positive CAA events. Similar quantification was done in another set of sections stained with thioflavine-S. The frequency of CAA was calculated by dividing the total number of CAA positive events in the cortex region by the number of sections used.

All the quantitative results were analyzed by one-way ANOVA test followed by Newman-Keuls test using Prism software version 4.01 (GraphPad Software, San Diego, Calif.). All results were expressed as the mean±error of mean. The p>0.05 was used to determine significant differences between the monoclonal antibodies 2.1 or 10G4 and the PBS control.

Murine monoclonal anti-Aβ 2.1 and 10G4 were tested in Tg2576 mice for their ability to block or reduce the age-dependent amyloid plaque accumulation in these animals. Little or no plaques were present in the brains of Tg2576 mice at age 7.5-8 months, the starting point of the treatment. By the end of the treatment at age 13:5-14 months, substantial numbers of amyloid plaques existed in the cortex and hippocampus of these animals. PBS control animals displayed plaque pathology typically seen at this age. By visual inspection, the treatment with 2.1 and 10G4 reduced the number of the plaques. Interestingly, the morphology of remaining plaques was changed in that satellite deposits were reduced and the neuritic plaques were reshaped into smooth, round structures.

To better quantify the reduction of amyloid plaques, quantitative morphological analysis in the cingulate cortex, piriform cortex, and hippocampus was performed. The plaque burden in both cingulate and piriform cortex was decreased 58-61% by the treatment of mouse monoclonal antibody 2.1 and 34% by mouse monoclonal antibody 10G4.

The plaque burden in the hippocampus was not changed by treatment with either antibody. This might be due to the relatively lower level of plaque burden seen in the hippocampus at this age.

The anti-Aβ immunohistochemical staining used here detects both the diffuse form and dense fibril form of amyloid deposits. Thioflavine-S stains only the dense fibril amyloid plaques. By manual counting of thioflavine S positive stained plaques, we found that injection of 2.1 and 10G4 reduced dense-cored plaques by 55% (p<0.01) and 25% (p>0.05, not statistically significant), respectively.

The ability of activated microglia to phagocytose Aβ after the treatment of anti-amyloid antibody under the in vivo situation was studied. Sections from the three treatment groups were double stained with a plaque marker and an activated microglial marker and then examined under a confocal microscope. In the PBS-injected group, Aβ deposits remained intact and there was no indication of phagocytosis. In contrast, in both mAb 2.1- and mAb 10G4-treated groups, there was clear evidence that Aβ deposits had been phagocytosed by microglia. This observation is consistent with the data from the ex vivo phagocytosis assay illustrated in Example 5 and directly supports the proposed critical role played by microglia in removal of amyloid plaques.

In addition to brain parenchyma amyloid plaques, amyloid can also be deposited around the cerebral blood vessels resulting in cerebral amyloid angiopathy (CAA) (Vinters, H., *Stroke,* 18:311-324 (1987). In the anti-Aβ immunostained Tg2576 mouse brains, blood vessels surrounded by amyloid deposit (CAA) were identified. By visual inspection of antibody-stained sections, the frequency of CAA was not changed with the antibody treatments. The quantitative analysis was performed by manual counting of Aβ positively staining CAA. There were no significant changes in CAA frequency among the groups.

PK samples were analyzed for serum levels of mAb 2.1 or mAb 10G4 using time-resolved fluorescence immunoassay (LOQ=0.04 μg/mL or 0.08 μg/mL, respectively). Results indicated that mAb 2.1 and mAb 10G4 were present in the serum.

The above example indicates that prophylactic treatment with anti-Aβ antibodies 2.1 before onset of plaque burden results in reduced amyloid plaque burden. The above example also indicates that treatment with anti-Aβ antibodies 2.1 and 110G4 resulted in reduced amyloid plaque burden in the frontal cortex of Tg2576 mice but had little effect on CAA.

Example 7

Treatment of APP Transgenic Tg2576 Mice with mAb 2.1 IgG

The ability of peripherally administered anti-Aβ antibody 2.1 to reduce amyloid plaque burden was evaluated in APP transgenic Tg2576 mice overexpressing Aβ.

Treatment: 9 month-old Tg2576 mice were treated weekly through i.p. route with murine monoclonal anti-Aβ 2.1 IgG in PBS at doses of 0 (started with 4 males, 6 females, 2 females died), 1.5 (started with 2 males, 8 females, 1 male and 1 female died); 4.5 (started with 4 males, 6 females, no death), 15 (started with 4 males, 6 females, 2 males and 1 female died), and 45 mg/kg (started with 4 males, 6 females, 1 male and 1 female died) in the volume of 5 ml/kg. The duration of treatment was 24 weeks. Blood samples (50-100 μl) were collected through tail vein at pre-dose, 4 hours after the 1st, 8th, 16th, 24th injections and one time just before the $24^{th}$ injection, 6 time points in total. Seven days after the $24^{th}$ injection, CSF and blood from cardiac puncture was collected.

Brain Dissection: All the animals were flushed with 5 ml of saline through the heart. The brain was then dissected out from the skull and bisected at the mid-line. Half of the brain was frozen on dry ice for future biochemical study and the other half was embedded in OCT tissue medium and then frozen on dry ice for histology studies.

Histology: 14 μm-thick fresh frozen coronal serial sections were cut in a cryostat microtome. Sections were thaw mounted onto the Fisher "plus" microscope slides and air-dried. Sections were stored at −20° C. until use. At the time of staining, sections were warmed to room temperature and fixed in 4% paraformaldehyde/0.1 M phosphate buffer, pH 7.2 for 1 hr. The endogenous tissue peroxidase activity was destroyed by incubating with 3% $H_2O_2$ in PBS for 20 min. Sections were then incubated with 88% formic acid for 20 min to expose Aβ epitope and then with blocking solution (3% normal goat serum/5% normal horse serum/0.25% carrageenan lambda/0.1% triton/PBS) for 1 hr. Sections were incubated with 0.5 μg/ml biotinylated anti-human Aβ monoclonal antibody 4G8 or a control mouse myeloma IgG (Sigma, St. Louis, Mo.) in the above blocking solution at 4° C. over night. The antigen was detected by ABC/DAB protocol as described (Yan et al., 1997). Sections were dehydrated and cover-slipped with mounting medium.

Morphological data analysis: Stained sections were examined under a light microscope. Digital images were taken under the microscope equipped with a digital camera. For amyloid plaque burden, the images were analyzed with Meta-Morph software (Universal Imaging Corp., West Chester, Pa.). Seven sections (1 out of every 5 serial sections) of each animal containing cingulate cortex (between Bregma 1.54 mm to −0.11 mm) (Franklin and Paxinos, 1997) and 8 sections of each animal containing hippocampus (between Bregma −1.7 mm to −2.8 mm) were used for the analysis. The area of interest was manually outlined under 4× magnification. The software was programmed to measure the numbers of plaques, the average size of plaques and the integrated plaque staining gray scale. The percentage of area covered by plaques was calculated by multiplying the number of plaques with the average size of plaques divided by the area of interest and time 100.

Data analysis: All the quantitative results were analyzed by one-way ANOVA test and followed by Donett t test.

FIG. 2 shows quantitative morphological analysis of the plaque burden in cingulate cortex. Only the treatment of 45 mg/k resulted in a significant reduction of plaque burden (50% reduction vs, PBS, p<0.05). The plaque burden in the hippocampus shows a trend of reduction with increased dosage of 2.1 treatment, but did not reach the statistically significant level.

The above assay was repeated with a more frequent dosing regimen of 3× per week. Compared with PBS treatment, 1.5 mg/kg mAb 2.1 treatment resulted in a significant (p=0.007) 44% plaque burden reduction in the cingulate cortex (FIG. 3). In these same animals, mAb 2.1 treatment resulted in 32% plaque burden reduction in the hippocampus but that did not reach statistical significance (p=0.056).

All of the above U.S. patents, U.S. patent application publications, U.S. patent applications, foreign patents, foreign patent applications and non patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention.

What is claimed is:

1. A humanized antibody that binds amyloid-beta, comprising:
    a heavy chain comprising a variable region that has an amino acid sequence 90% or more identical to the variable region amino acid sequence set forth in SEQ ID NO: 8; and
    a light chain, wherein the light chain comprises a CDR1, a CDR2, and a CDR3 comprising SEQ ID NOS: 12, 13, and 14, respectively.

2. The humanized antibody of claim 1, wherein at least one amino acid residue of the variable region of the heavy chain is a conservative substitution of the corresponding amino acid in SEQ ID NO: 8.

3. The humanized antibody of claim 1, wherein at least one amino acid residue of the variable region of the heavy chain is an alternative human framework amino acid corresponding to that position in SEQ ID NO: 8.

4. The humanized antibody of claim 3, wherein the human framework amino acid is from a human antibody sequence, a human germline antibody sequence, or a human consensus antibody sequence.

5. The humanized antibody of claim 1, that comprises the variable region amino acid sequence set forth in SEQ ID NO: 8.

6. The humanized antibody of any one of claim 1, wherein the light chain comprises an amino acid sequence 65% or more identical to the amino acid sequence set forth in SEQ ID NO: 6.

7. The humanized antibody of claim 6 that retains the amino acid residues at positions 36, 37 and 46 of SEQ ID NO: 6.

8. The humanized antibody of claim 6, wherein the light chain comprises an amino acid sequence 80% or more identical to the amino acid sequence set forth in SEQ ID NO: 6.

9. The humanized antibody of claim 8, wherein the light chain comprises an amino acid sequence 90% or more identical to the amino acid sequence set forth in SEQ ID NO: 6.

10. The humanized antibody of claim 9 that comprises the amino acid sequence set forth in SEQ ID NO: 6.

11. The humanized antibody of claim 6, wherein at least one amino acid is a conservative substitution of the corresponding amino acid in SEQ ID NO: 6.

12. The humanized antibody of claim 6, wherein at least one amino acid is an alternative human framework amino acid corresponding to that position in SEQ ID NO: 6.

13. The humanized antibody of claim 12, wherein the human framework amino acid is from a human antibody sequence, a human germline antibody sequence, or a human consensus antibody sequence.

14. The humanized antibody of claim 1 that is an antibody comprising the light chain amino acid sequence set forth in SEQ ID NO: 6 and the heavy chain amino acid sequence set forth in SEQ ID NO: 8.

15. The humanized antibody of claim 1 that exhibits an avidity $k_d$ for amyloid-beta of lower than $10^{-2}$, as determined by surface plasmon resonance analysis.

16. The humanized antibody of claim 15, wherein the antibody class is IgG.

17. A nucleic acid encoding the humanized antibody of claim 1.

18. The nucleic acid of claim 17, comprising the nucleic acid sequence set forth in SEQ ID NO: 5 and the nucleic acid sequence set forth in SEQ ID NO: 7.

19. A vector comprising the nucleic acid of claim 17 or 18.

20. A host cell comprising the vector of claim 19.

21. A method of producing a humanized antibody that binds amyloid beta and comprises:
 a heavy chain comprising a variable region at least 90% identical to the amino acid sequence set forth in SEQ ID NO:8; and
 a light chain comprising each of SEQ ID NOS: 12, 13, and 14,
 wherein the method comprises culturing the host cell of claim 20 such that the nucleic acid is expressed to produce the humanized antibody.

22. The method of claim 21, further comprising the step of recovering the humanized antibody from the host cell culture.

* * * * *

SEQUENCE LISTING

```
<160> NUMBER OF SEQ ID NOS: 52

<210> SEQ ID NO 1
<211> LENGTH: 714
<212> TYPE: DNA
<213> ORGANISM: Mus musculus
<220> FEATURE:
<221> NAME/KEY: misc_feature
<223> OTHER INFORMATION: mAb 2.1 light chain

<400> SEQUENCE: 1
atgaagttgc ctgttaggct gttggtgctg atgttctgga ttcctgcttc cagcagtgat      60
gttttgatga cccaaactcc actctccctg cctgtcagtc ttggagatca agcctccatc     120
tcttgcagat ctagtcagag cattgtacat agtaatggaa acacctattt agaatggtac     180
ctgcagaaac caggccagtc tccaaagctc ctgatctaca agtttccaa ccgattttct      240 ggggtcccag acaggttcag tggcagtgga tcagggacag atttcacact caagatcagc     300
agagtggagg ctgaggatct gggagtttat tactgctttc aaggttcaca tgttccgctc     360
acgttcggtg ctgggaccaa gctggagctg aaacgggctg atgctgcacc aactgtatcc     420
atcttcccac catccagtga gcagttaaca tctggaggtg cctcagtcgt gtgcttcttg     480
aacaacttct accccaaaga catcaatgtc aagtggaaga ttgatggcag tgaacgacaa     540
aatggcgtcc tgaacagttg gactgatcag gacagcaaag acagcaccta cagcatgagc     600
agcaccctca cgttgaccaa ggacgagtat gaacgacata cagctatac ctgtgaggcc      660 actcacaaga tcaacttc acccattgtc aagagcttca caggaatga gtgt              714

<210> SEQ ID NO 2
<211> LENGTH: 238
<212> TYPE: PRT
<213> ORGANISM: Mus musculus
<220> FEATURE:
```

```
<221> NAME/KEY: MISC_FEATURE
<223> OTHER INFORMATION: mAb 2.1 light chain

<400> SEQUENCE: 2

Met Lys Leu Pro Val Arg Leu Leu Val Leu Met Phe Trp Ile Pro Ala
1               5                   10                  15

Ser Ser Ser Asp Val Leu Met Thr Gln Thr Pro Leu Ser Leu Pro Val
                20                  25                  30

Ser Leu Gly Asp Gln Ala Ser Ile Ser Cys Arg Ser Ser Gln Ser Ile
            35                  40                  45

Val His Ser Asn Gly Asn Thr Tyr Leu Glu Trp Tyr Leu Gln Lys Pro
50                      55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Tyr Cys
            100                 105                 110

Phe Gln Gly Ser His Val Pro Leu Thr Phe Gly Ala Gly Thr Lys Leu
        115                 120                 125

Glu Leu Lys Arg Ala Asp Ala Ala Pro Thr Val Ser Ile Phe Pro Pro
130                 135                 140

Ser Ser Glu Gln Leu Thr Ser Gly Gly Ala Ser Val Val Cys Phe Leu
145                 150                 155                 160

Asn Asn Phe Tyr Pro Lys Asp Ile Asn Val Lys Trp Lys Ile Asp Gly
                165                 170                 175

Ser Glu Arg Gln Asn Gly Val Leu Asn Ser Trp Thr Asp Gln Asp Ser
            180                 185                 190

Lys Asp Ser Thr Tyr Ser Met Ser Ser Thr Leu Thr Leu Thr Lys Asp
        195                 200                 205

Glu Tyr Glu Arg His Asn Ser Tyr Thr Cys Glu Ala Thr His Lys Thr
210                 215                 220

Ser Thr Ser Pro Ile Val Lys Ser Phe Asn Arg Asn Glu Cys
225                 230                 235

<210> SEQ ID NO 3
<211> LENGTH: 1392
<212> TYPE: DNA
<213> ORGANISM: Mus musculus
<220> FEATURE:
<221> NAME/KEY: misc_feature
<223> OTHER INFORMATION: mAb 2.1 heavy chain

<400> SEQUENCE: 3
atggacaggc ttacttcctc attcctgctg ctgattgtcc ctgcatatgt cttgtcccaa      60
gttactctaa aagagtctgg ccctgggata ttgaagccct cacagaccct cagtctgact     120
tgttctttct ctgggttttc actgagaact tctggtatgg gtgtaggctg gattcgtcag     180
ccttcaggga agggtctgga gtggctggca cacatttggt gggatgatga taagtcctat     240
aacccatccc tgaagagcca gctcacaatc tccaaggata cctccagaaa ccaggtattc     300
ctcaagatca ccagtgtgga cactgcagat actgccactt actactgtgc tcgaggaac     360 tattattacg acgactactt tgcctactgg ggccaaggca ccactctcac agtctcctca     420
gccaaaacga caccccccatc tgtctatcca ctggcccctg gatctgctgc ccaaactaac     480
tccatggtga ccctgggatg cctggtcaag ggctatttcc ctgagccagt gacagtgacc     540
tggaactctg gatccctgtc agcggtgtg cacaccttcc cagctgtcct gcagtctgac     600
```

```
ctctacactc tgagcagctc agtgactgtc ccctccagca cctggcccag cgagaccgtc    660
acctgcaacg ttgcccaccc ggccagcagc accaaggtgg acaagaaaat tgtgcccagg    720
gattgtggtt gtaagccttg catatgtaca gtcccagaag tatcatctgt cttcatcttc    780
cccccaaagc ccaaggatgt gctcaccatt actctgactc ctaaggtcac gtgtgttgtg    840
gtagacatca gcaaggatga tcccgaggtc cagttcagct ggtttgtaga tgatgtggag    900
gtgcacacag ctcagacgca accccgggag gagcagttca cagcactttt ccgctcagtc    960
agtgaacttc ccatcatgca tcaggactgg ctcaatggca aggagttcaa atgcagggtc   1020
aacagtgcag ctttccctgc ccccatcgag aaaaccatct ccaaaaccaa aggcagaccg   1080
aaggctccac aggtgtacac cattccacct cccaaggagc agatggccaa ggataaagtc   1140
agtctgacct gcatgataac agacttcttc cctgaagaca ttactgtgga gtggcagtgg   1200
aatgggcagc cagcggagaa ctacaagaac actcagccca tcatggacac agatggctct   1260
tacttcgtct acagcaagct caatgtgcag aagagcaact gggaggcagg aaatactttc   1320
acctgctctg tgttacatga gggcctgcac aaccaccata ctgagaagag cctctcccac   1380
tctcctggta aa                                                       1392

<210> SEQ ID NO 4
<211> LENGTH: 464
<212> TYPE: PRT
<213> ORGANISM: Mus musculus
<220> FEATURE:
<221> NAME/KEY: MISC_FEATURE
<223> OTHER INFORMATION: mAb 2.1 heavy chain

<400> SEQUENCE: 4

Met Asp Arg Leu Thr Ser Ser Phe Leu Leu Leu Ile Val Pro Ala Tyr
1               5                   10                  15

Val Leu Ser Gln Val Thr Leu Lys Glu Ser Gly Pro Gly Ile Leu Lys
            20                  25                  30

Pro Ser Gln Thr Leu Ser Leu Thr Cys Ser Phe Ser Gly Phe Ser Leu
        35                  40                  45

Arg Thr Ser Gly Met Gly Val Gly Trp Ile Arg Gln Pro Ser Gly Lys
    50                  55                  60

Gly Leu Glu Trp Leu Ala His Ile Trp Trp Asp Asp Lys Ser Tyr
65                  70                  75                  80

Asn Pro Ser Leu Lys Ser Gln Leu Thr Ile Ser Lys Asp Thr Ser Arg
                85                  90                  95

Asn Gln Val Phe Leu Lys Ile Thr Ser Val Asp Thr Ala Asp Thr Ala
            100                 105                 110

Thr Tyr Tyr Cys Ala Arg Arg Asn Tyr Tyr Asp Asp Tyr Phe Ala
        115                 120                 125

Tyr Trp Gly Gln Gly Thr Thr Leu Thr Val Ser Ser Ala Lys Thr Thr
    130                 135                 140

Pro Pro Ser Val Tyr Pro Leu Ala Pro Gly Ser Ala Ala Gln Thr Asn
145                 150                 155                 160

Ser Met Val Thr Leu Gly Cys Leu Val Lys Gly Tyr Phe Pro Glu Pro
                165                 170                 175

Val Thr Val Thr Trp Asn Ser Gly Ser Leu Ser Ser Gly Val His Thr
            180                 185                 190

Phe Pro Ala Val Leu Gln Ser Asp Leu Tyr Thr Leu Ser Ser Ser Val
        195                 200                 205

Thr Val Pro Ser Ser Thr Trp Pro Ser Glu Thr Val Thr Cys Asn Val
```

```
                    210                 215                 220
Ala His Pro Ala Ser Ser Thr Lys Val Asp Lys Ile Val Pro Arg
225                 230                 235                 240

Asp Cys Gly Cys Lys Pro Cys Ile Cys Thr Val Pro Glu Val Ser Ser
                    245                 250                 255

Val Phe Ile Phe Pro Pro Lys Pro Lys Asp Val Leu Thr Ile Thr Leu
                    260                 265                 270

Thr Pro Lys Val Thr Cys Val Val Val Asp Ile Ser Lys Asp Asp Pro
                    275                 280                 285

Glu Val Gln Phe Ser Trp Phe Val Asp Asp Val Glu Val His Thr Ala
                    290                 295                 300

Gln Thr Gln Pro Arg Glu Glu Gln Phe Asn Ser Thr Phe Arg Ser Val
305                 310                 315                 320

Ser Glu Leu Pro Ile Met His Gln Asp Trp Leu Asn Gly Lys Glu Phe
                    325                 330                 335

Lys Cys Arg Val Asn Ser Ala Ala Phe Pro Ala Pro Ile Glu Lys Thr
                    340                 345                 350

Ile Ser Lys Thr Lys Gly Arg Pro Lys Ala Pro Gln Val Tyr Thr Ile
                    355                 360                 365

Pro Pro Pro Lys Glu Gln Met Ala Lys Asp Lys Val Ser Leu Thr Cys
370                 375                 380

Met Ile Thr Asp Phe Phe Pro Glu Asp Ile Thr Val Glu Trp Gln Trp
385                 390                 395                 400

Asn Gly Gln Pro Ala Glu Asn Tyr Lys Asn Thr Gln Pro Ile Met Asp
                    405                 410                 415

Thr Asp Gly Ser Tyr Phe Val Tyr Ser Lys Leu Asn Val Gln Lys Ser
                    420                 425                 430

Asn Trp Glu Ala Gly Asn Thr Phe Thr Cys Ser Val Leu His Glu Gly
                    435                 440                 445

Leu His Asn His His Thr Glu Lys Ser Leu Ser His Ser Pro Gly Lys
    450                 455                 460

<210> SEQ ID NO 5
<211> LENGTH: 723
<212> TYPE: DNA
<213> ORGANISM: Homo sapiens
<220> FEATURE:
<221> NAME/KEY: misc_feature
<223> OTHER INFORMATION: AMG864 light chain

<400> SEQUENCE: 5
atggacatga ggctccctgc tcagctcctg ggctgctaa tgctctgggt cccaggatcc      60
agtggggatg ttctgatgac tcagtctcca ctctccctgc cgtcaccct tggacagccg     120 gcctccatct cctgcaggtc tagtcaaagc atcgtacaca gtaacggaaa cacctacttg     180
gagtggtatc tgcagaggcc aggccaatct ccaaagctcc taatttataa ggtttctaac     240
cggttctctg ggtcccaga cagattcagc ggcagtgggt caggcactga tttcacactg     300
aaaatcagca gggtggaggc tgaggatgtt ggggtttatt actgcttcca aggtagccac     360
gttcctctga cgttcggcgc agggaccaag ctggaaatca aacggactgt ggctgcacca     420
tctgtcttca tcttcccgcc atctgatgag cagttgaaat ctggaactgc ctctgttgtg     480
tgcctgctga ataacttcta tcccagagag gccaaagtac agtggaaggt ggataacgcc     540
ctccaatcgg gtaactccca ggagagtgtc acagagcagg acagcaagga cagcacctac     600
agcctcagca gcaccctgac gctgagcaaa gcagactacg agaaacacaa agtctacgcc     660
```

-continued

```
tgcgaagtca cccatcaggg cctgagctcg cccgtcacaa agagcttcaa caggggagag      720
tgt                                                                    723
```

<210> SEQ ID NO 6
<211> LENGTH: 241
<212> TYPE: PRT
<213> ORGANISM: Homo sapiens
<220> FEATURE:
<221> NAME/KEY: MISC_FEATURE
<223> OTHER INFORMATION: AMG864 light chain "rehumanized"

<400> SEQUENCE: 6

```
Met Asp Met Arg Leu Pro Ala Gln Leu Leu Gly Leu Leu Met Leu Trp
1               5                   10                  15

Val Pro Gly Ser Ser Gly Asp Val Leu Met Thr Gln Ser Pro Leu Ser
            20                  25                  30

Leu Pro Val Thr Leu Gly Gln Pro Ala Ser Ile Ser Cys Arg Ser Ser
        35                  40                  45

Gln Ser Ile Val His Ser Asn Gly Asn Thr Tyr Leu Glu Trp Tyr Leu
    50                  55                  60

Gln Arg Pro Gly Gln Ser Pro Lys Leu Leu Ile Tyr Lys Val Ser Asn
65                  70                  75                  80

Arg Phe Ser Gly Val Pro Asp Arg Phe Ser Gly Ser Gly Ser Gly Thr
                85                  90                  95

Asp Phe Thr Leu Lys Ile Ser Arg Val Glu Ala Glu Asp Val Gly Val
            100                 105                 110

Tyr Tyr Cys Phe Gln Gly Ser His Val Pro Leu Thr Phe Gly Ala Gly
        115                 120                 125

Thr Lys Leu Glu Ile Lys Arg Thr Val Ala Ala Pro Ser Val Phe Ile
    130                 135                 140

Phe Pro Pro Ser Asp Glu Gln Leu Lys Ser Gly Thr Ala Ser Val Val
145                 150                 155                 160

Cys Leu Leu Asn Asn Phe Tyr Pro Arg Glu Ala Lys Val Gln Trp Lys
                165                 170                 175

Val Asp Asn Ala Leu Gln Ser Gly Asn Ser Gln Glu Ser Val Thr Glu
            180                 185                 190

Gln Asp Ser Lys Asp Ser Thr Tyr Ser Leu Ser Ser Thr Leu Thr Leu
        195                 200                 205

Ser Lys Ala Asp Tyr Glu Lys His Lys Val Tyr Ala Cys Glu Val Thr
    210                 215                 220

His Gln Gly Leu Ser Ser Pro Val Thr Lys Ser Phe Asn Arg Gly Glu
225                 230                 235                 240

Cys
```

<210> SEQ ID NO 7
<211> LENGTH: 1410
<212> TYPE: DNA
<213> ORGANISM: Homo sapiens
<220> FEATURE:
<221> NAME/KEY: misc_feature
<223> OTHER INFORMATION: AMG864 heavy chain "humanized"

<400> SEQUENCE: 7

```
atggacacac tttgctccac gctcctgctg ctgaccatcc cttcatgggt cttgtcccag       60
gtcaccttga aggagtctgg tcctgcgctg gtgaaaccca cacagaccct cacgctgacc      120
tgcaccttct ctgggttctc actccgcact agtggaatgg gcgtgggctg gatccgtcag      180
cccccaggaa aggccctgga gtggcttgcc cacatttggt gggatgatga taagagctac      240
```

```
aacccatctc tgaagagcca gctcaccatc tctaaggaca cctccaaaaa ccaggtggtc    300
cttacaatga ccaacatgga ccctgtggac acagccacat attactgtgc acgcagaaac    360
tattactacg acgactactt cgcctactgg ggccagggca ccctggtcac cgtctctagt    420
gcctccacca agggcccatc ggtcttcccc ctggcaccct cctccaagag cacctctggg    480
ggcacagcgg ccctgggctg cctggtcaag gactacttcc ccgaaccggt gacggtgtcg    540
tggaactcag gcgccctgac cagcggcgtg cacaccttcc cggctgtcct acagtcctca    600
ggactctact ccctcagcag cgtggtgacc gtgccctcca gcagcttggg cacccagacc    660
tacatctgca acgtgaatca caagcccagc aacaccaagg tggacaagaa agttgagccc    720
aaatcttgtg acaaaactca cacatgccca ccgtgcccag cacctgaact cctgggggga    780
ccgtcagtct tcctcttccc cccaaaaccc aaggacaccc tcatgatctc ccggacccct    840
gaggtcacat gcgtggtggt ggacgtgagc cacgaagacc ctgaggtcaa gttcaactgg    900
tacgtggacg gcgtggaggt gcataatgcc aagacaaagc cgcgggagga gcagtacaac    960
agcacgtacc gtgtggtcag cgtcctcacc gtcctgcacc aggactggct gaatggcaag    1020
gagtacaagt gcaaggtctc caacaaagcc ctcccagccc ccatcgagaa aaccatctcc    1080
aaagccaaag ggcagccccg agaaccacag gtgtacaccc tgcccccatc ccgggatgag    1140
ctgaccaaga accaggtcag cctgacctgc ctggtcaaag gcttctatcc cagcgacatc    1200
gccgtggagt gggagagcaa tgggcagccg gagaacaact acaagaccac gcctcccgtg    1260
ctggactccg acggctcctt cttcctctat agcaagctca ccgtggacaa gagcaggtgg    1320
cagcagggga acgtcttctc atgctccgtg atgcatgagg ctctgcacaa ccactacacg    1380
cagaagagcc tctccctgtc tccgggtaaa    1410
```

<210> SEQ ID NO 8
<211> LENGTH: 470
<212> TYPE: PRT
<213> ORGANISM: Homo sapiens
<220> FEATURE:
<221> NAME/KEY: MISC_FEATURE
<223> OTHER INFORMATION: AMG864 heavy chain "humanized"

<400> SEQUENCE: 8

```
Met Asp Thr Leu Cys Ser Thr Leu Leu Leu Thr Ile Pro Ser Trp
1               5                   10                  15

Val Leu Ser Gln Val Thr Leu Lys Glu Ser Gly Pro Ala Leu Val Lys
            20                  25                  30

Pro Thr Gln Thr Leu Thr Leu Thr Cys Thr Phe Ser Gly Phe Ser Leu
        35                  40                  45

Arg Thr Ser Gly Met Gly Val Gly Trp Ile Arg Gln Pro Pro Gly Lys
    50                  55                  60

Ala Leu Glu Trp Leu Ala His Ile Trp Trp Asp Asp Lys Ser Tyr
65                  70                  75                  80

Asn Pro Ser Leu Lys Ser Gln Leu Thr Ile Ser Lys Asp Thr Ser Lys
                85                  90                  95

Asn Gln Val Val Leu Thr Met Thr Asn Met Asp Pro Val Asp Thr Ala
            100                 105                 110

Thr Tyr Tyr Cys Ala Arg Arg Asn Tyr Tyr Asp Asp Tyr Phe Ala
        115                 120                 125

Tyr Trp Gly Gln Gly Thr Leu Val Thr Val Ser Ser Ala Ser Thr Lys
    130                 135                 140

Gly Pro Ser Val Phe Pro Leu Ala Pro Ser Ser Lys Ser Thr Ser Gly
```

```
            145                 150                 155                 160
Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Leu Gly Thr Gln Thr Tyr Ile Cys Asn
    210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Asp Glu Leu Thr Lys Asn
    370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

Ser Leu Ser Pro Gly Lys
465                 470

<210> SEQ ID NO 9
<211> LENGTH: 7
<212> TYPE: PRT
<213> ORGANISM: Mus musculus
<220> FEATURE:
<221> NAME/KEY: MISC_FEATURE
<223> OTHER INFORMATION: CDR1 Heavy Chain

<400> SEQUENCE: 9

Thr Ser Gly Met Gly Val Gly
1               5

<210> SEQ ID NO 10
<211> LENGTH: 16
<212> TYPE: PRT
```

```
<213> ORGANISM: Mus musculus
<220> FEATURE:
<221> NAME/KEY: MISC_FEATURE
<223> OTHER INFORMATION: CDR2 Heavy Chain

<400> SEQUENCE: 10

His Ile Trp Trp Asp Asp Asp Lys Ser Tyr Asn Pro Ser Leu Lys Ser
1               5                   10                  15

<210> SEQ ID NO 11
<211> LENGTH: 11
<212> TYPE: PRT
<213> ORGANISM: Mus musculus
<220> FEATURE:
<221> NAME/KEY: MISC_FEATURE
<223> OTHER INFORMATION: CDR3 Heavy Chain

<400> SEQUENCE: 11

Arg Asn Tyr Tyr Tyr Asp Asp Tyr Phe Ala Tyr
1               5                   10

<210> SEQ ID NO 12
<211> LENGTH: 16
<212> TYPE: PRT
<213> ORGANISM: Mus musculus
<220> FEATURE:
<221> NAME/KEY: MISC_FEATURE
<223> OTHER INFORMATION: CDR1 Light Chain

<400> SEQUENCE: 12

Arg Ser Ser Gln Ser Ile Val His Ser Asn Gly Asn Thr Tyr Leu Glu
1               5                   10                  15

<210> SEQ ID NO 13
<211> LENGTH: 7
<212> TYPE: PRT
<213> ORGANISM: Mus musculus
<220> FEATURE:
<221> NAME/KEY: MISC_FEATURE
<223> OTHER INFORMATION: CDR2 Light Chain

<400> SEQUENCE: 13

Lys Val Ser Asn Arg Phe Ser
1               5

<210> SEQ ID NO 14
<211> LENGTH: 9
<212> TYPE: PRT
<213> ORGANISM: Mus musculus
<220> FEATURE:
<221> NAME/KEY: MISC_FEATURE
<223> OTHER INFORMATION: CDR3 Light Chain

<400> SEQUENCE: 14

Phe Gln Gly Ser His Val Pro Leu Thr
1               5

<210> SEQ ID NO 15
<211> LENGTH: 723
<212> TYPE: DNA
<213> ORGANISM: Homo sapiens
<220> FEATURE:
<221> NAME/KEY: misc_feature
<223> OTHER INFORMATION: >2.1 LC B DNA

<400> SEQUENCE: 15
atggacatga ggctccctgc tcagctcctg gggctgctaa tgctctgggt cccaggatcc      60
agtggggatg ttgtgatgac tcagtctcca ctctccctgc ccgtcaccct tggacagccg     120
```

-continued

```
gcctccatct cctgcaggtc tagtcaaagc atcgtacaca gtaacggaaa cacctacttg    180
gagtggtttg tgcagaggcc aggccaatct ccaagggtcc taatttataa ggtttctaac    240
cggttctctg gggtcccaga cagattcagc ggcagtgggt caggcactga tttcacactg    300
aaaatcagca gggtggaggc tgaggatgtt ggggtttatt actgcttcca aggtagccac    360
gttcctctga cgttcggcgg tgggaccaag ctggagatca aacgtacggt ggctgcacca    420
tctgtcttca tcttcccgcc atctgatgag cagttgaaat ctggaactgc ctctgttgtg    480
tgcctgctga ataacttcta tcccagagag gccaaagtac agtggaaggt ggataacgcc    540
ctccaatcgg gtaactccca ggagagtgtc acagagcagg acagcaagga cagcacctac    600
agcctcagca gcaccctgac gctgagcaaa gcagactacg agaaacacaa agtctacgcc    660
tgcgaagtca cccatcaggg cctgagctcg cccgtcacaa agagcttcaa caggggagag    720
tgt    723
```

```
<210> SEQ ID NO 16
<211> LENGTH: 241
<212> TYPE: PRT
<213> ORGANISM: Homo sapiens
<220> FEATURE:
<221> NAME/KEY: MISC_FEATURE
<223> OTHER INFORMATION: >2.1 LC B protein

<400> SEQUENCE: 16

Met Asp Met Arg Leu Pro Ala Gln Leu Leu Gly Leu Leu Met Leu Trp
1               5                   10                  15

Val Pro Gly Ser Ser Gly Asp Val Val Met Thr Gln Ser Pro Leu Ser
                20                  25                  30

Leu Pro Val Thr Leu Gly Gln Pro Ala Ser Ile Ser Cys Arg Ser Ser
            35                  40                  45

Gln Ser Ile Val His Ser Asn Gly Asn Thr Tyr Leu Glu Trp Phe Val
        50                  55                  60

Gln Arg Pro Gly Gln Ser Pro Arg Val Leu Ile Tyr Lys Val Ser Asn
65                  70                  75                  80

Arg Phe Ser Gly Val Pro Asp Arg Phe Ser Gly Ser Gly Ser Gly Thr
                85                  90                  95

Asp Phe Thr Leu Lys Ile Ser Arg Val Glu Ala Glu Asp Val Gly Val
            100                 105                 110

Tyr Tyr Cys Phe Gln Gly Ser His Val Pro Leu Thr Phe Gly Gly Gly
        115                 120                 125

Thr Lys Leu Glu Ile Lys Arg Thr Val Ala Ala Pro Ser Val Phe Ile
130                 135                 140

Phe Pro Pro Ser Asp Glu Gln Leu Lys Ser Gly Thr Ala Ser Val Val
145                 150                 155                 160

Cys Leu Leu Asn Asn Phe Tyr Pro Arg Glu Ala Lys Val Gln Trp Lys
                165                 170                 175

Val Asp Asn Ala Leu Gln Ser Gly Asn Ser Gln Glu Ser Val Thr Glu
            180                 185                 190

Gln Asp Ser Lys Asp Ser Thr Tyr Ser Leu Ser Ser Thr Leu Thr Leu
        195                 200                 205

Ser Lys Ala Asp Tyr Glu Lys His Lys Val Tyr Ala Cys Glu Val Thr
    210                 215                 220

His Gln Gly Leu Ser Ser Pro Val Thr Lys Ser Phe Asn Arg Gly Glu
225                 230                 235                 240

Cys
```

<210> SEQ ID NO 17
<211> LENGTH: 723
<212> TYPE: DNA
<213> ORGANISM: Homo sapiens
<220> FEATURE:
<221> NAME/KEY: misc_feature
<223> OTHER INFORMATION: >2.1 LC C DNA

<400> SEQUENCE: 17

```
atggacatga ggctccctgc tcagctcctg gggctgctaa tgctctgggt cccaggatcc      60
agtggggatg ttgtgatgac tcagtctcca ctctccctgc ccgtcaccct tggacagccg     120
gcctccatct cctgcaggtc tagtcaaagc atcgtacaca gtaacggaaa cacctacttg     180
gagtggtatc tgcagaggcc aggccaatct ccacagctcc taatttataa ggtttctaac     240
cggttctctg ggtcccaga cagattcagc ggcagtgggt caggcactga tttcacactg      300
aaaatcagca gggtggaggc tgaggatgtt ggggtttatt actgcttcca aggtagccac     360
gttcctctga cgttcggcca agggaccaag ctggaaatca aacgtacggt ggctgcacca     420
tctgtcttca tcttcccgcc atctgatgag cagttgaaat ctggaactgc ctctgttgtg     480
tgcctgctga ataacttcta tcccagagag gccaaagtac agtggaaggt ggataacgcc     540
ctccaatcgg gtaactccca ggagagtgtc acagagcagg acagcaagga cagcacctac     600
agcctcagca gcaccctgac gctgagcaaa gcagactacg agaaacacaa agtctacgcc     660
tgcgaagtca cccatcaggg cctgagctcg cccgtcacaa agagcttcaa caggggagag     720
tgt                                                                   723
```

<210> SEQ ID NO 18
<211> LENGTH: 241
<212> TYPE: PRT
<213> ORGANISM: Homo sapiens
<220> FEATURE:
<221> NAME/KEY: MISC_FEATURE
<223> OTHER INFORMATION: >2.1 LC C protein

<400> SEQUENCE: 18

```
Met Asp Met Arg Leu Pro Ala Gln Leu Leu Gly Leu Leu Met Leu Trp
1               5                   10                  15

Val Pro Gly Ser Ser Gly Asp Val Val Met Thr Gln Ser Pro Leu Ser
            20                  25                  30

Leu Pro Val Thr Leu Gly Gln Pro Ala Ser Ile Ser Cys Arg Ser Ser
        35                  40                  45

Gln Ser Ile Val His Ser Asn Gly Asn Thr Tyr Leu Glu Trp Tyr Leu
    50                  55                  60

Gln Arg Pro Gly Gln Ser Pro Gln Leu Leu Ile Tyr Lys Val Ser Asn
65                  70                  75                  80

Arg Phe Ser Gly Val Pro Asp Arg Phe Ser Gly Ser Gly Ser Gly Thr
                85                  90                  95

Asp Phe Thr Leu Lys Ile Ser Arg Val Glu Ala Glu Asp Val Gly Val
            100                 105                 110

Tyr Tyr Cys Phe Gln Gly Ser His Val Pro Leu Thr Phe Gly Gln Gly
        115                 120                 125

Thr Lys Leu Glu Ile Lys Arg Thr Val Ala Ala Pro Ser Val Phe Ile
    130                 135                 140

Phe Pro Pro Ser Asp Glu Gln Leu Lys Ser Gly Thr Ala Ser Val Val
145                 150                 155                 160

Cys Leu Leu Asn Asn Phe Tyr Pro Arg Glu Ala Lys Val Gln Trp Lys
```

```
                        165                 170                 175
Val Asp Asn Ala Leu Gln Ser Gly Asn Ser Gln Glu Ser Val Thr Glu
            180                 185                 190

Gln Asp Ser Lys Asp Ser Thr Tyr Ser Leu Ser Ser Thr Leu Thr Leu
            195                 200                 205

Ser Lys Ala Asp Tyr Glu Lys His Lys Val Tyr Ala Cys Glu Val Thr
            210                 215                 220

His Gln Gly Leu Ser Ser Pro Val Thr Lys Ser Phe Asn Arg Gly Glu
225                 230                 235                 240

Cys

<210> SEQ ID NO 19
<211> LENGTH: 723
<212> TYPE: DNA
<213> ORGANISM: Homo sapiens
<220> FEATURE:
<221> NAME/KEY: misc_feature
<223> OTHER INFORMATION: >2.1 LC D DNA

<400> SEQUENCE: 19
atggacatga ggctccctgc tcagctcctg gggctgctaa tgctctgggt cccaggatcc      60
agtggggatg ttgtgatgac tcagtctcca ctctccctgc ccgtcaccct tggacagccg     120
gcctccatct cctgcaggtc tagtcaaagc atcgtacaca gtaacggaaa cacctacttg     180
gagtggtatc tgcagaggcc aggccaatct ccacagctcc taatttataa ggtttctaac     240
cggttctctg ggtcccgaga cagattcagc ggcagtgggt caggcactga tttcacactg     300
aaaatcagca gggtggaggc tgaggatgtt ggggtttatt actgcttcca aggtagccac     360
gttcctctga cgttcggcgg tgggaccaag gtggagatca acgtacggt ggctgcacca     420 tctgtcttca tcttcccgcc atctgatgag cagttgaaat ctggaactgc ctctgttgtg     480
tgcctgctga ataacttcta tcccagagag gccaaagtac agtggaaggt ggataacgcc     540
ctccaatcgg gtaactccca ggagagtgtc acagagcagg acagcaagga cagcacctac     600
agcctcagca gcaccctgac gctgagcaaa gcagactacg agaaacacaa agtctacgcc     660
tgcgaagtca cccatcaggg cctgagctcg cccgtcacaa agagcttcaa caggggagag     720
tgt                                                                   723

<210> SEQ ID NO 20
<211> LENGTH: 241
<212> TYPE: PRT
<213> ORGANISM: Homo sapiens
<220> FEATURE:
<221> NAME/KEY: MISC_FEATURE
<223> OTHER INFORMATION: >2.1 LC D protein

<400> SEQUENCE: 20

Met Asp Met Arg Leu Pro Ala Gln Leu Leu Gly Leu Leu Met Leu Trp
1               5                   10                  15

Val Pro Gly Ser Ser Gly Asp Val Val Met Thr Gln Ser Pro Leu Ser
            20                  25                  30

Leu Pro Val Thr Leu Gly Gln Pro Ala Ser Ile Ser Cys Arg Ser Ser
        35                  40                  45

Gln Ser Ile Val His Ser Asn Gly Asn Thr Tyr Leu Glu Trp Tyr Leu
    50                  55                  60

Gln Arg Pro Gly Gln Ser Pro Gln Leu Leu Ile Tyr Lys Val Ser Asn
65                  70                  75                  80

Arg Phe Ser Gly Val Pro Asp Arg Phe Ser Gly Ser Gly Ser Gly Thr
```

Asp Phe Thr Leu Lys Ile Ser Arg Val Glu Ala Glu Asp Val Gly Val
                85                  90                  95
                                100                 105                 110

Tyr Tyr Cys Phe Gln Gly Ser His Val Pro Leu Thr Phe Gly Gly Gly
            115                 120                 125

Thr Lys Val Glu Ile Lys Arg Thr Val Ala Ala Pro Ser Val Phe Ile
130                 135                 140

Phe Pro Pro Ser Asp Glu Gln Leu Lys Ser Gly Thr Ala Ser Val Val
145                 150                 155                 160

Cys Leu Leu Asn Asn Phe Tyr Pro Arg Glu Ala Lys Val Gln Trp Lys
                165                 170                 175

Val Asp Asn Ala Leu Gln Ser Gly Asn Ser Gln Glu Ser Val Thr Glu
            180                 185                 190

Gln Asp Ser Lys Asp Ser Thr Tyr Ser Leu Ser Ser Thr Leu Thr Leu
        195                 200                 205

Ser Lys Ala Asp Tyr Glu Lys His Lys Val Tyr Ala Cys Glu Val Thr
    210                 215                 220

His Gln Gly Leu Ser Ser Pro Val Thr Lys Ser Phe Asn Arg Gly Glu
225                 230                 235                 240

Cys

<210> SEQ ID NO 21
<211> LENGTH: 723
<212> TYPE: DNA
<213> ORGANISM: Homo sapiens
<220> FEATURE:
<221> NAME/KEY: misc_feature
<223> OTHER INFORMATION: >2.1 LC E DNA

<400> SEQUENCE: 21
atggacatga ggctccctgc tcagctcctg gggctgctaa tgctctgggt cccaggatcc      60
agtggggatg ttgtgatgac tcagtctcca ctctccctgc ccgtcaccct tggacagccg     120
gcctccatct cctgcaggtc tagtcaaagc atcgtacaca gtaacggaaa cacctacttg     180
gagtggtatc tgcagaagcc aggccaatct ccacggctcc taatttataa ggtttctaac     240
cggttctctg ggtcccagac agattcagc ggcagtgggt caggcactga tttcacactg     300
aaaatcagca gggtggaggc tgaggatgtt ggggtttatt actgcttcca aggtagccac     360
gttcctctga cgttcggcgg tgggaccaag gtggagatca aacgtacggt ggctgcacca     420
tctgtcttca tcttcccgcc atctgatgag cagttgaaat ctggaactgc ctctgttgtg     480
tgcctgctga ataacttcta tcccagagag gccaaagtac agtggaaggt ggataacgcc     540
ctccaatcgg gtaactccca ggagagtgtc acagagcagg acagcaagga cagcacctac     600
agcctcagca gcaccctgac gctgagcaaa gcagactacg agaaacacaa agtctacgcc     660
tgcgaagtca cccatcaggg cctgagctcg cccgtcacaa agagcttcaa caggggagag     720
tgt                                                                   723

<210> SEQ ID NO 22
<211> LENGTH: 241
<212> TYPE: PRT
<213> ORGANISM: Homo sapiens
<220> FEATURE:
<221> NAME/KEY: MISC_FEATURE
<223> OTHER INFORMATION: >2.1 LC E protein

<400> SEQUENCE: 22

Met Asp Met Arg Leu Pro Ala Gln Leu Leu Gly Leu Leu Met Leu Trp

```
1               5                  10                 15
Val Pro Gly Ser Ser Gly Asp Val Val Met Thr Gln Ser Pro Leu Ser
            20                  25                 30

Leu Pro Val Thr Leu Gly Gln Pro Ala Ser Ile Ser Cys Arg Ser Ser
            35                  40                 45

Gln Ser Ile Val His Ser Asn Gly Asn Thr Tyr Leu Glu Trp Tyr Leu
50                  55                  60

Gln Lys Pro Gly Gln Ser Pro Arg Leu Leu Ile Tyr Lys Val Ser Asn
65                  70                  75                  80

Arg Phe Ser Gly Val Pro Asp Arg Phe Ser Gly Ser Gly Ser Gly Thr
                85                  90                  95

Asp Phe Thr Leu Lys Ile Ser Arg Val Glu Ala Glu Asp Val Gly Val
            100                 105                110

Tyr Tyr Cys Phe Gln Gly Ser His Val Pro Leu Thr Phe Gly Gly Gly
            115                 120                125

Thr Lys Val Glu Ile Lys Arg Thr Val Ala Ala Pro Ser Val Phe Ile
            130                 135                140

Phe Pro Pro Ser Asp Glu Gln Leu Lys Ser Gly Thr Ala Ser Val Val
145                 150                 155                 160

Cys Leu Leu Asn Asn Phe Tyr Pro Arg Glu Ala Lys Val Gln Trp Lys
                165                 170                 175

Val Asp Asn Ala Leu Gln Ser Gly Asn Ser Gln Glu Ser Val Thr Glu
            180                 185                 190

Gln Asp Ser Lys Asp Ser Thr Tyr Ser Leu Ser Ser Thr Leu Thr Leu
            195                 200                 205

Ser Lys Ala Asp Tyr Glu Lys His Lys Val Tyr Ala Cys Glu Val Thr
210                 215                 220

His Gln Gly Leu Ser Ser Pro Val Thr Lys Ser Phe Asn Arg Gly Glu
225                 230                 235                 240

Cys
```

<210> SEQ ID NO 23
<211> LENGTH: 723
<212> TYPE: DNA
<213> ORGANISM: Homo sapiens
<220> FEATURE:
<221> NAME/KEY: misc_feature
<223> OTHER INFORMATION: >2.1 LC F DNA

<400> SEQUENCE: 23

```
atggacatga ggctccctgc tcagctcctg gggctgctaa tgctctgggt cccaggatcc    60
agtgggdata ttgtgatgac tcagtctcca ctctccctgc ccgtcacccc tggagagccg   120
gcctccatct cctgcaggtc tagtcaaagc atcgtacaca gtaacggaaa cacctacttg   180
gagtggtatc tgcagaggcc aggccaatct ccacagctcc taatttataa ggtttctaac   240
cggttctctg ggtcccaga cagattcagc ggcagtgggt caggcactga tttcacactg   300
aaaatcagca gggtggaggc tgaggatgtt ggggtttatt actgcttcca aggtagccac   360
gttcctctga cgttcggcgg tgggaccaag gtggagatca aacgtacggt ggctgcacca   420
tctgtcttca tcttcccgcc atctgatgag cagttgaaat ctggaactgc ctctgttgtg   480
tgcctgctga ataacttcta tcccagagag gccaaagtac agtggaaggt ggataacgcc   540
ctccaatcgg gtaactccca ggagagtgtc acagagcagg acagcaagga cagcacctac   600
agcctcagca gcaccctgac gctgagcaaa gcagactacg agaaacacaa agtctacgcc   660
tgcgaagtca cccatcaggg cctgagctcg cccgtcacaa agagcttcaa caggggagag   720
``` tgt                                                                         723

<210> SEQ ID NO 24
<211> LENGTH: 241
<212> TYPE: PRT
<213> ORGANISM: Homo sapiens
<220> FEATURE:
<221> NAME/KEY: MISC_FEATURE
<223> OTHER INFORMATION: >2.1 LC F protein

<400> SEQUENCE: 24

Met Asp Met Arg Leu Pro Ala Gln Leu Leu Gly Leu Leu Met Leu Trp
1               5                   10                  15

Val Pro Gly Ser Ser Gly Asp Ile Val Met Thr Gln Ser Pro Leu Ser
            20                  25                  30

Leu Pro Val Thr Pro Gly Glu Pro Ala Ser Ile Ser Cys Arg Ser Ser
        35                  40                  45

Gln Ser Ile Val His Ser Asn Gly Asn Thr Tyr Leu Glu Trp Tyr Leu
    50                  55                  60

Gln Arg Pro Gly Gln Ser Pro Gln Leu Leu Ile Tyr Lys Val Ser Asn
65                  70                  75                  80

Arg Phe Ser Gly Val Pro Asp Arg Phe Ser Gly Ser Gly Ser Gly Thr
                85                  90                  95

Asp Phe Thr Leu Lys Ile Ser Arg Val Glu Ala Glu Asp Val Gly Val
            100                 105                 110

Tyr Tyr Cys Phe Gln Gly Ser His Val Pro Leu Thr Phe Gly Gly Gly
        115                 120                 125

Thr Lys Val Glu Ile Lys Arg Thr Val Ala Ala Pro Ser Val Phe Ile
    130                 135                 140

Phe Pro Pro Ser Asp Glu Gln Leu Lys Ser Gly Thr Ala Ser Val Val
145                 150                 155                 160

Cys Leu Leu Asn Asn Phe Tyr Pro Arg Glu Ala Lys Val Gln Trp Lys
                165                 170                 175

Val Asp Asn Ala Leu Gln Ser Gly Asn Ser Gln Glu Ser Val Thr Glu
            180                 185                 190

Gln Asp Ser Lys Asp Ser Thr Tyr Ser Leu Ser Ser Thr Leu Thr Leu
        195                 200                 205

Ser Lys Ala Asp Tyr Glu Lys His Lys Val Tyr Ala Cys Glu Val Thr
    210                 215                 220

His Gln Gly Leu Ser Ser Pro Val Thr Lys Ser Phe Asn Arg Gly Glu
225                 230                 235                 240

Cys

<210> SEQ ID NO 25
<211> LENGTH: 723
<212> TYPE: DNA
<213> ORGANISM: Homo sapiens
<220> FEATURE:
<221> NAME/KEY: misc_feature
<223> OTHER INFORMATION: >2.1 LC G DNA

<400> SEQUENCE: 25
atggacatga ggctccctgc tcagctcctg gggctgctaa tgctctgggt cccaggatcc      60
agtggggata ttgtgatgac tcagtctcca ctctccctgc ccgtcacccc tggagagccg     120
gcctccatct cctgcaggtc tagtcaaagc atcgtacaca gtaacggaaa cacctacttg     180
gagtggtatc tgcagaagcc aggccaatct ccacggctcc taatttataa ggtttctaac     240

```
cggttctctg gggtcccaga cagattcagc ggcagtgggt caggcactga tttcacactg    300
aaaatcagca gggtggaggc tgaggatgtt ggggtttatt actgcttcca aggtagccac    360
gttcctctga cgttcggcgg tgggaccaag gtggagatca aacgtacggt ggctgcacca    420
tctgtcttca tcttcccgcc atctgatgag cagttgaaat ctggaactgc ctctgttgtg    480
tgcctgctga ataacttcta tcccagagag gccaaagtac agtggaaggt ggataacgcc    540
ctccaatcgg gtaactccca ggagagtgtc acagagcagg acagcaagga cagcacctac    600
agcctcagca gcaccctgac gctgagcaaa gcagactacg agaaacacaa agtctacgcc    660
tgcgaagtca cccatcaggg cctgagctcg cccgtcacaa agagcttcaa caggggagag    720
tgt                                                                   723
```

<210> SEQ ID NO 26
<211> LENGTH: 241
<212> TYPE: PRT
<213> ORGANISM: Homo sapiens
<220> FEATURE:
<221> NAME/KEY: MISC_FEATURE
<223> OTHER INFORMATION: >2.1 LC G protein

<400> SEQUENCE: 26

```
Met Asp Met Arg Leu Pro Ala Gln Leu Leu Gly Leu Leu Met Leu Trp
1               5                   10                  15

Val Pro Gly Ser Ser Gly Asp Ile Val Met Thr Gln Ser Pro Leu Ser
            20                  25                  30

Leu Pro Val Thr Pro Gly Glu Pro Ala Ser Ile Ser Cys Arg Ser Ser
        35                  40                  45

Gln Ser Ile Val His Ser Asn Gly Asn Thr Tyr Leu Glu Trp Tyr Leu
    50                  55                  60

Gln Lys Pro Gly Gln Ser Pro Arg Leu Leu Ile Tyr Lys Val Ser Asn
65                  70                  75                  80

Arg Phe Ser Gly Val Pro Asp Arg Phe Ser Gly Ser Gly Ser Gly Thr
                85                  90                  95

Asp Phe Thr Leu Lys Ile Ser Arg Val Glu Ala Glu Asp Val Gly Val
            100                 105                 110

Tyr Tyr Cys Phe Gln Gly Ser His Val Pro Leu Thr Phe Gly Gly Gly
        115                 120                 125

Thr Lys Val Glu Ile Lys Arg Thr Val Ala Ala Pro Ser Val Phe Ile
    130                 135                 140

Phe Pro Pro Ser Asp Glu Gln Leu Lys Ser Gly Thr Ala Ser Val Val
145                 150                 155                 160

Cys Leu Leu Asn Asn Phe Tyr Pro Arg Glu Ala Lys Val Gln Trp Lys
                165                 170                 175

Val Asp Asn Ala Leu Gln Ser Gly Asn Ser Gln Glu Ser Val Thr Glu
            180                 185                 190

Gln Asp Ser Lys Asp Ser Thr Tyr Ser Leu Ser Ser Thr Leu Thr Leu
        195                 200                 205

Ser Lys Ala Asp Tyr Glu Lys His Lys Val Tyr Ala Cys Glu Val Thr
    210                 215                 220

His Gln Gly Leu Ser Ser Pro Val Thr Lys Ser Phe Asn Arg Gly Glu
225                 230                 235                 240

Cys
```

<210> SEQ ID NO 27
<211> LENGTH: 723
<212> TYPE: DNA

<213> ORGANISM: Homo sapiens
<220> FEATURE:
<221> NAME/KEY: misc_feature
<223> OTHER INFORMATION: >2.1 LC I DNA

<400> SEQUENCE: 27

```
atggacatga ggctccctgc tcagctcctg gggctgctaa tgctctgggt cccaggatcc      60
agtggggata ttgtgatgac tcagtctcca ctctccctgc ccgtcacccc tggagagccg     120
gcctccatct cctgcaggtc tagtcaaagc atcgtacaca gtaacggaaa cacctacttg     180
gagtggtatc tgcagaagcc aggccaatct ccacagctcc taatttataa ggtttctaac     240
cggttctctg ggtcccaga cagattcagc ggcagtgggt caggcactga tttcacactg     300
aaaatcagca gggtggaggc tgaggatgtt ggggtttatt actgcttcca aggtagccac     360
gttcctctga cgttcggcgg tgggaccaag gtggagatca aacgtacggt ggctgcacca     420
tctgtcttca tcttcccgcc atctgatgag cagttgaaat ctggaactgc ctctgttgtg     480
tgcctgctga ataacttcta tcccagagag gccaaagtac agtggaaggt ggataacgcc     540
ctccaatcgg gtaactccca ggagagtgtc acagagcagg acagcaagga cagcacctac     600
agcctcagca gcaccctgac gctgagcaaa gcagactacg agaaacacaa agtctacgcc     660
tgcgaagtca cccatcaggg cctgagctcg cccgtcacaa agagcttcaa caggggagag     720
tgt                                                                    723
```

<210> SEQ ID NO 28
<211> LENGTH: 241
<212> TYPE: PRT
<213> ORGANISM: Homo sapiens
<220> FEATURE:
<221> NAME/KEY: MISC_FEATURE
<223> OTHER INFORMATION: >2.1 LC I protein

<400> SEQUENCE: 28

```
Met Asp Met Arg Leu Pro Ala Gln Leu Leu Gly Leu Leu Met Leu Trp
1               5                   10                  15
Val Pro Gly Ser Ser Gly Asp Ile Val Met Thr Gln Ser Pro Leu Ser
            20                  25                  30
Leu Pro Val Thr Pro Gly Glu Pro Ala Ser Ile Ser Cys Arg Ser Ser
        35                  40                  45
Gln Ser Ile Val His Ser Asn Gly Asn Thr Tyr Leu Glu Trp Tyr Leu
    50                  55                  60
Gln Lys Pro Gly Gln Ser Pro Gln Leu Leu Ile Tyr Lys Val Ser Asn
65                  70                  75                  80
Arg Phe Ser Gly Val Pro Asp Arg Phe Ser Gly Ser Gly Ser Gly Thr
                85                  90                  95
Asp Phe Thr Leu Lys Ile Ser Arg Val Glu Ala Glu Asp Val Gly Val
            100                 105                 110
Tyr Tyr Cys Phe Gln Gly Ser His Val Pro Leu Thr Phe Gly Gly Gly
        115                 120                 125
Thr Lys Val Glu Ile Lys Arg Thr Val Ala Ala Pro Ser Val Phe Ile
    130                 135                 140
Phe Pro Pro Ser Asp Glu Gln Leu Lys Ser Gly Thr Ala Ser Val Val
145                 150                 155                 160
Cys Leu Leu Asn Asn Phe Tyr Pro Arg Glu Ala Lys Val Gln Trp Lys
                165                 170                 175
Val Asp Asn Ala Leu Gln Ser Gly Asn Ser Gln Glu Ser Val Thr Glu
            180                 185                 190
```

-continued

```
Gln Asp Ser Lys Asp Ser Thr Tyr Ser Leu Ser Ser Thr Leu Thr Leu
    195                 200                 205
Ser Lys Ala Asp Tyr Glu Lys His Lys Val Tyr Ala Cys Glu Val Thr
    210                 215                 220
His Gln Gly Leu Ser Ser Pro Val Thr Lys Ser Phe Asn Arg Gly Glu
225                 230                 235                 240
Cys

<210> SEQ ID NO 29
<211> LENGTH: 1410
<212> TYPE: DNA
<213> ORGANISM: Homo sapiens
<220> FEATURE:
<221> NAME/KEY: misc_feature
<223> OTHER INFORMATION: >2.1 HC "humanized K5R" DNA

<400> SEQUENCE: 29
atggacacac tttgctccac gctcctgctg ctgaccatcc cttcatgggt cttgtcccag      60
gtcaccttga gggagtctgg tcctgcgctg gtgaaaccca cagaccct cacgctgacc      120
tgcaccttct ctgggttctc actccgcact agtggaatgg gcgtgggctg gatccgtcag      180
cccccaggaa aggccctgga gtggcttgcc cacatttggt gggatgatga taagagctac      240
aacccatctc tgaagagcca gctcaccatc tctaaggaca cctccaaaaa ccaggtggtc      300
cttacaatga ccaacatgga ccctgtggac acagccacat attactgtgc acgcagaaac      360
tattactacg acgactactt cgcctactgg ggccagggca ccctggtcac cgtctctagt      420
gcctccacca agggcccatc ggtcttcccc ctggcaccct cctccaagag cacctctggg      480
ggcacagcgg ccctgggctg cctggtcaag gactacttcc ccgaaccggt gacggtgtcg      540
tggaactcag gcgccctgac cagcggcgtg cacaccttcc cggctgtcct acagtcctca      600
ggactctact ccctcagcag cgtggtgacc gtgccctcca gcagcttggg cacccagacc      660
tacatctgca acgtgaatca caagcccagc aacaccaagg tggacaagaa agttgagccc      720
aaatcttgtg acaaaactca cacatgccca ccgtgcccag cacctgaact cctggggga      780
ccgtcagtct tcctcttccc cccaaaaccc aaggacaccc tcatgatctc ccggacccct      840
gaggtcacat gcgtggtggt ggacgtgagc cacgaagacc ctgaggtcaa gttcaactgg      900
tacgtggacg gcgtggaggt gcataatgcc aagacaaagc cgcgggagga gcagtacaac      960
agcacgtacc gtgtggtcag cgtcctcacc gtcctgcacc aggactggct gaatggcaag     1020
gagtacaagt gcaaggtctc caacaaagcc ctcccagccc ccatcgagaa aaccatctcc     1080
aaagccaaag ggcagccccg agaaccacag gtgtacaccc tgcccccatc ccgggatgag     1140
ctgaccaaga accaggtcag cctgacctgc ctggtcaaag gcttctatcc cagcgacatc     1200
gccgtggagt gggagagcaa tgggcagccg gagaacaact acaagaccac gcctcccgtg     1260
ctggactccg acggctcctt cttcctctat agcaagctca ccgtggacaa gagcaggtgg     1320
cagcagggga acgtcttctc atgctccgtg atgcatgagg ctctgcacaa ccactacacg     1380
cagaagagcc tctccctgtc tccgggtaaa                                      1410

<210> SEQ ID NO 30
<211> LENGTH: 470
<212> TYPE: PRT
<213> ORGANISM: Homo sapiens
<220> FEATURE:
<221> NAME/KEY: MISC_FEATURE
<223> OTHER INFORMATION: >2.1 HC "humanized K5R" protein

<400> SEQUENCE: 30
```

```
Met Asp Thr Leu Cys Ser Thr Leu Leu Leu Thr Ile Pro Ser Trp
1               5                   10                  15

Val Leu Ser Gln Val Thr Leu Arg Glu Ser Gly Pro Ala Leu Val Lys
            20                  25                  30

Pro Thr Gln Thr Leu Thr Leu Thr Cys Thr Phe Ser Gly Phe Ser Leu
            35                  40                  45

Arg Thr Ser Gly Met Gly Val Gly Trp Ile Arg Gln Pro Pro Gly Lys
50                  55                  60

Ala Leu Glu Trp Leu Ala His Ile Trp Trp Asp Asp Lys Ser Tyr
65              70                  75                  80

Asn Pro Ser Leu Lys Ser Gln Leu Thr Ile Ser Lys Asp Thr Ser Lys
            85                  90                  95

Asn Gln Val Val Leu Thr Met Thr Asn Met Asp Pro Val Asp Thr Ala
            100                 105                 110

Thr Tyr Tyr Cys Ala Arg Arg Asn Tyr Tyr Asp Asp Tyr Phe Ala
            115                 120                 125

Tyr Trp Gly Gln Gly Thr Leu Val Thr Val Ser Ser Ala Ser Thr Lys
130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
            165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
            195                 200                 205

Val Thr Val Pro Ser Ser Leu Gly Thr Gln Thr Tyr Ile Cys Asn
            210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
            245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
            275                 280                 285

Val Ser His Glu Asp Pro Glu Val Lys Phe Asn Trp Tyr Val Asp Gly
            290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
            325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
            355                 360                 365

Pro Gln Val Tyr Thr Leu Pro Pro Ser Arg Asp Glu Leu Thr Lys Asn
370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
            405                 410                 415

Thr Pro Pro Val Leu Asp Ser Asp Gly Ser Phe Phe Leu Tyr Ser Lys
```

```
                420             425             430
Leu Thr Val Asp Lys Ser Arg Trp Gln Gln Gly Asn Val Phe Ser Cys
            435                 440                 445
Ser Val Met His Glu Ala Leu His Asn His Tyr Thr Gln Lys Ser Leu
        450                 455                 460
Ser Leu Ser Pro Gly Lys
465                 470

<210> SEQ ID NO 31
<211> LENGTH: 1410
<212> TYPE: DNA
<213> ORGANISM: Homo sapiens
<220> FEATURE:
<221> NAME/KEY: misc_feature
<223> OTHER INFORMATION: >HC-rehumanized DNA

<400> SEQUENCE: 31
atggacacac tttgctccac gctcctgctg ctgaccatcc cttcatgggt cttgtcccag      60
gtcaccttga aggagtctgg tcctgcgctg gtgaaaccca cagaccct cacgctgacc      120 tgcaccttct ctgggttctc actccgcact agtggaatgg cgtgggctg atccgtcag       180 cccccaggaa agggcctgga gtggcttgcc cacatttggt gggatgatga taagagctac      240
aacccatctc tgaagagcca gctcaccatc tctaaggaca cctccaaaaa ccaggtggtc      300
cttacaatga ccaacatgga ccctgtggac acagccacat attactgtgc acgcagaaac      360
tattactacg acgactactt cgcctactgg ggccagggca ccactcac cgtctctagt       420 gcctccacca agggcccatc ggtcttcccc ctggcaccct cctccaagag cacctctggg      480
ggcacagcgg ccctgggctg cctggtcaag gactacttcc ccgaaccggt gacggtgtcg      540
tggaactcag gcgccctgac cagcggcgtg cacaccttcc cggctgtcct acagtcctca      600
ggactctact ccctcagcag cgtggtgacc gtgccctcca gcagcttggg cacccagacc      660
tacatctgca acgtgaatca caagcccagc aacaccaagg tggacaagaa agttgagccc      720
aaatcttgtg acaaaactca cacatgccca ccgtgccag cacctgaact cctgggggga     780
ccgtcagtct tcctcttccc cccaaaaccc aaggacaccc tcatgatctc ccggacccct     840
gaggtcacat gcgtggtggt ggacgtgagc cacgaagacc ctgaggtcaa gttcaactgg      900
tacgtggacg gcgtggaggt gcataatgcc aagacaaagc cgcgggagga gcagtacaac      960
agcacgtacc gtgtggtcag cgtcctcacc gtcctgcacc aggactggct gaatggcaag     1020
gagtacaagt gcaaggtctc caacaaagcc ctcccagccc ccatcgagaa aaccatctcc     1080
aaagccaaag ggcagccccg agaaccacag gtgtacaccc tgcccccatc ccgggatgag     1140
ctgaccaaga accaggtcag cctgacctgc ctggtcaaag gcttctatcc cagcgacatc     1200
gccgtggagt gggagagcaa tgggcagccg gagaacaact acaagaccac gcctcccgtg     1260
ctggactccg acggctcctt cttcctctat agcaagctca ccgtggacaa gagcaggtgg     1320
cagcagggga acgtcttctc atgctccgtg atgcatgagg ctctgcacaa ccactacacg     1380
cagaagagcc tctccctgtc tccgggtaaa                                     1410

<210> SEQ ID NO 32
<211> LENGTH: 451
<212> TYPE: PRT
<213> ORGANISM: Homo sapiens
<220> FEATURE:
<221> NAME/KEY: MISC_FEATURE
<223> OTHER INFORMATION: >HC-rehumanized amino acid

<400> SEQUENCE: 32
```

-continued

```
Gln Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Arg Thr Ser
            20                  25                  30

Gly Met Gly Val Gly Trp Ile Arg Gln Pro Pro Gly Lys Gly Leu Glu
        35                  40                  45

Trp Leu Ala His Ile Trp Trp Asp Asp Asp Lys Ser Tyr Asn Pro Ser
    50                  55                  60

Leu Lys Ser Gln Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Arg Asn Tyr Tyr Tyr Asp Asp Tyr Phe Ala Tyr Trp Gly
            100                 105                 110

Gln Gly Thr Thr Leu Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
```

```
                420             425             430
His Glu Ala Leu His Asn His Tyr Thr Gln Lys Ser Leu Ser Leu Ser
        435                 440                 445

Pro Gly Lys
    450
```

<210> SEQ ID NO 33
<211> LENGTH: 723
<212> TYPE: DNA
<213> ORGANISM: Homo sapiens
<220> FEATURE:
<221> NAME/KEY: misc_feature
<223> OTHER INFORMATION: >LC-humanized DNA

<400> SEQUENCE: 33

```
atggacatga ggctccctgc tcagctcctg gggctgctaa tgctctgggt cccaggatcc    60
agtggggatg ttgtgatgac tcagtctcca ctctccctgc ccgtcaccct tggacagccg   120
gcctccatct cctgcaggtc tagtcaaagc atcgtacaca gtaacggaaa cacctacttg   180
gagtggtttc agcagaggcc aggccaatct ccaaggcgcc taatttataa ggtttctaac   240
cggttctctg ggtcccccaga cagattcagc ggcagtgggt caggcactga tttcacactg   300
aaaatcagca gggtggaggc tgaggatgtt gggggtttatt actgcttcca aggtagccac   360
gttcctctga cgttcggcca agggaccaag ctggaaatca aacggactgt ggctgcacca   420
tctgtcttca tcttcccgcc atctgatgag cagttgaaat ctggaactgc ctctgttgtg   480
tgcctgctga taacttcta tcccagagag gccaaagtac agtggaaggt ggataacgcc   540
ctccaatcgg gtaactccca ggagagtgtc acagagcagg acagcaagga cagcacctac   600
agcctcagca gcaccctgac gctgagcaaa gcagactacg agaaacacaa agtctacgcc   660
tgcgaagtca cccatcaggg cctgagctcg cccgtcacaa agagcttcaa caggggagag   720
tgt                                                                  723
```

<210> SEQ ID NO 34
<211> LENGTH: 219
<212> TYPE: PRT
<213> ORGANISM: Homo sapiens
<220> FEATURE:
<221> NAME/KEY: MISC_FEATURE
<223> OTHER INFORMATION: >LC-humanized amino acid

<400> SEQUENCE: 34

```
Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Ile Val His Ser
            20                  25                  30

Asn Gly Asn Thr Tyr Leu Glu Trp Phe Gln Gln Arg Pro Gly Gln Ser
        35                  40                  45

Pro Arg Arg Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Leu Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125
```

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 35
<211> LENGTH: 100
<212> TYPE: PRT
<213> ORGANISM: Homo sapiens
<220> FEATURE:
<221> NAME/KEY: MISC_FEATURE
<223> OTHER INFORMATION: >VH2-70

<400> SEQUENCE: 35

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Cys Val Ser Trp Ile Arg Gln Pro Pro Gly Lys Ala Leu Glu
        35                  40                  45

Trp Leu Ala Leu Ile Asp Trp Asp Asp Lys Tyr Tyr Ser Thr Ser
50                  55                  60

Leu Lys Thr Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Ile
            100

<210> SEQ ID NO 36
<211> LENGTH: 100
<212> TYPE: PRT
<213> ORGANISM: Homo sapiens
<220> FEATURE:
<221> NAME/KEY: MISC_FEATURE
<223> OTHER INFORMATION: > VKII A1

<400> SEQUENCE: 36

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Trp Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro

<210> SEQ ID NO 37
<211> LENGTH: 121
<212> TYPE: PRT
<213> ORGANISM: Mus musculus
<220> FEATURE:
<221> NAME/KEY: MISC_FEATURE
<223> OTHER INFORMATION: Heavy chain variable region sequence of murine mAb2.1

<400> SEQUENCE: 37

Gln Val Thr Leu Lys Glu Ser Gly Pro Gly Ile Leu Lys Pro Ser Gln
1               5                   10                  15

Thr Leu Ser Leu Thr Cys Ser Phe Ser Gly Phe Ser Leu Arg Thr Ser
            20                  25                  30

Gly Met Gly Val Gly Trp Ile Arg Gln Pro Ser Gly Lys Gly Leu Glu
        35                  40                  45

Trp Leu Ala His Ile Trp Trp Asp Asp Lys Ser Tyr Asn Pro Ser
    50                  55                  60

Leu Lys Ser Gln Leu Thr Ile Ser Lys Asp Thr Ser Arg Asn Gln Val
65                  70                  75                  80

Phe Leu Lys Ile Thr Ser Val Asp Thr Ala Asp Thr Ala Thr Tyr Tyr
                85                  90                  95

Cys Ala Arg Arg Asn Tyr Tyr Tyr Asp Asp Tyr Phe Ala Tyr Trp Gly
            100                 105                 110

Gln Gly Thr Thr Leu Thr Val Ser Ser
        115                 120

<210> SEQ ID NO 38
<211> LENGTH: 121
<212> TYPE: PRT
<213> ORGANISM: Artificial Sequence
<220> FEATURE:
<223> OTHER INFORMATION: Humanized heavy chain variable region sequence of murine 2.1 HC X

<400> SEQUENCE: 38

Gln Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Arg Thr Ser
            20                  25                  30

Gly Met Gly Val Gly Trp Ile Arg Gln Pro Pro Gly Lys Ala Leu Glu
        35                  40                  45

Trp Leu Ala His Ile Trp Trp Asp Asp Lys Ser Tyr Asn Pro Ser
    50                  55                  60

Leu Lys Ser Gln Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Arg Asn Tyr Tyr Tyr Asp Asp Tyr Phe Ala Tyr Trp Gly
            100                 105                 110

Gln Gly Thr Leu Val Thr Val Ser Ser
        115                 120

<210> SEQ ID NO 39
<211> LENGTH: 121
<212> TYPE: PRT
<213> ORGANISM: Artificial Sequence
<220> FEATURE:
<223> OTHER INFORMATION: Humanized heavy chain variable region sequence of murine 2.1 HC Y

<400> SEQUENCE: 39

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Arg Thr Ser
            20                  25                  30

Gly Met Gly Val Gly Trp Ile Arg Gln Pro Pro Gly Lys Ala Leu Glu
        35                  40                  45

Trp Leu Ala His Ile Trp Trp Asp Asp Lys Ser Tyr Asn Pro Ser
    50                  55                  60

Leu Lys Ser Gln Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Arg Asn Tyr Tyr Tyr Asp Asp Tyr Phe Ala Tyr Trp Gly
            100                 105                 110

Gln Gly Thr Leu Val Thr Val Ser Ser
        115                 120

<210> SEQ ID NO 40
<211> LENGTH: 121
<212> TYPE: PRT
<213> ORGANISM: Artificial Sequence
<220> FEATURE:
<223> OTHER INFORMATION: Humanized heavy chain variable region sequence
      of murine 2.1 HC Z

<400> SEQUENCE: 40

Gln Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Arg Thr Ser
            20                  25                  30

Gly Met Gly Val Gly Trp Ile Arg Gln Pro Pro Gly Lys Gly Leu Glu
        35                  40                  45

Trp Leu Ala His Ile Trp Trp Asp Asp Lys Ser Tyr Asn Pro Ser
    50                  55                  60

Leu Lys Ser Gln Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Arg Asn Tyr Tyr Tyr Asp Asp Tyr Phe Ala Tyr Trp Gly
            100                 105                 110

Gln Gly Thr Thr Leu Thr Val Ser Ser
        115                 120

<210> SEQ ID NO 41
<211> LENGTH: 121
<212> TYPE: PRT
<213> ORGANISM: Homo sapiens
<220> FEATURE:
<221> NAME/KEY: MISC_FEATURE
<222> LOCATION: (31)..(37)
<223> OTHER INFORMATION: Xaa is any naturally occurring amino acid
<220> FEATURE:
<221> NAME/KEY: MISC_FEATURE
<222> LOCATION: (52)..(67)
<223> OTHER INFORMATION: Xaa is any naturally occurring amino acid
<220> FEATURE:
<221> NAME/KEY: MISC_FEATURE
<222> LOCATION: (101)..(110)
<223> OTHER INFORMATION: Xaa is any naturally occurring amino acid -continued

```
<400> SEQUENCE: 41

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Xaa Xaa
            20                  25                  30

Xaa Xaa Xaa Xaa Xaa Trp Ile Arg Gln Pro Pro Gly Lys Ala Leu Glu
        35                  40                  45

Trp Leu Ala Xaa Xaa Xaa Xaa Xaa Xaa Xaa Xaa Xaa Xaa Xaa Xaa Xaa
50                  55                  60

Xaa Xaa Xaa Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Ile Xaa Xaa Xaa Xaa Xaa Xaa Xaa Xaa Xaa Xaa Trp Gly
            100                 105                 110

Gln Gly Thr Leu Val Thr Val Ser Ser
            115                 120

<210> SEQ ID NO 42
<211> LENGTH: 112
<212> TYPE: PRT
<213> ORGANISM: Mus musculus
<220> FEATURE:
<221> NAME/KEY: MISC_FEATURE
<223> OTHER INFORMATION: Light chain variable region sequence of murine
      mAb2.1

<400> SEQUENCE: 42

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Leu Thr Phe Gly Ala Gly Thr Lys Leu Glu Leu Lys
            100                 105                 110

<210> SEQ ID NO 43
<211> LENGTH: 112
<212> TYPE: PRT
<213> ORGANISM: Artificial Sequence
<220> FEATURE:
<223> OTHER INFORMATION: Humanized 2.1 LC A sequence

<400> SEQUENCE: 43

Asp Val Leu Met Thr Gln Ser Pro Leu Ser Leu Pro Val Thr Leu Gly
1               5                   10                  15

Gln Pro Ala Ser Ile Ser Cys Arg Ser Ser Gln Ser Ile Val His Ser
            20                  25                  30

Asn Gly Asn Thr Tyr Leu Glu Trp Tyr Leu Gln Arg Pro Gly Gln Ser
        35                  40                  45

Pro Lys Leu Leu Ile Tyr Lys Val Ser Asn Arg Phe Ser Gly Val Pro
```

```
                    50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Phe Gln Gly
                     85                  90                  95

Ser His Val Pro Leu Thr Phe Gly Ala Gly Thr Lys Leu Glu Ile Lys
                100                 105                 110

<210> SEQ ID NO 44
<211> LENGTH: 112
<212> TYPE: PRT
<213> ORGANISM: Artificial Sequence
<220> FEATURE:
<223> OTHER INFORMATION: Humanized 2.1 LC B sequence

<400> SEQUENCE: 44

Asp Val Val Met Thr Gln Ser Pro Leu Ser Leu Pro Val Thr Leu Gly
  1               5                  10                  15

Gln Pro Ala Ser Ile Ser Cys Arg Ser Ser Gln Ser Ile Val His Ser
                 20                  25                  30

Asn Gly Asn Thr Tyr Leu Glu Trp Phe Val Gln Arg Pro Gly Gln Ser
             35                  40                  45

Pro Arg Val Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Phe Gln Gly
                     85                  90                  95

Ser His Val Pro Leu Thr Phe Gly Gly Gly Thr Lys Leu Glu Ile Lys
                100                 105                 110

<210> SEQ ID NO 45
<211> LENGTH: 112
<212> TYPE: PRT
<213> ORGANISM: Artificial Sequence
<220> FEATURE:
<223> OTHER INFORMATION: Humanized 2.1 LC C sequence

<400> SEQUENCE: 45

Asp Val Val Met Thr Gln Ser Pro Leu Ser Leu Pro Val Thr Leu Gly
  1               5                  10                  15

Gln Pro Ala Ser Ile Ser Cys Arg Ser Ser Gln Ser Ile Val His Ser
                 20                  25                  30

Asn Gly Asn Thr Tyr Leu Glu Trp Tyr Leu Gln Arg Pro Gly Gln Ser
             35                  40                  45

Pro Gln Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Phe Gln Gly
                     85                  90                  95

Ser His Val Pro Leu Thr Phe Gly Gln Gly Thr Lys Leu Glu Ile Lys
                100                 105                 110
```

<210> SEQ ID NO 46
<211> LENGTH: 112
<212> TYPE: PRT
<213> ORGANISM: Artificial Sequence
<220> FEATURE:
<223> OTHER INFORMATION: Humanized 2.1 LC D sequence

<400> SEQUENCE: 46

```
Asp Val Val Met Thr Gln Ser Pro Leu Ser Leu Pro Val Thr Leu Gly
  1               5                  10                  15

Gln Pro Ala Ser Ile Ser Cys Arg Ser Ser Gln Ser Ile Val His Ser
             20                  25                  30

Asn Gly Asn Thr Tyr Leu Glu Trp Tyr Leu Gln Arg Pro Gly Gln Ser
         35                  40                  45

Pro Gln Leu Leu Ile Tyr Lys Val Ser Asn Arg Phe Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Phe Gln Gly
                 85                  90                  95

Ser His Val Pro Leu Thr Phe Gly Gly Gly Thr Lys Val Glu Ile Lys
            100                 105                 110
```

<210> SEQ ID NO 47
<211> LENGTH: 112
<212> TYPE: PRT
<213> ORGANISM: Artificial Sequence
<220> FEATURE:
<223> OTHER INFORMATION: Humanized 2.1 LC E sequence

<400> SEQUENCE: 47

```
Asp Val Val Met Thr Gln Ser Pro Leu Ser Leu Pro Val Thr Leu Gly
  1               5                  10                  15

Gln Pro Ala Ser Ile Ser Cys Arg Ser Ser Gln Ser Ile Val His Ser
             20                  25                  30

Asn Gly Asn Thr Tyr Leu Glu Trp Tyr Leu Gln Lys Pro Gly Gln Ser
         35                  40                  45

Pro Arg Leu Leu Ile Tyr Lys Val Ser Asn Arg Phe Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Phe Gln Gly
                 85                  90                  95

Ser His Val Pro Leu Thr Phe Gly Gly Gly Thr Lys Val Glu Ile Lys
            100                 105                 110
```

<210> SEQ ID NO 48
<211> LENGTH: 112
<212> TYPE: PRT
<213> ORGANISM: Artificial Sequence
<220> FEATURE:
<223> OTHER INFORMATION: Humanized 2.1 LC F sequence

<400> SEQUENCE: 48

```
Asp Ile Val Met Thr Gln Ser Pro Leu Ser Leu Pro Val Thr Pro Gly
  1               5                  10                  15

Glu Pro Ala Ser Ile Ser Cys Arg Ser Ser Gln Ser Ile Val His Ser
             20                  25                  30

Asn Gly Asn Thr Tyr Leu Glu Trp Tyr Leu Gln Arg Pro Gly Gln Ser
         35                  40                  45
```

```
Pro Gln Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Leu Thr Phe Gly Gly Gly Thr Lys Val Glu Ile Lys
            100                 105                 110

<210> SEQ ID NO 49
<211> LENGTH: 112
<212> TYPE: PRT
<213> ORGANISM: Artificial Sequence
<220> FEATURE:
<223> OTHER INFORMATION: Humanized 2.1 LC G sequence

<400> SEQUENCE: 49

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Ile Val His Ser
                20                  25                  30

Asn Gly Asn Thr Tyr Leu Glu Trp Tyr Leu Gln Lys Pro Gly Gln Ser
            35                  40                  45

Pro Arg Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Leu Thr Phe Gly Gly Gly Thr Lys Val Glu Ile Lys
            100                 105                 110

<210> SEQ ID NO 50
<211> LENGTH: 112
<212> TYPE: PRT
<213> ORGANISM: Artificial Sequence
<220> FEATURE:
<223> OTHER INFORMATION: Humanized 2.1 LC I sequence

<400> SEQUENCE: 50

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Ile Val His Ser
                20                  25                  30

Asn Gly Asn Thr Tyr Leu Glu Trp Tyr Leu Gln Lys Pro Gly Gln Ser
            35                  40                  45

Pro Gln Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Leu Thr Phe Gly Gly Gly Thr Lys Val Glu Ile Lys
            100                 105                 110

<210> SEQ ID NO 51
<211> LENGTH: 112
<212> TYPE: PRT
<213> ORGANISM: Artificial Sequence
```

```
<220> FEATURE:
<223> OTHER INFORMATION: Humanized 2.1 LC J sequence

<400> SEQUENCE: 51

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Ile Val His Ser
            20                  25                  30

Asn Gly Asn Thr Tyr Leu Glu Trp Phe Gln Gln Arg Pro Gly Gln Ser
        35                  40                  45

Pro Arg Arg Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Leu Thr Phe Gly Gln Gly Thr Lys Leu Glu Ile Lys
            100                 105                 110

<210> SEQ ID NO 52
<211> LENGTH: 112
<212> TYPE: PRT
<213> ORGANISM: Homo sapiens
<220> FEATURE:
<221> NAME/KEY: MISC_FEATURE
<223> OTHER INFORMATION: VKII A19/JK4 sequence
<220> FEATURE:
<221> NAME/KEY: MISC_FEATURE
<222> LOCATION: (24)..(39)
<223> OTHER INFORMATION: Xaa is any naturally occurring amino acid
<220> FEATURE:
<221> NAME/KEY: MISC_FEATURE
<222> LOCATION: (55)..(61)
<223> OTHER INFORMATION: Xaa is any naturally occurring amino acid
<220> FEATURE:
<221> NAME/KEY: MISC_FEATURE
<222> LOCATION: (94)..(102)
<223> OTHER INFORMATION: Xaa is any naturally occurring amino acid

<400> SEQUENCE: 52

Asp Ile Val Met Thr Gln Ser Pro Leu Ser Leu Pro Val Thr Pro Gly
1               5                   10                  15

Glu Pro Ala Ser Ile Ser Cys Xaa Xaa Xaa Xaa Xaa Xaa Xaa Xaa Xaa
            20                  25                  30

Xaa Xaa Xaa Xaa Xaa Xaa Xaa Trp Tyr Leu Gln Lys Pro Gly Gln Ser
        35                  40                  45

Pro Gln Leu Leu Ile Tyr Xaa Xaa Xaa Xaa Xaa Xaa Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Xaa Xaa Xaa
                85                  90                  95

Xaa Xaa Xaa Xaa Xaa Xaa Phe Gly Gly Gly Thr Lys Val Glu Ile Lys
            100                 105                 110
```